United States Patent
Wright et al.

(10) Patent No.: US 11,806,740 B1
(45) Date of Patent: Nov. 7, 2023

(54) DISPOSABLE CARTRIDGES FOR ELECTROSPRAYING APPLICATORS, SYSTEMS, AND METHODS THEREOF

(71) Applicant: Octet Medical, Inc., San Diego, CA (US)

(72) Inventors: Clifford A. Wright, San Diego, CA (US); Kyle Elsabee, San Diego, CA (US); Ben Reisman, San Diego, CA (US); Ron Lawrence, San Diego, CA (US); Dan Ortuno, San Diego, CA (US); Gusten Brainerd, San Diego, CA (US); Matthew Michael Wold, Escondido, CA (US); Michael Williams, San Diego, CA (US)

(73) Assignee: Octet Medical, Inc., San Diego, CA (US)

( * ) Notice: Subject to any disclaimer, the term of this patent is extended or adjusted under 35 U.S.C. 154(b) by 0 days.

(21) Appl. No.: 18/110,854

(22) Filed: Feb. 16, 2023

Related U.S. Application Data

(60) Provisional application No. 63/411,334, filed on Sep. 29, 2022.

(51) Int. Cl.
*B05B 5/16* (2006.01)
*A61M 35/00* (2006.01)

(52) U.S. Cl.
CPC ......... *B05B 5/1691* (2013.01); *A61M 35/003* (2013.01); *B05B 5/1675* (2013.01)

(58) Field of Classification Search
None
See application file for complete search history.

(56) References Cited

U.S. PATENT DOCUMENTS

2014/0263694 A1\* 9/2014 Lin ..................... A01K 67/033
                                                                239/3
2019/0060922 A1\* 2/2019 Wright .................. B05B 5/004

\* cited by examiner

*Primary Examiner* — Alexander M Weddle
(74) *Attorney, Agent, or Firm* — Snell & Wilmer L.L.P.

(57) ABSTRACT

A disposable fluid delivery system for an electrostatic applicator. The system includes a nozzle housing comprising an air supply port, a voltage port, and a delivery outlet. A voltage wire has a contact in communication with a delivery tube in fluid communication with the delivery outlet. A syringe includes a barrel portion and a plunger configured to advance fluids from within the barrel portion and through the delivery tube. A cartridge housing can at least partially enclose the nozzle housing, the voltage wire, and the syringe.

20 Claims, 35 Drawing Sheets

3100

---

INSERTING A FIRST DISPOSABLE CARTRIDGE INTO A CHAMBER HOUSING OF THE ELECTROSTATIC SPRAYER SYSTEM SUCH THAT A VOLTAGE CONTACT AT A FIRST END OF A VOLTAGE WIRE WITHIN THE FIRST DISPOSABLE CARTRIDGE CONTACTS A VOLTAGE CONTACT OF THE ELECTROSTATIC APPLICATOR SYSTEM; A FIRST END OF AN AIR SUPPLY PORT WITHIN THE FIRST DISPOSABLE CARTRIDGE FLUIDLY CONNECTS WITH AN AIR SUPPLY PORT OF THE ELECTROSTATIC APPLICATOR SYSTEM; AND A PLUNGER OF A SYRINGE WITHIN THE FIRST DISPOSABLE CARTRIDGE ALIGNS WITH A PISTON OF THE ELECTROSTATIC APPLICATOR SYSTEM, THE SYRINGE CONTAINING A FIRST FLUID;
3110

---

CAUSING, BY AN ACTIVATION INPUT TO THE ELECTROSTATIC APPLICATOR SYSTEM, A MOTOR TO ACTUATE AND A VOLTAGE POTENTIAL TO BE DELIVERED TO A DELIVERY TUBE OF THE FIRST DISPOSABLE CARTRIDGE
3120

CAUSING, BY AN ACTIVATION INPUT TO THE ELECTROSTATIC APPLICATOR SYSTEM, A MOTOR TO ACTUATE AND/OR A VOLTAGE POTENTIAL TO BE DELIVERED FROM A HIGH VOLTAGE MODULE OF THE ELECTROSTATIC APPLICATOR SYSTEM VIA A VOLTAGE WIRE OF THE DISPOSABLE CARTRIDGE TO A DELIVERY TUBE OF A DISPOSABLE CARTRIDGE REMOVABLY ATTACHED TO A CHAMBER HOUSING OF THE ELECTROSTATIC APPLICATOR SYSTEM
3210

↓

ADVANCING, BY THE MOTOR URGING A PLUNGER OF THE SYRINGE, FLUID CONTENTS OF THE DISPOSABLE CARTRIDGE FROM THE SYRINGE THROUGH THE DELIVERY TUBE
3220

↓

ELECTROSTATICALLY CHARGING, BY THE VOLTAGE WIRE, THE FLUID CONTENTS WHILE IN THE DELIVERY TUBE
3230

↓

EMITTING THE ELECTROSTATICALLY CHARGED FLUID CONTENTS FROM A NOZZLE ASSEMBLY OF THE DISPOSABLE CARTRIDGE ONTO A TREATMENT SITE
3240

*FIG. 32*

DISPOSABLE CARTRIDGES FOR ELECTROSPRAYING APPLICATORS, SYSTEMS, AND METHODS THEREOF

CROSS-REFERENCE TO RELATED APPLICATION

This application claims priority to and benefit under 35 U.S.0 § 119(e) of U.S. Provisional Patent Application Ser. No. 63/411,334, filed Sep. 29, 2022 which is hereby incorporated by reference in its entirety as if fully set forth below.

FIELD

The solution of this disclosure relates to devices, systems, and methods for applying one or more medicaments (e.g., one or more biologics, polymer spun wound dressing, antiseptics, or anesthetic) to a treatment site (e.g., a wound surface of subject). More specifically, the devices, systems, and methods are directed towards electrostatic applicator devices with a disposable cartridge for housing a variety of solutions.

BACKGROUND

Infectious disease is too often acquired in places that should be safe, such as ambulances, hospitals, clinical settings, and other areas such as assisted living facilities. Indeed, these health care associated infections (HAI) pose a major threat to patient safety and cause an unnecessary financial burden. Surgical site infections, for example, which are a large contributor to HAIs, can create pain and discomfort for a patient but also can contribute to longer and/or repeat hospital admissions. Numerous antibacterial and/or analgesic compounds are available to help treat the patient and avoid infections; however, despite the prevalence of these compounds, current delivery methods can often be less than efficacious.

Oral and intravenous administration, for example, are often insufficient to effectively control severe pain at or treat a specific region of the human body, and giving a high concentration dose may lead to adverse events. To overcome some of the issues related to oral and intravenous administration, delivery vehicles such as hydrogels have been developed to provide spatial and temporal control over the release of various therapeutic agents, including small molecule drugs, peptides, and cells. However, hydrogels can also have certain undesirable characteristics, including being expensive and difficult to sterilize.

More recently, electrospraying has emerged as a technology with potential biomedical applications. Electrospraying includes providing an electrostatic charge to a fluid as the fluid is expelled from an electrostatic sprayer. The electric field can cause the expelled liquid to break up into diminutive droplets, e.g., on the order of microns, which can bind to a treatment site relatively evenly and less solution. That said, not all solutions, including antiseptics and/or analgesics, respond equally to the same electrostatic conditions— differences in the viscosity and/or dielectric properties of the solution can require different optimal configurations for an electrostatic sprayer device. Current electrostatic sprayer devices do not provide modular systems that can account for various types of different solutions within one electrostatic sprayer device.

This disclosure resolves these and other issues of the art.

SUMMARY

The subject of this disclosure is an electrostatic applicator for emitting contents from a disposable cartridge (e.g., treatment solution contained in the cartridge) to a treatment site of a patient.

In some examples, a disposable fluid delivery system for an electrostatic applicator is disclosed. The system can include a nozzle housing including an air supply port, a voltage port, and a delivery outlet. A voltage wire can include a contact in communication with a delivery tube in fluid communication with the delivery outlet, the voltage wire configured to be in electrical communication with a high voltage module and electrostatically charge fluid contents within the delivery tube. A syringe can include a barrel portion, and a plunger configured to advance fluids from within the barrel portion and through the delivery tube. A cartridge housing can at least partially encloses the nozzle housing, the voltage wire, and the syringe.

In some examples, a voltage tube is in electrical communication with the voltage port, wherein the voltage wire runs between the contact in communication with the delivery tube and a contact port of a wall of the cartridge housing.

In some examples, the voltage tube and the voltage wire include a substantially S-shape.

In some examples, the voltage tube and the voltage wire include a substantially curved shape.

In some examples, the voltage tube and the voltage wire include a linear shape.

In some examples, the syringe contains the fluid including one or more of an antiseptic, a disinfectant solution, an analgesic, an exosome, a biologic, and/or a liquid bandage solution.

In some examples, the analgesic includes one or more of lidocaine, levobupivacaine, acemetacin, ketorolac, and ceftazidime.

In some examples, the biologic includes one or more of stem cells and/or mammalian cells.

In some examples, the cartridge housing is a moldable plastic material.

In some examples, the cartridge housing includes a plurality of sections of moldable plastic connectable to create a single integrated component.

In some examples, the contact of the voltage wire includes a wire loop at least partially surrounding an outer surface of the delivery tube to provide a voltage potential of approximately 1 V to approximately 40 kV.

In some examples, the contact of the voltage wire is in physical contact with an outer surface of the delivery tube to provide a voltage potential of approximately 1 V to approximately 40 kV.

In some examples, the delivery tube, when assembled with the syringe and the nozzle housing, is configured to receive air from the air supply port and fluid from the barrel portion of the syringe and expel fluid equally charged by the voltage wire.

In some examples, the disposable cartridge comprises an air supply tube connected to the air supply port.

In some examples, the system includes a reusable electrostatic applicator including a cartridge chamber sized and shaped to accept the cartridge housing, the reusable electrostatic applicator including a high voltage module configured to be in in electrical communication with the voltage wire. A piston can be positioned proximate the cartridge chamber and configured to advance the plunger enclosed in the cartridge housing when the cartridge housing is assembled with the cartridge chamber.

In some examples, the reusable electrostatic applicator includes a motor configured to move the piston, one or more processors, and memory storing instructions that, when executed by the one or more processors, causes the reusable electrostatic applicator to receive an activation signal, output a control signal to the motor to actuate the piston, and output a control signal to a switch to provide voltage from the high voltage module to the voltage wire.

In some examples, the motor is a stepper motor, a linear actuator, worm gear motor, and/or a planetary gear motor.

In some examples, the motor is a drivable actuator system using a kinetic transfer with applied force.

In some examples, the reusable electrostatic applicator includes a display screen, and the activation signal is a user input into the display screen.

In some examples, the reusable electrostatic applicator further includes an actuator, and the activation signal is user input received by the actuator.

In some examples, the reusable electrostatic applicator includes a housing base including a voltage source, a device housing including the cartridge chamber; and a handle extending between the housing base and the device housing.

In some examples, the cartridge chamber is positioned within the device housing such that the actuator is positioned below the cartridge chamber with respect to horizontal.

In some examples, the reusable electrostatic applicator includes a wireless antenna, and the activation signal is a wireless signal received from a remote external user device.

In some examples, an electrostatic applicator system is disclosed for delivering a treatment solution to a target site. The system can include a portable reusable electrostatic applicator including a device housing configured to be handheld, a motor in the device housing configured to drive a piston, a voltage source in the device housing, a high voltage module electrically connected to the voltage source, and a cartridge chamber. A disposable cartridge is removably insertable in the cartridge chamber, the disposable cartridge including a nozzle housing including an air supply port, a voltage port, and a delivery outlet. A voltage wire is provided with a contact in communication with a delivery tube in fluid communication with the delivery outlet. A syringe is provided with a barrel portion and a plunger configured to distally advance fluids from within the barrel portion and through a delivery tube. A cartridge housing is included at least partially enclosing the nozzle housing, the voltage wire, and the syringe.

In some examples, the voltage wire and a voltage tube include the voltage wire in the cartridge housing includes a linear shape and/or a curved shape or a substantially S-shape.

In some examples, the cartridge housing is a moldable plastic material.

In some examples, the cartridge housing includes a plurality of connected sections of moldable plastic.

In some examples, the cartridge chamber includes a wall including a high voltage contact in electrical communication with the high voltage module and an air supply port in fluid communication with a pump positioned in the device housing. The voltage wire can be in electrical communication with the high voltage contact of the wall. The contact of the voltage wire can be in physical contact with an outer surface of the delivery tube to provide a voltage potential of approximately 1 V to approximately 40 kV.

In some examples, the delivery tube, when assembled with the syringe the nozzle housing, is configured to receive air from the air supply port and fluid from the barrel portion of the syringe and expel fluid equally charged by the voltage wire.

In some examples, the device housing includes a handle and the voltage source is disposed within a housing base of the device housing, and wherein the handle is disposed between the device housing and the housing base.

In some examples, the reusable electrostatic applicator includes, one or more processors, and memory storing instructions that, when executed by the one or more processors, causes the reusable electrostatic applicator to receive an activation signal, output a control signal to a motor controlling (a) a voltage potential from the high voltage module to the delivery tube via the voltage wire, (b) a position of the piston and the plunger of the disposable cartridge, and/or (c) a pump regulating air flow from the device housing into the air supply port via the air supply tube.

In some examples, the disposable cartridge includes an integrated memory including information related to operational parameters of contents stored within the syringe and/or another fluid reservoir of the disposable cartridge, wherein the one or more processors of the reusable electrostatic applicator are configured to communicate with the integrated memory to retrieve information related to the contents of the disposable cartridge and control at least one of a flow rate, a voltage potential, and a nozzle setting.

In some examples, the disposable cartridge includes an integrated memory including information related to operational parameters of contents stored within the syringe and/or another fluid reservoir of the disposable cartridge. The one or more processors of the reusable electrostatic applicator are configured to communicate with the integrated memory to retrieve information related to the contents of the disposable cartridge and control a motor speed, an intake of air, and/or an applied voltage.

In some examples, the memory is embedded in a processor of the electrostatic applicator system and includes operation instructions for operating the electrostatic applicator system.

In some examples, a near field communication (NFC) tag includes the memory.

In some examples, the instructions further include reading information of the NFC related to operational parameters of the disposable cartridge; and presenting at least some of the read information of the NFC in the display screen (e.g., information such as identification of the contents, volume, etc.). In some aspects, information can be written to the NFC by the processor of the electrostatic applicator system.

In some examples, the applicator includes a display screen, and wherein the activation signal is a user input into the display screen.

In some examples, the applicator includes an actuator, and the activation signal is user input received by the actuator.

In some examples, the applicator includes a communication system within a CPU of the applicator. The communication system can include a wireless antenna (e.g., one or more transceivers can be compatible with short range wireless communication connections), and the activation signal is a wireless signal received from an external user device.

In some examples, the applicator includes an accelerometer configured to output a movement signal to the one or more processors in response to detecting movement of the electrostatic applicator system.

In some examples, the applicator includes a display screen on the electrostatic applicator system activated by a wake signal from the one or more processors in response to the one or more processors receiving the movement signal, and the activation signal is a user input into the display screen.

In some examples, the electrostatic applicator system further includes a proximity sensor configured to detect a distance between the system and an intended target. One of the control signals is output to the motor in response to the distance being within a predetermined distance threshold. In some examples, the predetermined distance threshold can be between approximately 2 inches and approximately 18 inches but most preferably between approximately 4 inches and approximately 6 inches. One of the control signals is output to a switch to control voltage of the electrostatic applicator system in response to the distance being within the predetermined distance threshold.

In some examples, the electrostatic applicator system further includes a proximity sensor configured to detect a distance between the system and an intended target, wherein one of the control signals is output to prevent operations of the motor in response to the distance being greater than or less than a predetermined distance threshold.

In some examples, the electrostatic applicator system further includes a proximity sensor configured to detect a distance between the system and an intended target, wherein one of the control signals is output to a switch to prevent delivery of voltage of the electrostatic applicator system in response to the distance being greater than or less than a predetermined distance threshold.

In some examples, a method for operating an electrostatic applicator system is disclosed. The method can include inserting a first disposable cartridge into a chamber housing of the electrostatic applicator system such that a voltage contact at a first end of a voltage wire within the first disposable cartridge contacts a voltage contact of the electrostatic applicator system; a first end of an air supply port within the first disposable cartridge fluidly connects with an air supply port of the electrostatic applicator system; and a plunger of a syringe within the first disposable cartridge aligns with a piston of the electrostatic applicator system, the syringe containing a first fluid. The method can include causing, by an activation input to the electrostatic applicator system, a motor to actuate and a voltage potential to be delivered to a delivery tube of the first disposable cartridge.

In some examples, actuating the motor and delivering the voltage potential causes the first fluid to advance from the syringe through the delivery tube and be sprayed as atomized electrostatically charged fluid droplets in a predetermined spray pattern onto a target site. In some aspects, the target site may be oppositely charged with respect to the droplets. In some aspects, a greatest voltage potential path may be between the target site and the charged droplets, though the target site may not specifically be oppositely charged.

In some examples, actuating the motor and delivering the voltage potential causes the first fluid to advance from the syringe through the delivery tube and be sprayed as atomized electrostatically charged fluid droplets carrying in a predetermined spray pattern onto an oppositely charged target site.

In some examples, the method can include removing the first disposable cartridge from the chamber housing; and inserting a second disposable cartridge into the chamber housing, wherein the second disposable cartridge contains a second fluid.

In some examples, the second disposable cartridge is configured for electrospinning. The method can include causing, by a second activation input to the electrostatic applicator system, a motor to actuate and a voltage potential delivered to a delivery tube of the second disposable cartridge so that the second fluid of a syringe of the second disposable cartridge is delivered by a delivery tube of the second disposable cartridge as an electrospun fiber from the second fluid (e.g., at a predetermined rate and/or an emission pattern) to a target site. In some examples, the second fluid can have fiber suspended in it before the electrospun fiber is formed.

In some examples, the first disposable cartridge and the second disposable cartridge each include an integrated memory including information related to operational parameters of the first fluid and the second fluid, respectively, and wherein inserting either the first disposable cartridge or the second disposable cartridge into the chamber housing causes the operational parameters to be transmitted to a memory of electrostatic applicator system, the operational parameters including a speed of the motor, an air intake, and a voltage applied to the delivery tube of the respective disposable cartridge.

In some examples, the method can include upon inserting one of the first disposable cartridge or the second disposable cartridge of the chamber housing, tagging a registry associated with information of the operational parameters of the first disposable cartridge or the second disposable cartridge as being a used cartridge; and upon determining the first disposable cartridge or the second disposable cartridge is a used cartridge, preventing the motor from actuating and/or a voltage potential to be delivered to the delivery tube of the first disposable cartridge or the second disposable cartridge In some examples, the first disposable cartridge and the second disposable cartridge contain different fluids.

In some examples, the first disposable cartridge and the second disposable cartridge include at least one of a different voltage wire and a different delivery tube depending on a respective nozzle housing, the first fluid, and/or the second fluid stored within the respective disposable cartridge.

In some examples, providing an activation input includes inputting information related to the first fluid into a display screen on the electrostatic applicator system and providing an input into the display screen.

In some examples, the method includes pairing, via a short-range wireless connection, the electrostatic applicator system to an external user device, wherein providing an activation input includes inputting information related to the first fluid into the external user device and providing an input into a display screen of the external user device.

In some examples, a computer-implemented method for operating an electrostatic applicator system is disclosed. The method includes causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a chamber housing of the electrostatic applicator system; advancing, by the motor urging a plunger of the syringe, fluid contents of the disposable cartridge from the syringe through the delivery tube; electrostatically charging, by the voltage wire, the fluid contents in the delivery tube; and emitting the electrostatically charged fluid contents from a nozzle assembly of the disposable cartridge onto a treatment site.

In some examples, the method can include electrostatically charging, by the voltage wire, the fluid contents in a barrel portion of the syringe proximal of the delivery tube.

In some examples, the step of emitting the electrostatically charged fluid contents from the nozzle assembly includes controlling air intake from an air supply of electrostatic applicator system into the disposable cartridge so as to atomize the electrostatically charged fluid contents into droplets in a predetermined spray pattern onto a target site.

In some examples, the step of emitting the electrostatically charged fluid contents from the nozzle assembly includes being delivered as an electrospun fiber from the electrostatically charged fluid contents.

In some examples, the method includes detecting, by a proximity sensor, a distance between the electrostatic applicator system and an intended target; and in response to the distance being within a predetermined distance threshold, causing the activation input to be transmitted to actuate the motor and/or the high voltage module to deliver the voltage potential.

In some examples, the method includes detecting, by a proximity sensor, a distance between the electrostatic applicator system and an intended target; and in response to the distance being greater than or less than a predetermined distance threshold, preventing actuation of the motor and/or preventing the high voltage module from delivering the voltage potential.

In some examples, the method includes activating, by a display screen on the electrostatic applicator system, a wake signal from one or more processors of the electrostatic applicator system in response to the one or more processors receiving a movement signal; and in response to the wake signal, causing the activation input to be transmitted to actuate the motor and/or the high voltage module to deliver the voltage potential.

In some examples, the disposable cartridge includes an integrated memory including information related to operational parameters of fluid contents stored within the syringe. In this respect, the method can include communicating, by one or more processors of the reusable electrostatic applicator, with the integrated memory to retrieve information related to the fluid contents of the disposable cartridge; and controlling at least one of a flow rate, a voltage potential, and a nozzle setting, so as to control one or more operational parameters of the disposable cartridge, the one or more operational parameters including a motor speed, an intake of air, and/or an applied voltage of the disposable cartridge.

In some examples, memory is embedded in a processor of the electrostatic applicator system and includes operation instructions for the computer-implemented method for operating the electrostatic applicator system.

In some examples, a system is disclosed for operating an electrostatic applicator system. The system can include at least one memory storing instructions and at least one processor configured to execute the instructions to perform operations. In some aspects, the operations can include causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a chamber housing of the electrostatic applicator system; advancing, by the motor urging a plunger of the syringe, fluid contents of the disposable cartridge from the syringe through the delivery tube; electrostatically charging, by the voltage wire, the fluid contents while in the delivery tube; and emitting the electrostatically charged fluid contents from a nozzle assembly of the disposable cartridge onto a treatment site.

In some examples, the step of emitting the electrostatically charged fluid contents from the nozzle assembly includes controlling air intake from an air pump within the electrostatic applicator into the disposable cartridge so as to atomize the electrostatically charged fluid contents into droplets in a predetermined spray pattern onto an oppositely charged target site.

In some examples, the step of emitting the electrostatically charged fluid contents from the nozzle assembly includes being delivered as an electrospun fiber from the electrostatically charged fluid contents at a predetermined rate and/or a pattern onto a target site with a voltage potential differential.

In some examples, the operations include detecting, by a proximity sensor, a distance between the electrostatic applicator system and an intended target; and in response to the distance being within a predetermined distance threshold, causing the activation input to be transmitted to actuate the motor and/or the high voltage module to deliver the voltage potential.

In some examples, the operations include activating, by a display screen on the electrostatic applicator system, a wake signal from one or more processors of the electrostatic applicator system in response to the one or more processors receiving a movement signal; and in response to the wake signal, causing the activation input to be transmitted to actuate the motor and/or the high voltage module to deliver the voltage potential.

In some examples, the disposable cartridge includes an integrated memory including information related to operational parameters of fluid contents stored within the syringe. The operations in this respect can include communicating, by one or more processors of the reusable electrostatic applicator, with the integrated memory to retrieve information related to the fluid contents of the disposable cartridge; and controlling at least one of a flow rate, a voltage potential, and a nozzle setting, so as to control the one or more operational parameters of the disposable cartridge, the one or more operational parameters including a motor speed, an intake of air, and/or an applied voltage of the disposable cartridge.

In some examples, memory is embedded in a processor of the electrostatic applicator system and includes operation instructions for the computer-implemented method for operating the electrostatic applicator system.

In some examples, a non-transitory computer-readable medium is disclosed storing instructions that, when executed by processor, cause the processor to perform a method for operating an electrostatic applicator system. The method can include causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a chamber housing of the electrostatic applicator system; advancing, by the motor urging a plunger of the syringe, fluid contents of the disposable cartridge from the syringe through the delivery tube; electrostatically charging, by the voltage wire, the fluid contents while in the delivery tube; and emitting the electrostatically charged fluid contents from a nozzle assembly of the disposable cartridge onto a treatment site.

In some examples, the step of emitting the electrostatically charged fluid contents from the nozzle assembly includes controlling air intake from an air supply of electrostatic applicator system into the disposable cartridge so as to atomize the electrostatically charged fluid contents into droplets in a predetermined spray pattern onto an oppositely charged target site. In some examples, the predetermined spray pattern can include the droplets being similarly charged and being repelled from other of the droplets while being drawn towards the oppositely charged target site. In some examples, the droplets can be positively charged while the target site can be negatively charged. In some examples, the droplets can be negatively charged while the target site can be positively charged.

In some examples, the step of emitting the electrostatically charged fluid contents from the nozzle assembly includes being delivered as an electrospun fiber from the electrostatically charged fluid contents at a predetermined rate and/or a pattern onto an oppositely charged target site.

In some examples, the method includes detecting, by a proximity sensor, a distance between the electrostatic applicator system and an intended target; and in response to the distance being within a predetermined distance threshold, causing the activation input to be transmitted to actuate the motor and/or the high voltage module to deliver the voltage potential.

In some examples, the method includes activating, by a display screen on the electrostatic applicator system, a wake signal from one or more processors of the electrostatic applicator system in response to the one or more processors receiving a movement signal; and in response to the wake signal, causing the activation input to be transmitted to actuate the motor and/or the high voltage module to deliver the voltage potential.

In some examples, the disposable cartridge includes an integrated memory including information related to one or more operational parameters of fluid contents stored within the syringe. The method can include communicating, by one or more processors of the reusable electrostatic applicator, with the integrated memory to retrieve information related to the fluid contents of the disposable cartridge; and control at least one of a flow rate, a voltage potential, and a nozzle setting, so as to control the one or more operational parameters of the disposable cartridge, the one or more operational parameters including a motor speed, an intake of air, and/or an applied voltage of the disposable cartridge.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 31 is a flow diagram for operating an example electrostatic applicator system according to the present disclosure.

FIG. 32 is a flow diagram for a computer-implemented method for operating any electrostatic applicator system of this disclosure.

DETAILED DESCRIPTION

Figure 1A:
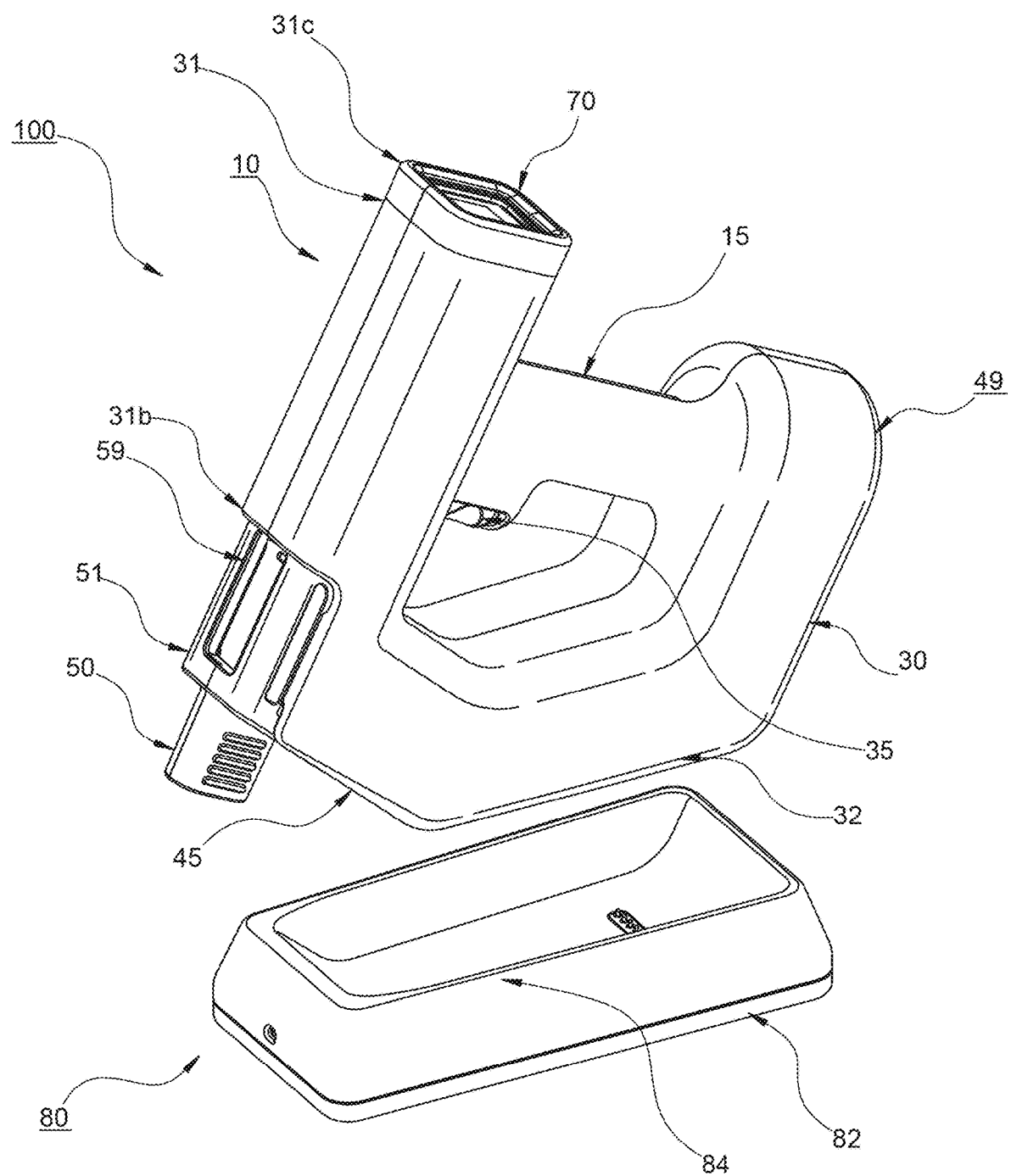
FIG. 1A depicts a perspective view of an example electrostatic applicator positioned in an exploded state with an example base.
Figure 1B:
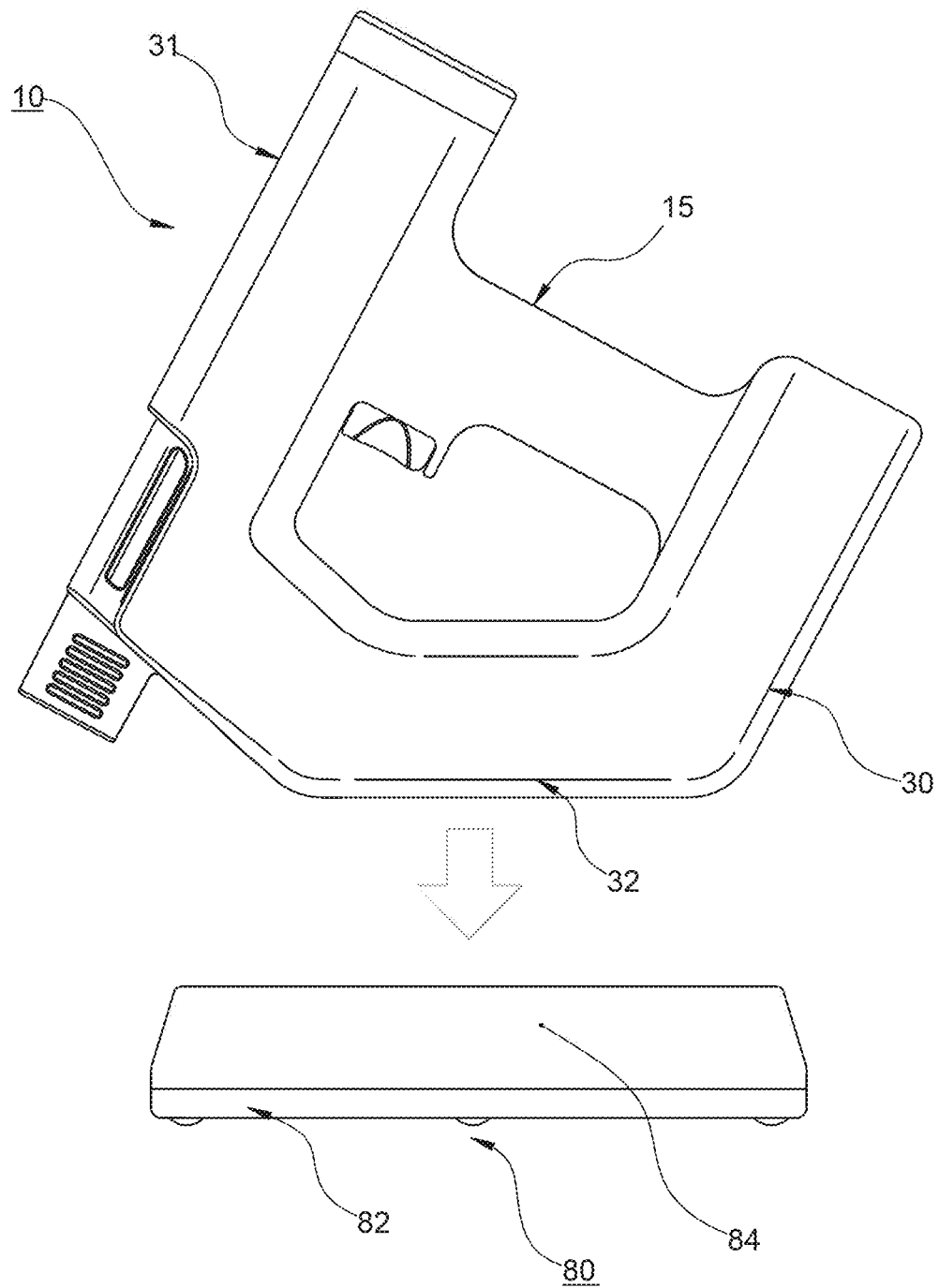
FIG. 1B depicts a side view of the example electrostatic applicator of FIG. 1A positioned in an exploded state with the example base.
Figure 1C:
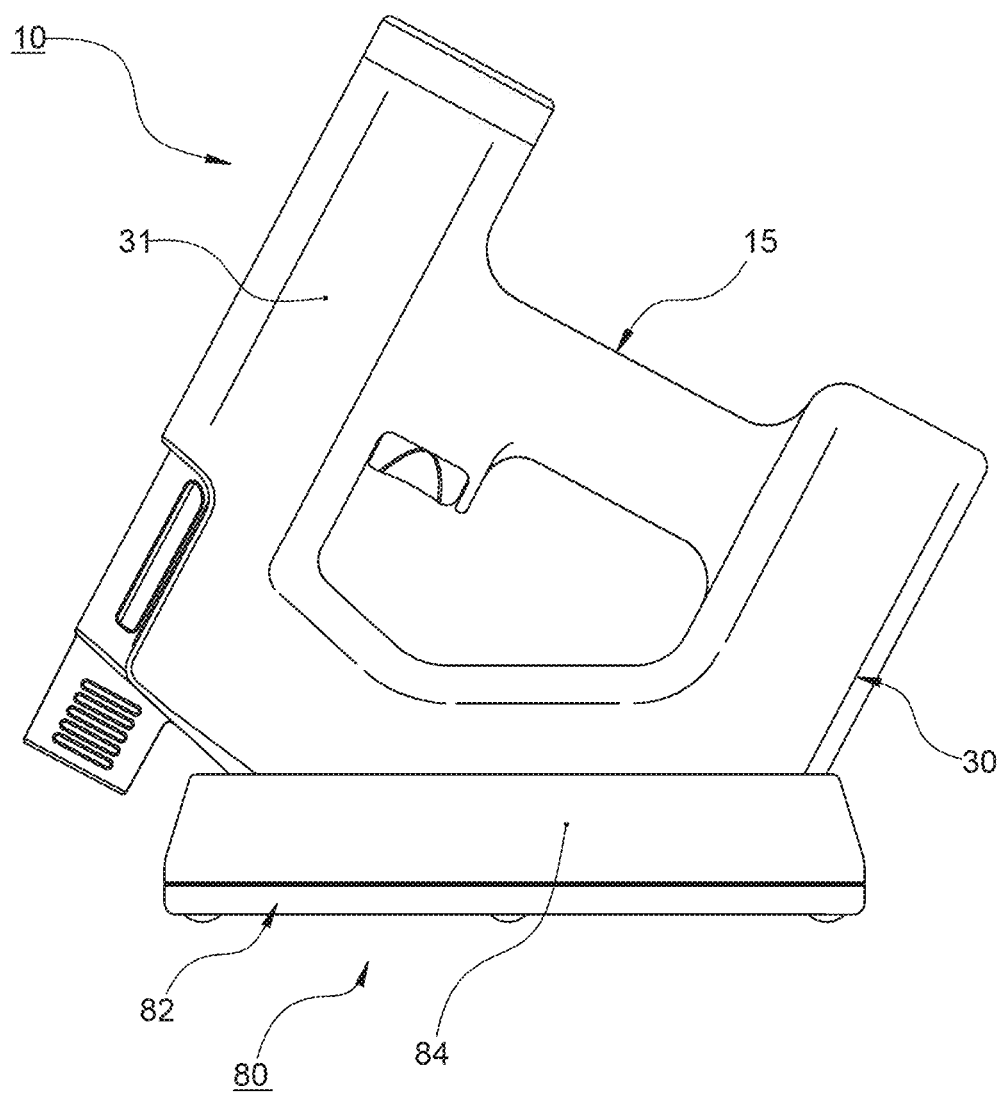
FIG. 1C depicts a side view of the example electrostatic applicator of FIG. 1A positioned in an assembled state with the example base.
Figure 2A:
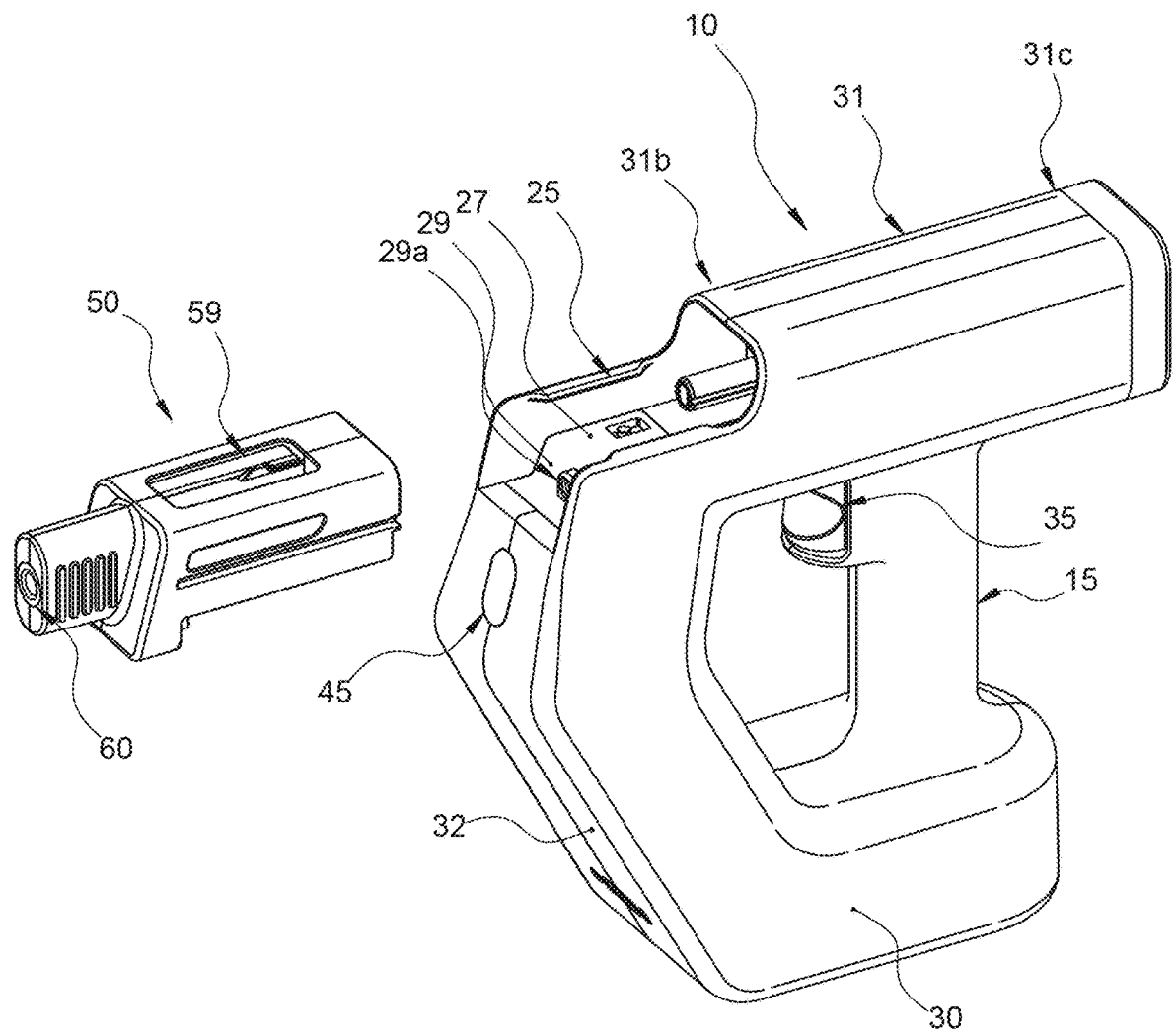
FIG. 2A depicts a perspective view of the example electrostatic applicator of FIGS. 1A-1C with a disposable cartridge in an exploded state.
Figure 2B:
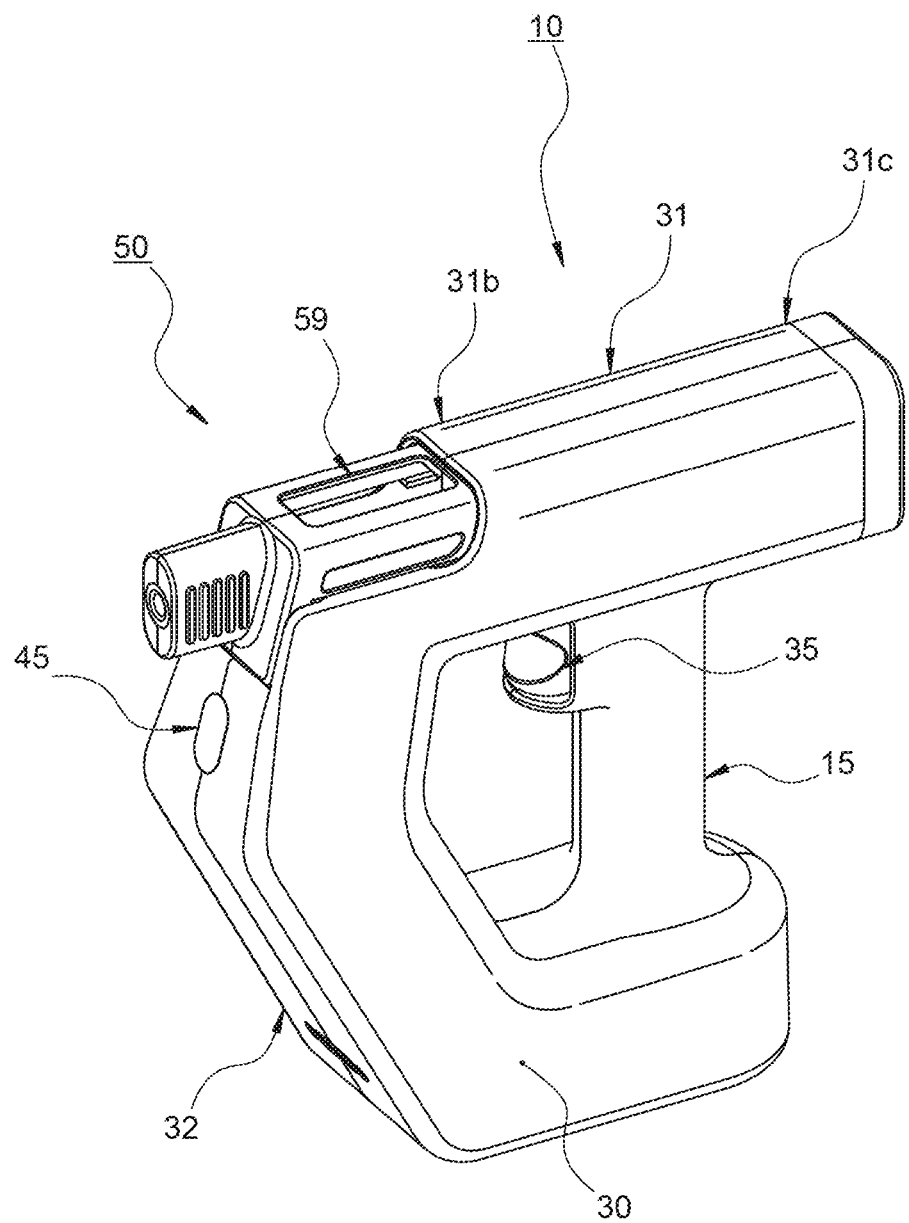
FIG. 2B depicts a perspective view of the example electrostatic applicator of FIGS. 1A-1C with the disposable cartridge of FIG. 2A in the exploded state.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In this disclosure, relative terms, such as "about," "substantially," or "approximately" are used to indicate a possible variation of ±10% in the stated value.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a treatment site of a "subject" or "patient" may be a wound site or treatment of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include, but is not limited to, a doctor, surgeon, nurse, physical therapist, or other healthcare professional, or any other suitable individual, or delivery instrumentation associated with the application of a treatment solution of a treatment site of a subject.

As discussed herein, "treatment solution" may be one or more fluids (e.g., liquid and/or emulsion solution, gels, and/or mixtures) and may include one or more of an antiseptic solution, a disinfectant solution, an analgesic, an exosome, a biologic, chlorohexidine gluconate, povidone-iodine, and/or a liquid bandage solution. The analgesic can include one or more of lidocaine, levobupivacaine, acemetacin, ketorolac, and ceftazidime. The biologic can include one or more of stem cells and/or mammalian primary cells, medicaments, gels (e.g., hydrogels), reconstitutable aspects (e.g., immiscible and/or lyophilized ingredients mixable with one or more solvents). The disinfectant can include one or more alcohols, aldehydes, oxidatives, phenols, quaternary ammonium compounds, etc., antibacterial agents, biguanides, analgesic agents, surfactant agents, and/or debridement components or any other contents and/or medication contemplated for storage in a cartridge of this disclosure that can be delivered (e.g., applied, deposited, and/or sprayed by an electrostatic applicator) to a treatment site of a patient. The treatment solution can include any concentration or mixture of herein disclosed ingredients.

The term "treatment solution" can also include one or more tracking materials (e.g., gels with tracking aspects, intermixed with the treatment solution). The treatment solution can include any number of small molecule drugs, peptides, cells, and other therapeutics. In some aspects, the treatment solution can include one or more active pharmaceutical ingredients, growth factors, trophic factors, exosomes, mammalian regenerative cells, and/or a supportive matrix. In some aspects, the treatment solution can include lidocaine, levobupivacaine, acemetacin, ketorolac, and or the like or any combination thereof.

The terms "distal" or "proximal" are used in the following description with respect to a position or direction relative to a reference point (e.g., such as a user [e.g., the treating physician or medical interventionalist]). "Distal" or "distally" are a position distant from or in a direction away from the reference point. "Proximal" or "proximally" or "proximate" are a position near or in a direction toward the reference point.

An increasing amount of care and resources has been focused on creating effective treatments for pain and infection care. The most common method of treating pain and infection includes oral and intravenous (IV) administration of drugs. Although these methods are prevalent, oftentimes the efficacy of the drug delivery method is lacking. For example, when drugs are administered orally or via IV methods, their treatment effect is generalized and not localized—the drug targets the entire patient instead of a localized treatment site. To overcome some of these issues, delivery vehicles such as topical treatments and, more particularly, hydrogel compounds have been developed to provide spatial and temporal control over the release of various therapeutic agents, including small molecule drugs, peptides, and cells. However, these treatments can also have drawbacks. These often synthetic carriers of therapeutics can be costly and, since they are fragile polymer chains, it can be difficult to sterilize polymer chains of the solution/hydrogel combination.

More recently, the concept of electrospraying treatment solutions, including antibacterial and/or analgesic solutions, to treatment sites has been considered. Electrostatic spraying is a technique that subjects a treatment solution to an electric field to charge the fluid. The electric field, provided by a voltage source, can create a charge to the fluid being administered (e.g., a positive charge or a negative charge). This is particularly helpful in the biomedical arena since the natural resting state of human cells is negative (i.e., a state of negative charge). This imbalance is created by potassium and sodium ions inside and outside the cell that establishes electrical capacity in a patient's body. This polarity differential creates a natural attraction between the treatment site and the solution being sprayed.

However, the negative/positive attraction is not the only benefit of electrostatic spraying. For example, subjecting the fluid to this electrical field can also produce diminutive droplets (e.g., micron sizes), providing a relatively uniformly distributed layer of treatment solution. When the electrical stresses due to the charge builds in a liquid droplet beyond its surface tension, the droplet disintegrates and/or atomizes into very fine droplets—which is known as Rayleigh disintegration or coulomb fission. As discussed herein, the term "atomize" is understood as some or all of the process of converting a substantially liquid solution into very fine particles or droplets. The solvent dielectric constant or conductivity can play a crucial role in dictating particulate morphology. Other factors that affect the way a liquid atomizes include vapor pressure, viscosity and miscibility of the treatment solution, voltage applied to the solution, etc.

It is noted that prior designs for electrosprayer devices did not take these various types of parameters into consideration. This is because most prior art electrostatic device focused on spraying one type of solution—consider the common examples of ink jet sprayers, paint sprayers, etc., which sprayed consistent solutions at consistent flow rates and with consistent voltage potentials. Further, these types of applications did not focus on operating parameters. The present disclosure provides solutions that can maintain sterility for each administration of a treatment solution by providing individualized, pre-filled disposable cartridges housing the components used for electrospraying. Further, each disposable cartridge can be individually tailored and/or communicate with a reusable electrostatic applicator to individually tailor the parameters needed to administer the preferred particle (e.g., nano to microparticles) droplets for targeted treatment.

Turning to the drawings, FIG. 1A provides an example applicator 100 positioned in an exploded state with an example base 80. Applicator 100 can be used in conjunction with a disposable cartridge 50, according to the present disclosure. Applicator 100 can include an applicator housing 10 which can include an upper portion 31, a lower base portion 30 at the lower section, and a handle portion 15 between portions 30 and 31. A forward cartridge support portion 32 can also be positioned between portions 30 and 32. In some aspects, an obtuse angle can be formed between aspects of outer surfaces of portions 30 and 32 while handle portion 15 can be orthogonal to portions 30 and/or 31. And while shown as a handheld pistol shaped device, nothing requires the reusable applicator 100 to have a pistol-shaped design, as the components herein can also be combined in other electrosprayer designs, for example and not limitation a fully-cylindrical, handheld electrosprayer design.

Figure 3:
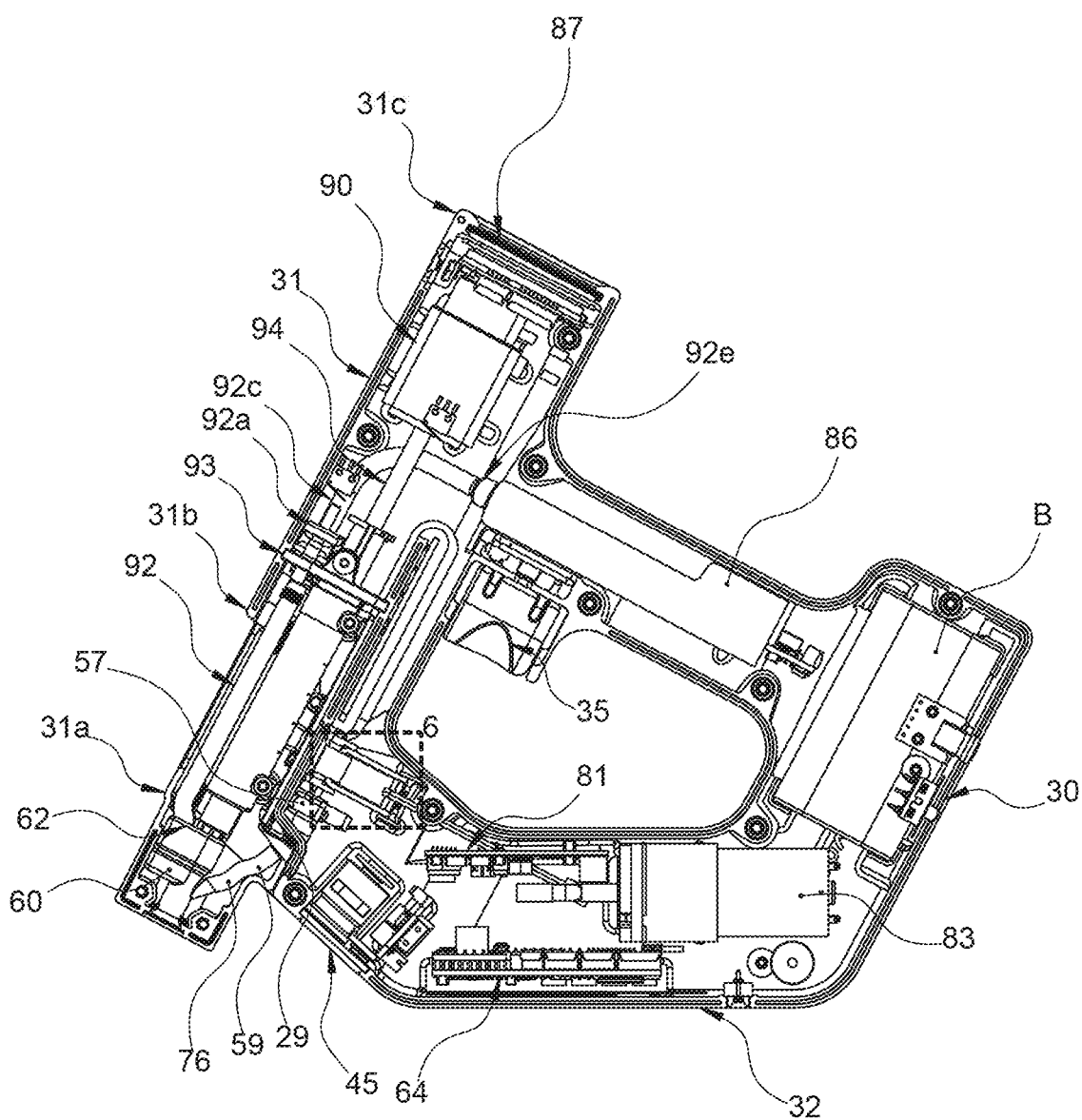
FIG. 3 depicts a side view of the example electrostatic applicator of FIG. 1A positioned with a portion of an outer housing removed.

As shown more clearly in FIG. 3, portion 30 can house a battery B that provides the voltage potential to create the electrical field at the nozzle assembly 60 of cartridge 50 and/or can power the components of applicator 100 (e.g., CPU and/or HV module 86). Battery B can include one or more batteries, including for example direct current batteries such as lithium ion batteries. Battery B can provide sufficient voltage to create the voltage potential described above, including but not limited to approximately 1 V to approximately 40 kV. In some examples, the range can be approximately 1 V to 8 kV. In some examples, the voltage supply of battery B can be one or more rechargeable batteries. In this example, aspects of the applicator 100, such as portion 32, can engage with the charging base 80 that can in turn charge the voltage supply of battery B (e.g., inductively) when the device is not in use. Portion 30 can be configured to be detached from the charging base 80 by pressing an electrostatic applicator release (not shown). In some examples, applicator 100 can include an actuator, e.g., a button 35 that can activate and/or initiate the components of applicator 100. For example, the button 35 can initiate power from battery B (see FIG. 3), which can include a rechargeable module battery such as a direct current battery. By activating and/or initiating power from battery B, the system is powered to electrostatically charge the liquid solution of the cartridge via direct charging, induction charging, indirect charging, or any combinations thereof. In the case of direct charging, liquid solution of the cartridge can flow through an electrically conductive tube or other conduit that is electrostatically charged such that the liquid solution is contacted and charged by direct contact.

In some examples, battery B can power the high voltage (HV) module 86, air pump 83, circuit board 64, target sensor 45, motor 90, user interface 87, one or more processors of applicator 100 (e.g., central processing unit (CPU)) as well as components of cartridge 50. As will be described in greater detail below, other features can be included in the applicator 100 that can obviate the need for button 35, including for example accelerometers, activation inputs from a user device, etc.

Applicator housing 10 can include a cartridge chamber 27 sized and positioned to accept the housing 49 of the disposable cartridge 50, as explained more particularly below (see FIGS. 2A-4B). Cartridge chamber 27 can include a distal stepped portion 29 through which connecting ports of internal components of housing 10 can connect to aspects of cartridge 50 (e.g., air supply ports). Although the examples shown in FIGS. 1A-1C position the cartridge chamber 27 at the top of a gun-shaped, portable, cordless, reusable applicator 100, nothing requires to the cartridge chamber 402 to be so located. For example, the cartridge chamber 27 can be positioned on the side of the applicator 100 (e.g., the side of the housing 10 of applicator 100, or any other location). In some aspects, HV module 86 can include electrical components for powering the components used for charging and spraying the liquid solution of cartridge 50. For example, HV module 86 can include the components used for providing electricity from voltage wire 92*c* through port 92*a* of cartridge 50 and to wire 92*d* so as to control the voltage applied to the liquid solution of cartridge 50, and/or for providing electricity to actuate plunger 71 (or motor 90 for operating syringe 70 including advancing plunger 71) so as to control the flow rate of liquid solution from cartridge 50 and through nozzle assembly 60.

In some aspects, HV module 86 can be configured to adjust or otherwise control operational aspects of cartridge 50 including but not limited to frequency, duty cycle, and input voltage to yield varying output voltages at different efficiencies. In some aspects, HV module 86 can be a closed loop system that monitors the output voltage and adjusts input parameters to optimize the output to a desired voltage for use with cartridge 50. HV module 86 can also be configured to produce positive and/or negative high voltage using the same board. In some aspects, HV module 86 can include a printed circuit board that is double sided so as to minimize footprint used within housing 10. Applicator 100 can include one or more processors, for example CPU, that can facilitate activation of applicator 100, receiving and outputting signals relating to the voltage, flow rate, proximity, etc. for the particular liquid treatment solution, and the like.

Within housing 10, applicator 100 can include a piston 94 and corresponding motor 90 that actuates syringe 70. Piston 94 can be positioned between motor 90 and HV wall 93. On the opposite side of HV wall 93, cartridge 50 can be positioned when attached to chamber 27 of housing 10. In some aspects, when cartridge 50 is positioned as in FIG. 3, a plunger, piston, or other aspects within a barrel of syringe 70 of cartridge 50 can be advanced by piston 94, through HV wall 93, to advance contents of cartridge 50 through nozzle assembly 60. In some aspects, motor 90 can be positioned within portion 31 adjacent a user interface 87. In some aspects, motor 90 can be a stepper motor, a worm drive motor, solenoid, and the like. The speed of motor 90 can be adjusted based on aspects such as preferred flow rate for the particular liquid solution being emitted by nozzle assembly 60 of cartridge 50.

As shown in FIG. 3, housing 10 can include a voltage wire 92*c* that contacts the voltage contact 92*e* of HV module 86 and cartridge voltage contact 92*a* of HV wall 93. Cartridge 50 electrically connects to voltage contact 92*a*, via cartridge HV contact 46 (see FIGS. 4B, 5A, 5B) when assembled in chamber 27 of housing 10. In operation, wire 92*c* provides an electrical connection between the voltage supply of high voltage module 86, which is powered by battery B. Within portion 32 of housing 20 (e.g., underneath chamber 27), an air pump 83 connects with a supply end of air supply tube 81. When cartridge 50 is assembled with chamber 27, air supply tube 81 in turn supplies air to air supply tube 76 of cartridge 50 so as to provide air for spraying charged liquid droplets. The air supply of air pump 83 can provide the high velocity air supply without the need for a separate air hose. In other embodiments, housing 10 can be connected to an external air hose that provides an air supply for spraying.

Applicator 100 can include a display screen with its user interface 87, which can include a liquid crystal (LCD) and/or a light emitting diode (LED) display. The display screen of user interface 87 can enable an operator of applicator 100 to receive information relating to the status of applicator 100, including operational parameters of cartridge 50. For example, the display screen of user interface 87 can display information related to what type of liquid solution is within disposable cartridge 50 that is connected to applicator 100. As described above, this information can be written on integrated memory of disposable cartridge 50, and a CPU of applicator 100 can receive this information and display the information to the operator of applicator 100. In some aspects, user interface 87 can display welcome animations, display whether the electrostatic applicator has connected with a user device (as will be described below), display whether applicator 100 has been properly grounded, display whether a disposable cartridge 50 has been loaded into cartridge chamber 27, and display what parameters are being used for the particular liquid solution (e.g., flow rate, voltage supply, droplet size, intended target, intended patient condition, recommended proximity, etc.).

In some examples, the display screen of user interface 87 can also have touchscreen capabilities. For example, user interface 87 can act as an actuator to initiate or otherwise control the voltage supply to the voltage wire 92*d* of cartridge 50, initiate or otherwise control air flow into air supply tube 76, and/or initiate or otherwise control the plunger 71 of syringe 70 to expel fluid from syringe 70 through nozzle assembly 60. As will be described in greater detail below, other initiation mechanisms can be used to spray the fluid, including an actuator 35 (e.g., a mechanical trigger, a switch, an actuator, and/or a graphical user interface configured to receive input from a user and perform one or more related operations) and/or signals from an external user device.

Figure 4A:
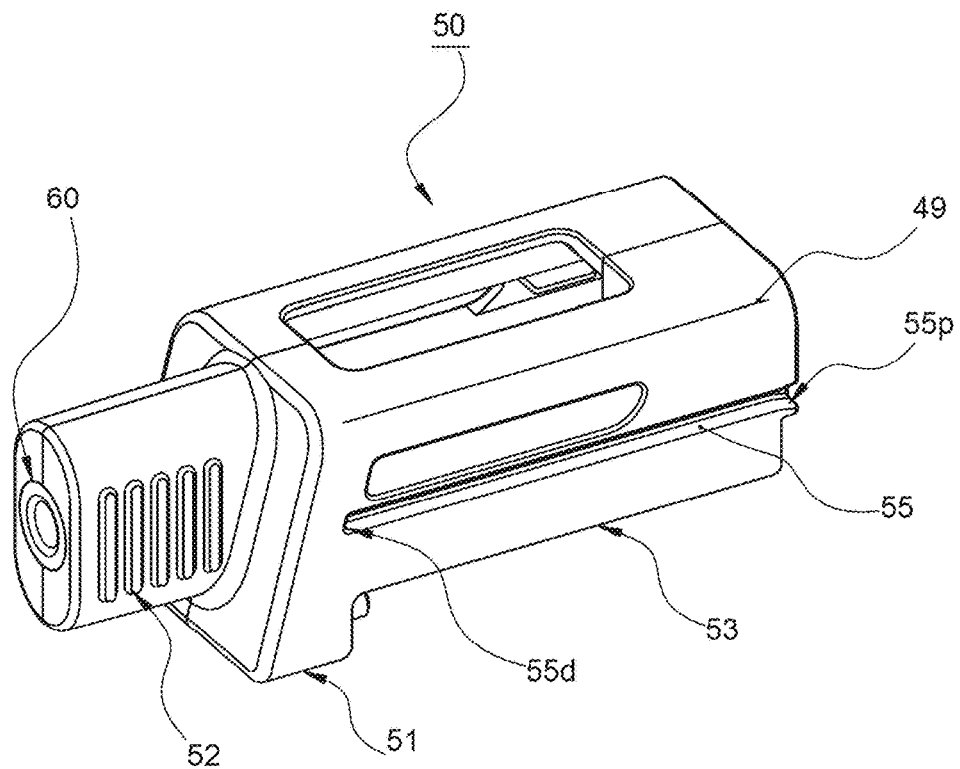
FIG. 4A depicts a forward perspective view of the example cartridge of FIGS. 1A to 2B.
Figure 4B:
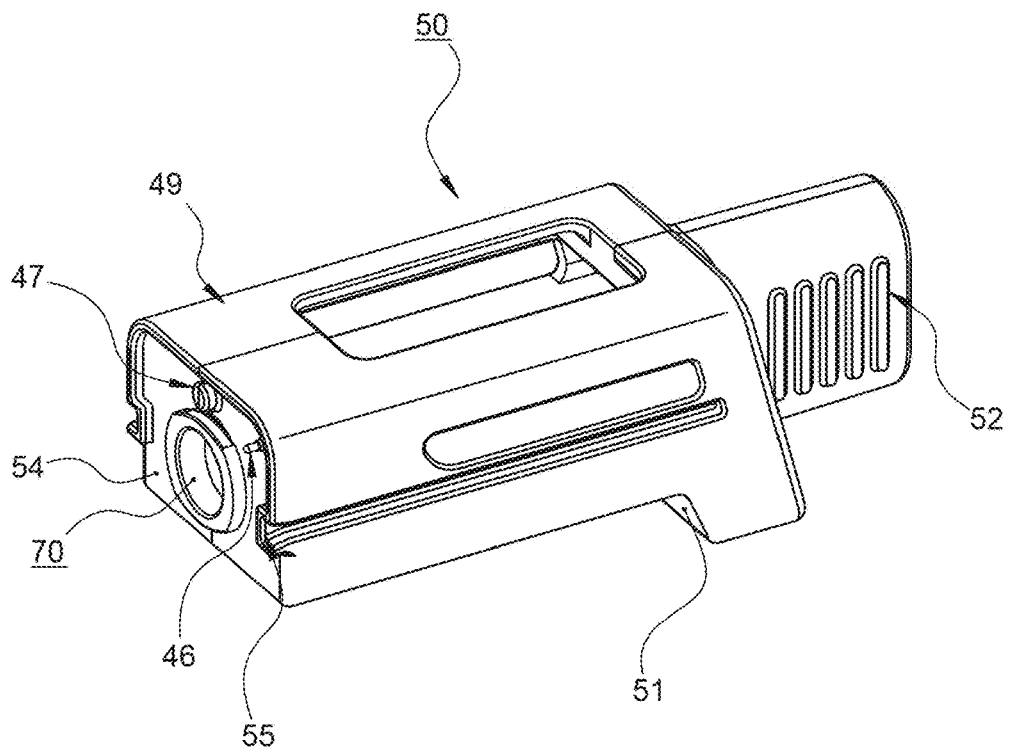
FIG. 4B depicts a rear perspective view of the example cartridge of FIGS. 1A to 2B.
Figure 5A:
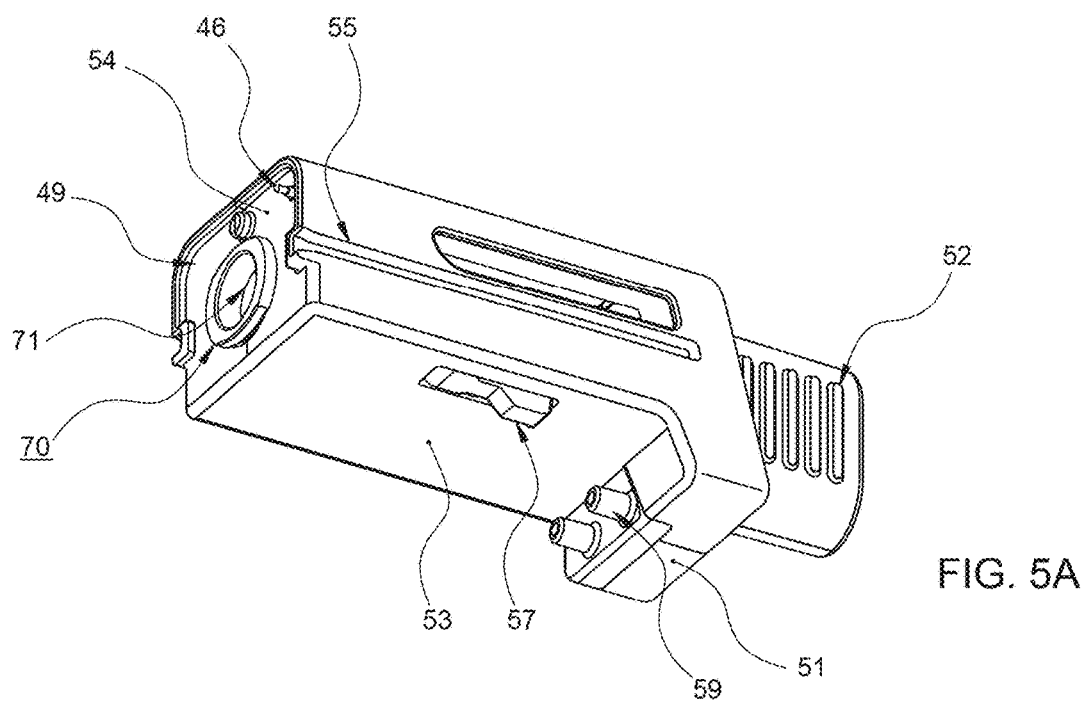
FIG. 5A depicts a lower rear perspective view of the example cartridge of FIGS. 1A to 2B.
Figure 5B:
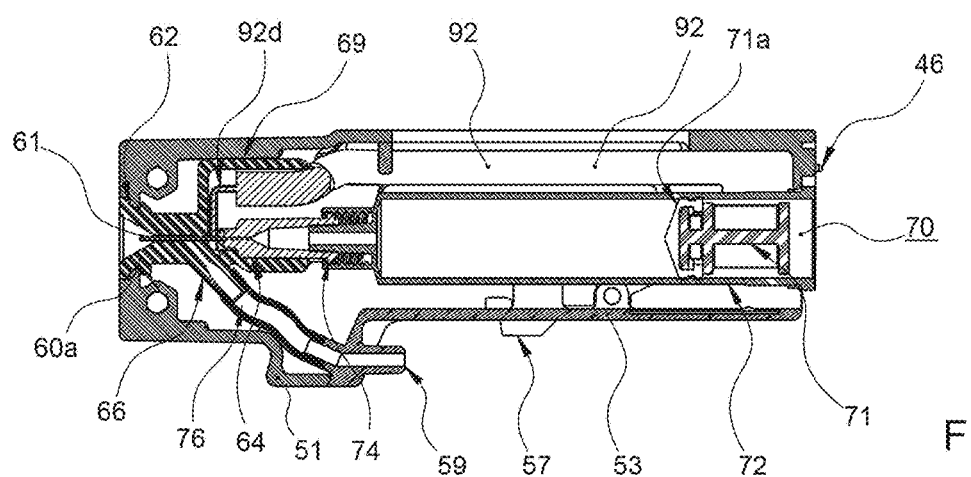
FIG. 5B depicts a side view of the example cartridge of FIGS. 1A to 2B with a portion of its outer housing removed.
Figure 5C:
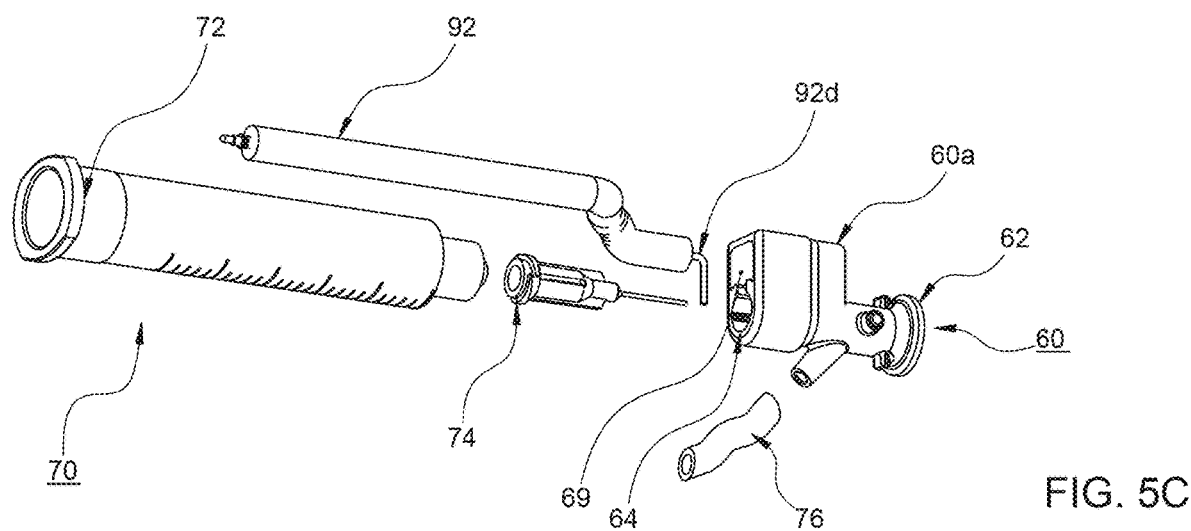
FIG. 5C depicts an exploded perspective view of internal components of example cartridge of FIGS. 1A to 2B with its outer housing removed.

Referring to FIG. 4A, a forward perspective view of cartridge 50 is provided while FIG. 4B depicts a rear perspective view of cartridge 50. Similarly, FIG. 5A depicts a lower rear perspective view of cartridge 50. FIG. 5B depicts a side view of cartridge with a portion of its outer housing 49 removed while FIG. 5C depicts an exploded perspective view of internal components of cartridge 50 with outer housing 49 removed. FIG. 5B also shows a detailed view of the nozzle housing 60*a*. It is understood that in some aspects, the entire housing 60*a* can be molded (e.g., insert molded) as a single, integrally formed part and/or formed of multiple parts or sections. The nozzle housing 60*a* can include a nozzle outlet channel 62 on a distal end that can be funnel shaped, sized and positioned to contain the outlet end of delivery tube 61. The nozzle housing 60*a* can include an air inlet port 66 in fluid communication with the nozzle end of the air supply tube 76 and inlet port 59 of cartridge 50.

The nozzle housing 60*a* can include a voltage cavity port 69 for connecting the voltage wire 92*d* and corresponding voltage tube 92 to delivery tube 61. One side of the port 69 (e.g., a distalmost end of the port 69) can include a contact section through which the wire 92*d* can pass to contact delivery tube 61. At another end of the port 69 (e.g., a proximal end of the port 69), the cavity associated with port 69 can be tubular for securing the outer surface of the voltage tube 92 in a friction fit. The nozzle outlet channel of housing 60*a* described above can be positioned at a distal end of housing 60*a* and can receive air from port 66 and fluid delivery tube 61 and expel fluid droplets that are charged by the voltage wire 92*d*. In some aspects, wire 92*d* can electrostatically charge contents within delivery tube 61 as well as fluid contents proximal thereof (e.g., contents within barrel portion 72 of syringe 70). As shown in FIGS. 5B and 5C, the voltage wire 92*d* can include one or more curved surfaces (e.g., at least one angled down curve to connect through tube 92, port 69 and in contact with delivery tube 61). Wire 92*d* can include any number of shapes, including but not limited to an S- or serpentine shape. To facilitate the shape of wire 92*d*, tube 92 can include one or more curves or bends, as shown.

Housing 49 can be formed of a multi-part shell with an aligning groove 55 that can engage with the aligning tab 25 of cartridge chamber 27. Housing 49 can be formed and/or assembled in a number of ways, including but not limited to, machining, molding, injection molding, three-dimensional printing, or any other suitable manufacturing process. Suitable materials for housing 49 may include one or more of glass filled nylon, glass filled polypropylene, glass filled polyethylene, polypropylene, polyethylene, or a plastic material. In some examples, housing 49 can include two or more sections of moldable plastic, e.g., a first half and a second half. The sections of housing 49 can be assembled together with fasteners (e.g., screws, rivets, a weld [e.g., a sonic weld], one or more straps or snaps, an adhesive or adhesive tape, etc.) such that the internal components are disposed between the portions and/or respective halves of housing 49. In some aspects, housing 49 can include a housing spray outlet associated with nozzle assembly 60 that enables charged treatment solution to be expelled from cartridge 50.

Groove 55 can engage with tab 25 to align housing into the cartridge chamber 27 with proper alignment between cartridge 50 and chamber 27. Housing 49 can include one groove 55 positioned on opposite lateral sides of cartridge 50. Groove 55 can include an open proximal end 55*p* and a closed distal end 55*d*. When end 55*d* of groove 55 is adjacent or otherwise towards nozzle assembly 60, end 55*d* prevents tab 25 from sliding deeper into groove 55. In some aspects, proximal end 55*p* can be opposite end 55*d* and may include an open, funnel or tapered shape to facilitate aligning and engagement between groove 55 and tab 25.

FIG. 4B specifically shows the supply end and contact end of cartridge 50. HV contact 46 can be a contact port embedded on HV wall 54 and/or otherwise positioned on a face of cartridge HV wall 54, which is configured to mount against HV wall 93 of housing 10. HV wall 54 can also include an air intake port 47 which can be configured to couple to a corresponding air intake port 147 of HV wall 93 (see, e.g., FIGS. 7A and 7B). As shown in FIG. 3 and FIG. 5A, cartridge 50 may also include air supply ports 59 configured to receive air supply tube 81 to place tubes 81, 76 and pump 83 in fluid communication with each other. Air supply port 59 may be positioned on the stepped portion of housing 49 which is shaped to correspondingly attach to stepped portion 29 of housing 49. The supply port 59 of the air supply tube 81 can extend at least partially from the housing 49 and be shaped to insert into an air supply port 29*a* on of applicator housing 10 at or adjacent stepped portion 29. In some aspects, air supply tube 76 of cartridge 50 and air supply tube 81 of housing 10 can include a combination of both flexible and rigid materials (e.g., nylon braiding). In some aspects, air supply tube 76 of cartridge 50 and air supply tube 81 of housing 10 can be manufactured from a pliable, fluid tight material, such as an elastomer, rubber, silicon, polyvinyl chloride, etc. In some aspects, air supply tube 76 of cartridge 50 and air supply tube 81 of housing 10 can also be can be insert-molded and/or overmolded with a combination of softer, pliable fluid tight materials and/or one or more rigid materials (e.g., metal, alloy, etc.).

Figure 6:
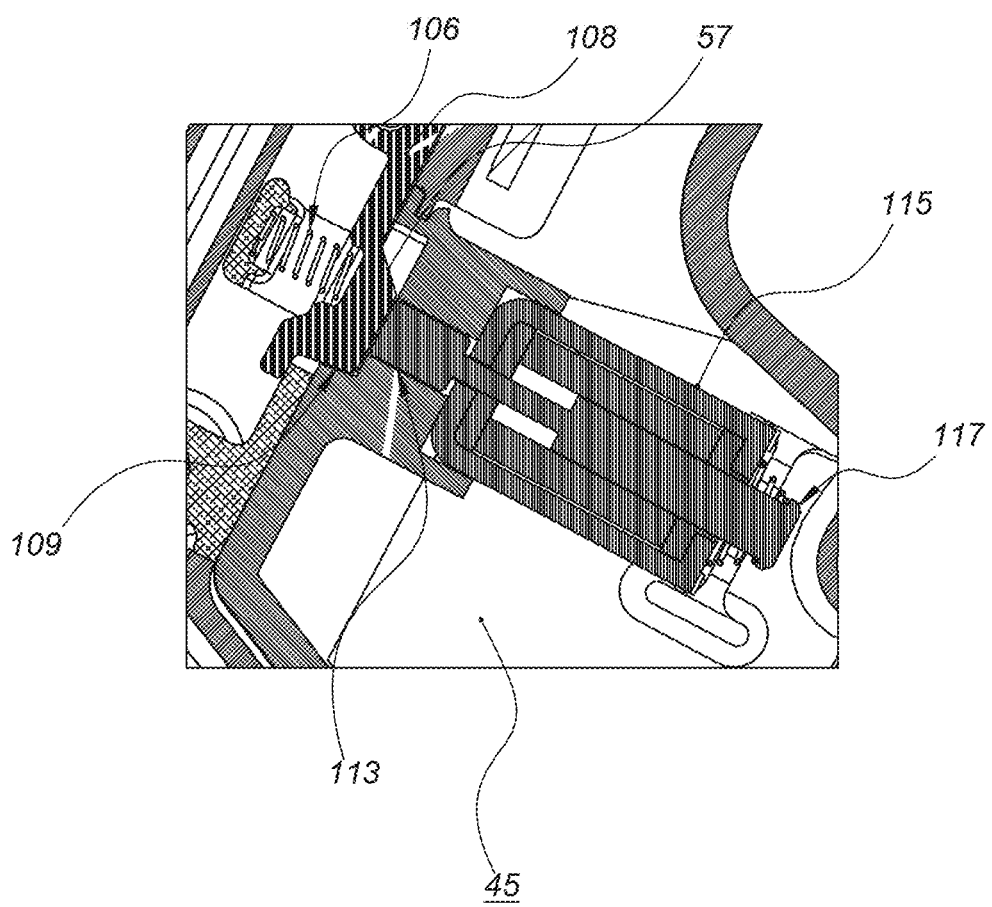
FIG. 6 depicts a close-up cross-section view of section 6 from FIG. 3 showing aspects of the example cartridge of FIGS. 1A to 3 in a closed position with the electrostatic applicator.

Once securely engaged with chamber 27, cartridge 50 can be released by a release button 57. As shown in FIG. 5A, 5B, and FIG. 6, button 57 can extend at least partially though a lower surface 53 of housing 49 via an aperture in the lower surface 53 of housing 49. Button 57 can be a latch that is connected, for example, to a portion of the syringe 70 and can be removed from cartridge 50 when cartridge 50 is ready to be attached to housing 10. This can indicate to a user that the cartridge 50 has not yet been used and that the contents therein (e.g., liquid treatment solution) has not been used. In some examples, the contents stored within syringe 70 can be sterilized, and release button 57 can indicate that the contents of disposable cartridge 50 are sterile and have not been used (e.g., not yet used on a previous patient). In some aspects, button 57 can prevent syringe 70 and any components thereof from advancing contents therein prior to use. In some aspects, button 57 can a include near field communication (NFC) tag with identifying cartridge information and other operational parameters readable therefrom indicate to a user that cartridge 50 has not yet been used and that the contents therein (e.g., liquid treatment solution) has not been used.

As also shown in FIG. 5A, 5B, and FIG. 6, cartridge 50 can contain and/or at least partially enclose, within its housing 49, the aforementioned air supply tube 76, voltage tube 92, and syringe 70. Syringe 70 can be an assembly that includes a glass or plastic syringe for storing the liquid solution that is to be applied using the disposable cartridge 50. Syringe 70 can be assembled within the disposable cartridge 50 pre-filled with the desired liquid solution. At a proximal end, syringe 70 can include movable plunger 71, a moveable stopper 71a, and a barrel portion 72 extended distally therefrom. Plunger 71 and stopper 71a are configured to advance within barrel 72 so as to advance contents of barrel portion 72 through a luer lock 74 positioned at distal end of portion 72. An inner distal delivery tube 61 can be distally extended from luer lock 74 through nozzle assembly 60. Delivery tube 61 can be substantially tubular with a blunt distal tip. However, delivery tube 61 is not so limited and may include a puncture tip. Delivery tube 61 can preferably range between approximately 15 gauge (outer diameter of 0.072 inches and inner diameter 0.054 inches) to approximately 30 gauge (outer diameter of 0.01225 inches and inner diameter of 0.00625 inches). At a distal end of luer lock 74, a distal end of voltage wire 92d can run through nozzle tube 92 and be connected to a proximal portion of inner distal delivery tube 61, which can be constructed from one or more conductive materials. Wire 92d can include a needle-like structure made of one or more conductive materials (e.g., metal) that can create the electric field to charge the liquid solution that flows from syringe 70 through nozzle assembly 60. In operation, syringe 70 can be configured to deliver the stored liquid solution at a predetermined rate from barrel portion 72 through delivery tube 61 and ultimately sprayed via nozzle assembly 60 onto a treatment site (e.g., a wound site of a patient).

In some aspects, voltage wire 92d can be in electrical communication with a voltage source at one end (e.g., port 46) and a nozzle tube (e.g., nozzle tube 92d) at a nozzle end as shown in FIGS. 5B and 5C. While not shown, it is contemplated that in some aspects contact 46 can be in direct electrical communication with aspects of syringe 70 (e.g., directly connected to plunger 71) rather than running wire 92d from port 46 to tube 61. Voltage wire 92d can be substantially axially aligned along syringe 70 within the disposable cartridge 50. Nozzle tube 92 can be positioned so that a nozzle end of the wire 92d can electrically charge contents of syringe 70 (e.g., by contacting delivery tube 61 as it distally exits luer lock 74) prior to delivery from nozzle assembly 60. For example, distal end of luer lock 74 where delivery tube 61 passes can be electrically connected to a distal end of wire 92d, as shown in FIG. 5B, while an opposite end of the voltage wire 92d (contact end 46) can be in electrical communication with contact end 92a, wire 92c, and port 92e of HV module 86. In some aspects, a wire loop or hook of wire 92d can contact the delivery tube 61. In some aspects, the wire loop or hook of wire 92d can include one or more conductive materials, such as copper, steel, or any other metallic alloy. In some aspects, the inner diameter of the wire loop or hook of wire 92d can be configured to allow for contact with the delivery tube 61. In some aspects, the voltage wire 92d can be attached (e.g., spot welded, crimped, etc.) in place then potted with a high dielectric adhesive. The wire loop or hook of wire 92d can at least partially surround an outer surface of the delivery tube 61 to provide the voltage potential thereto.

In some examples, the NFC tag of disposable cartridge 50 and/or other internal memory of cartridge 50 can include other information about contents (e.g., liquid treatment solution, recommended operational parameters, tracking information, expiry date, etc.) stored therein. This information can be used, for example, by applicator 100 to monitor the type of contents, its volume as well as modify the voltage, flow rate, recommended travel distance (i.e., proximity), etc. for the particular solution. In some example, this information can be stored on an integrated memory, which can include but is not limited to RAM, ROM, EPROM, EEPROM, etc. The information on the integrated memory 120 can be relayed to the applicator 100 via on the integrated memory and/or NFC tag, and this information can be used to adjust or otherwise control aspects of cartridge (e.g., components of syringe 70 such as stopper 71a, flow rate, air intake from pump 83, a voltage applied by wire 92d to delivery tube 61, etc.). In some aspects, one or more processors of the applicator 100 can be configured to read information of the NFC tag or other internal memory of cartridge 50 related to operational parameters of cartridge 50; and presenting the read information of the NFC in the display screen (e.g., information such as identification of contents of cartridge 50, volume information, etc.). In some aspects, operational information can be written to the NFC by the processor of the electrostatic applicator system.

A distal end of tube 92 can be configured to physically connect with port 69 of nozzle assembly 60. Similarly, air supply tube 76 can run from cartridge air port 59 to nozzle air port 66 of nozzle assembly 60. Tube 76 can provide high velocity air to spray the contents of cartridge 50 (e.g., contents disposed in syringe 70) to the treatment site. The distal end of tube 76 via port 66 can be the outlet of the air supply tube 76 for providing high velocity air flow to nozzle assembly 60.

In some aspects, one or more accumulators (not shown) can be positionable within disposable cartridge 50 or the housing, whereby the one or more accumulators are configured to accept, store, and release energy during operation of the disposable cartridge 50. Examples of one or more accumulators contemplated for use with disposable cartridge 50 may include one or more springs, flywheel energy storage mechanisms, batteries, capacitors, etc.

Turning to FIG. 6, a spring 106 (e.g., a disposably latch spring) can be in communication with a cartridge side of button 57. In operation, spring 106 can provide a spring bias to button 57 that keeps button 57 in the closed position, as shown in the close-up cross section view of section 6 of FIG. 3 which is illustrated in FIG. 6. In some aspects, button 57 as arranged in FIG. 6 with spring 106 can be living hinge configured to maintain button 57 in the depicted closed, retained position. Within the housing side of housing 10, a solenoid 115 can be provided. In FIG. 6, solenoid 115 is depicted in a non-energized position. A solenoid plunger 117 is provided within solenoid 115 and can include a return spring. A solenoid plunger tip 113 can be provided a distal end of plunger 117. As can also be seen, a rigid housing catch 109 is provided so as to retain button 57 in the closed configuration with solenoid 115, including plunger 117 and tip 113. The depicted example of FIG. 6 is but one manner to provide easy, secure attachment and detachment of cartridge 50 with housing 10 of applicator 100 and other attachment approaches are contemplated for use with the disposable cartridge 50 of this disclosure.

Figure 7A:
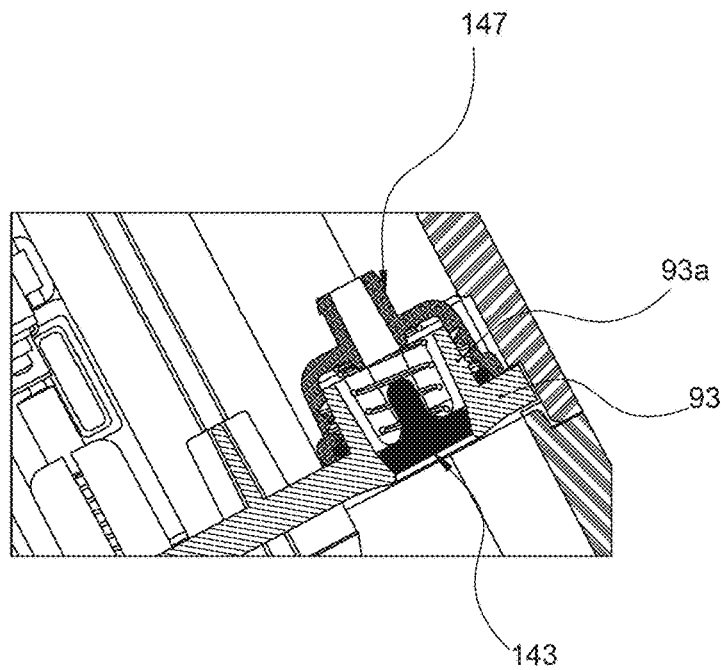
FIG. 7A depicts a close-up cross-section view of example aspects of FIG. 3 showing a closed system in the air intake and exhaust ports with respect to the example electrostatic applicator and the example cartridge.
Figure 7B:
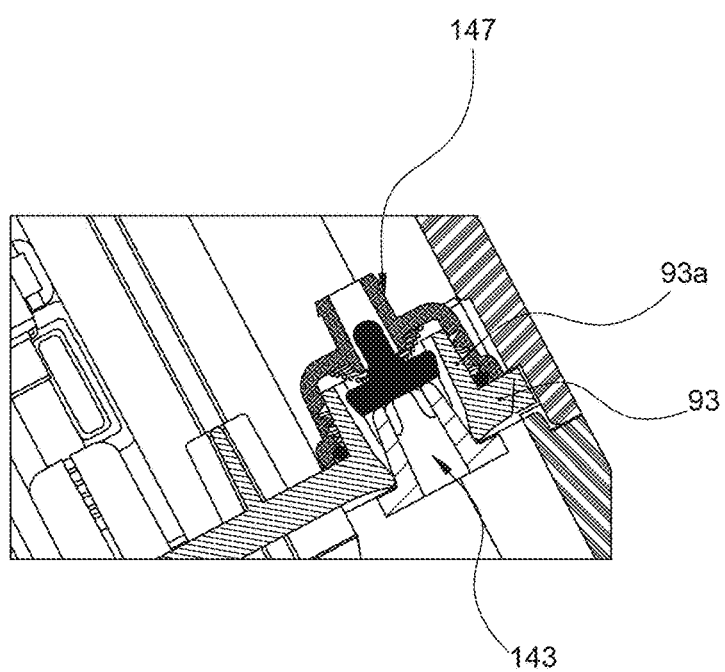
FIG. 7B depicts a close-up cross-section view similar to FIG. 7A but with an example valve seal in an open position.

FIG. 7A depicts a close-up cross-section view of example aspects of HV wall 93 when cartridge 50 is not connected with housing 10 and FIG. 7B shows example aspects of HV wall 93 when cartridge 50 is connected with housing 10. In FIG. 7A, aspects of HV wall 93 in the air intake and exhaust are closed with respect to housing 10. Specifically, port 147 can include an air path opening through HV wall 93 and ultimately to port 47 of cartridge 50. Though associated tubing of port 147 is not shown, during use tubing would be provided between port 147 and pump 83. Port 147 can include a real valve seal housing in which an intake port 93*a* of HV wall 93 can be nested. In some aspects, a valve seal conical spring can ye positioned to retrain corresponding valve seal 143 in a sealed, closed position, as shown in FIG. 7A. In FIG. 7B, cartridge 50 is shown coupled to HV wall 93. Specifically, port 47 of cartridge 50 is shown inserted into port 93*a* thereby urging seal 143 to an opened configuration. In turn, air can now pass by seal 143 and into cartridge 50.

Figure 8A:
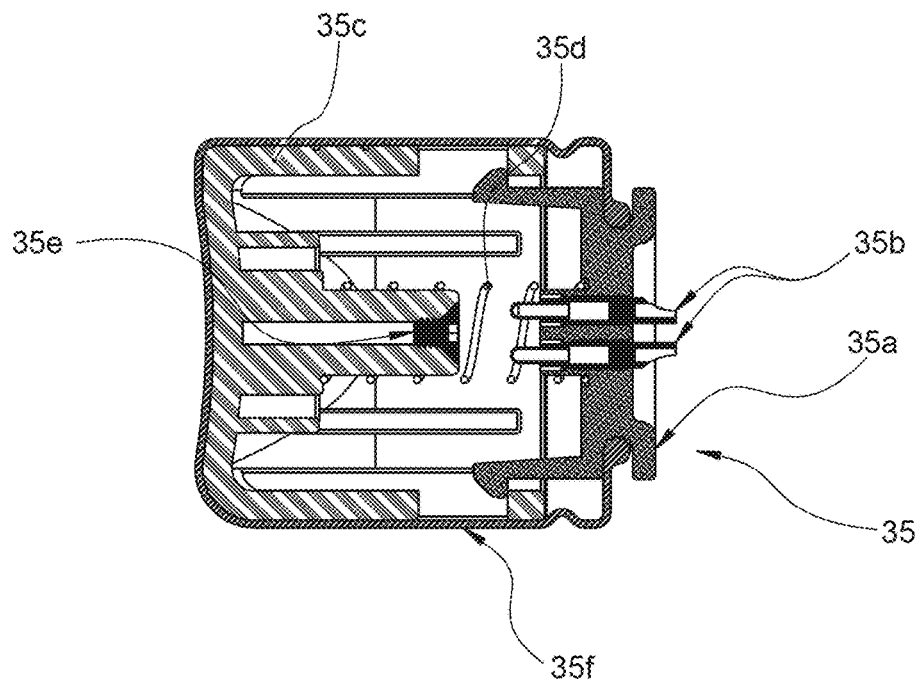
FIG. 8A depicts a side cross-section view of example aspects of the actuator previously shown in FIGS. 1A to 3.

FIG. 8A depicts a side cross-section view of example aspects of actuator 35 previously shown in FIGS. 1A to 3. Specifically, actuator 35 can include a switch base 35*a* is configured to couple directly to aspects of housing 10. In some aspects, base 35*a* can be coupled to flexible boot 35*f* and can be coupled directly switch cap 35*c*. One or more switch contacts 35*b* can be positioned in base 35*a* and in communication with a switch return spring 35*d* and switch shorting contact 35*e*. In some aspects, actuator 35 can be configured to resist high-pressure and heavy sprays of water (e.g., an IP6X water dust intrusion rating). In some aspects, the flexible boot 35*f* is configured to surround components of actuator 35 and allow motion while maintaining sealing.

Figure 8B:
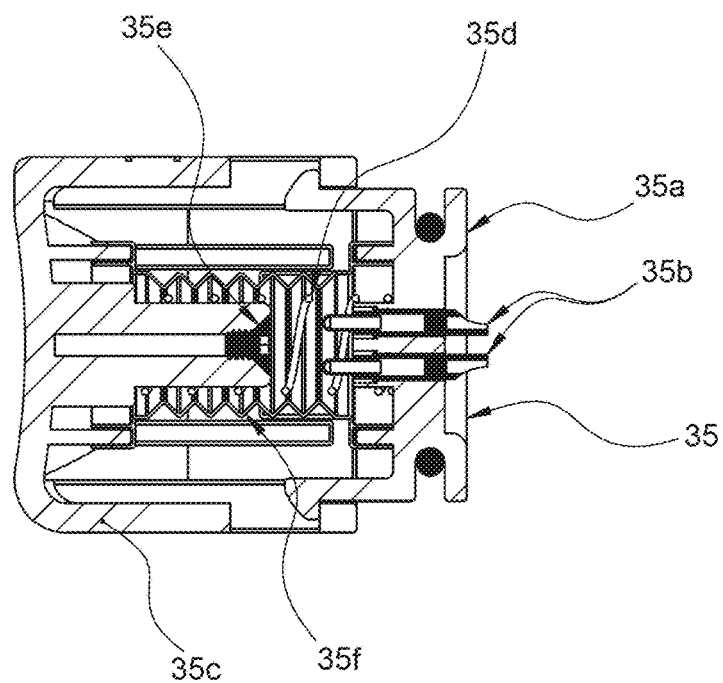
FIG. 8B depicts a side cross-section view of another example actuator previously contemplated for use with the examples of FIGS. 1A to 3.

FIG. 8B depicts a side cross-section view of another example actuator 35' previously contemplated for use with the examples of FIGS. 1A to 3, where previous flexible boot 35*f* has been replaced by flexible internal bellow boot 35' positioned internal to switch cap 35*c* and directly coupled to base 35*a*. In some aspects, flexible internal bellow boot 35' is configured to surround return spring 35*d* and contact 35*e* so as to resist high-pressure and heavy sprays of water (e.g., an IP6X water dust intrusion rating).

Figure 9A:
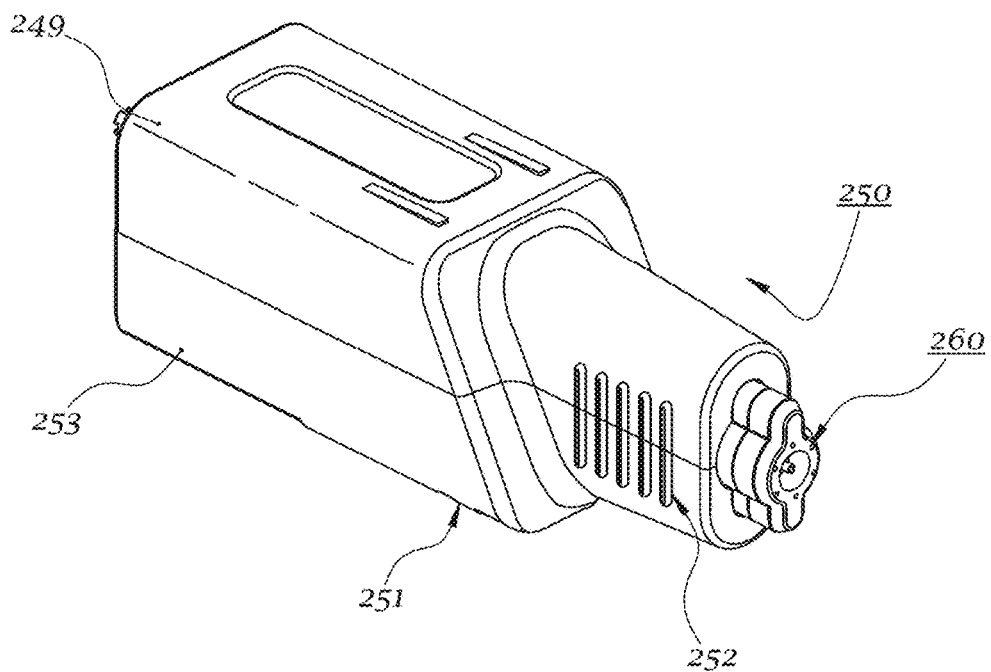
FIG. 9A depicts a forward perspective view of an example electrospinning cartridge contemplated for use with the example electrostatic applicator of FIGS. 1A to 3.
Figure 9B:
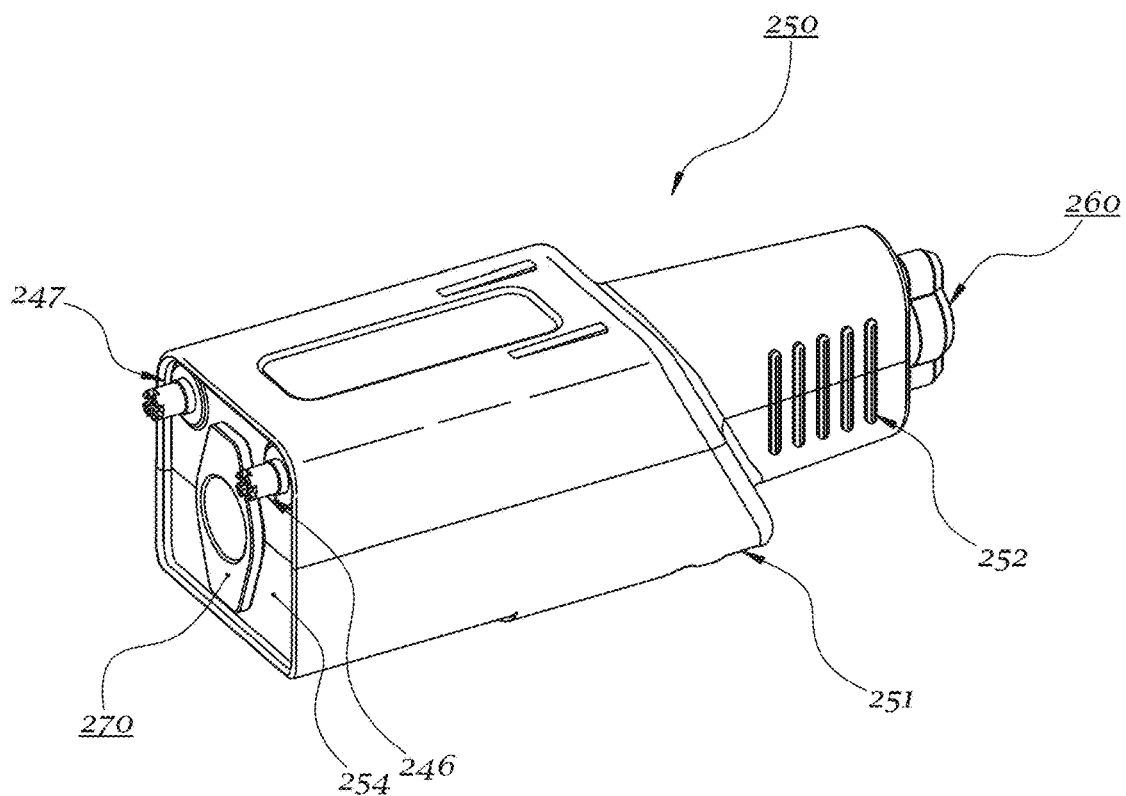
FIG. 9B depicts a rear perspective view of the example electrospinning cartridge contemplated for use with the example electrostatic applicator of FIGS. 1A to 3.
Figure 10A:
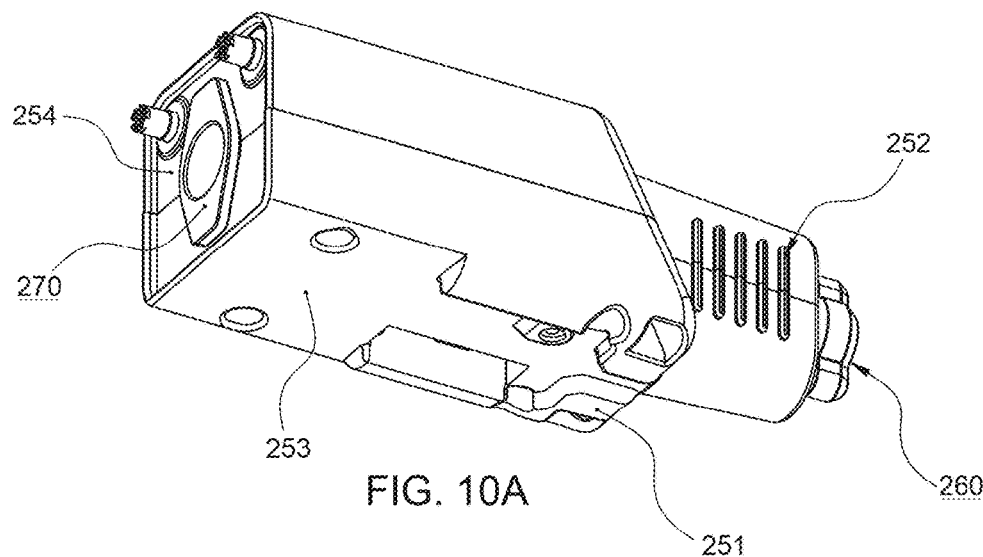
FIG. 10A depicts a lower rear perspective view of the example cartridge of FIGS. 9A-9B.
Figure 10B:
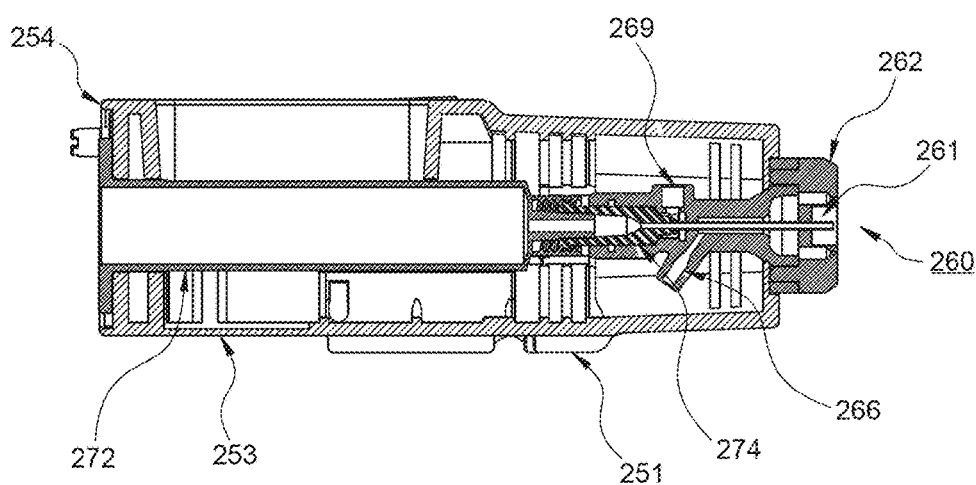
FIG. 10B depicts a side view of the example cartridge of FIGS. 9A-9B with a portion of its outer housing removed.
Figure 10C:
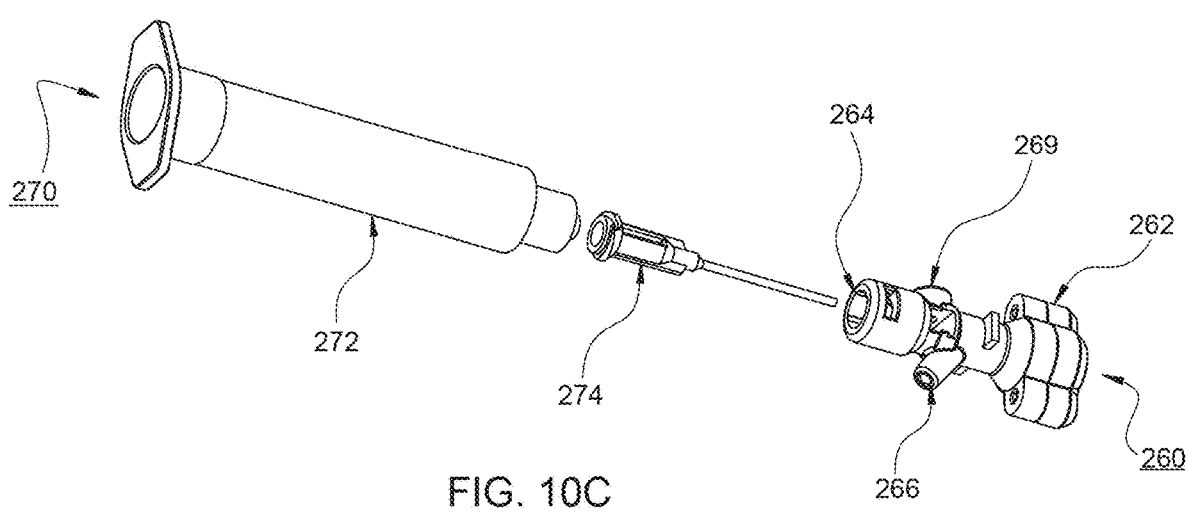
FIG. 10C depicts an exploded perspective view of internal components of example cartridge of FIGS. 9A-9B with its outer housing removed.

Referring to FIG. 9A, a forward perspective view of a cartridge 250 configured for electrospinning is provided while FIG. 9B depicts a rear perspective view of cartridge 250. Aspects of cartridge 250 include like numerals as in cartridge 50 indicate like structural elements and features. In some aspects, nozzle 260 of cartridge 250 is configured to receive source liquid from syringe 270 and feed high-compressed air via one or more injection holes 267 so that the source liquid of syringe 270 for fiber can be injected together with air and a voltage applied thereto to produce and emit electrospun fibers having fine diameters. In some aspects, holes 267 can be radially arranged around tube 261 and formed in FIG. 9B specifically shows the supply end and contact end of cartridge 250. HV contact 246 is positioned on a face of cartridge HV wall 254, which is configured to mount against HV wall 93 of housing 10. HV wall 254 can also include an air intake port 247 which can be configured to couple to a corresponding air intake port 147 of HV wall 93 (see, e.g., FIGS. 7A and 7B).

Similarly, FIG. 10A depicts a lower rear perspective view of cartridge 250. FIG. 10B depicts a side view of cartridge with a portion of its outer housing 249 removed while FIG. 10C depicts an exploded perspective view of internal components of cartridge 250 with outer housing 249 removed. Similar to housing 49, housing 249 can be formed and/or assembled in a number of ways, including but not limited to, machining, molding, injection molding, three-dimensional printing, or any other suitable manufacturing process. Suitable materials for housing 249 may include one or more of glass filled nylon, glass filled polypropylene, glass filled polyethylene, polypropylene, polyethylene, or a plastic material.

As shown in FIGS. 9A, 10B, and 10C, nozzle assembly 260 can include nozzle housing 260*a*. Housing 260*a* can include nozzle outlet channel 262 on a distal end that can contain the outlet end of delivery tube 261. The nozzle housing 260*a* can include air inlet port 266 in fluid communication with holes 267 positioned about channel 262. As shown in FIG. 9A, housing 260*a* can include six (6) holes radially arranged around a common axis of channel 262, though fewer or greater number of holes can be used as needed or required. In some aspects, holes 267 can be replaced by an outer concentric outlet channel that completely surrounds channel 262 and is similarly in fluid communication with port 266. During use, air pumped from port 266 and out through holes 267 can create an air curtain, around the electrospun fiber being emitted from tube 261. In the depicted example of FIG. 9A, holes 267 are shaped substantially straight or otherwise angled in parallel and/or axially aligned with tube 261 so that the shape of the corresponding air curtain is similarly parallel and/or axially aligned. In other examples, holes 267 are shaped angled upwards relative to a longitudinal axis of tube 261 so as to create a funnel shaped, tapered outward air curtain. In other examples, holes 267 are shaped angled downwards relative to a longitudinal axis of tube 261 so as to create a converging, tapered inward shaped air curtain.

In some examples, housing 249 can comprise two or more sections of moldable plastic, e.g., a first half and a second half (which, when assembled together will be referred to herein as housing 249). The two or more sections can be assembled together with fasteners (e.g., screws, rivets, a weld [e.g., a sonic weld], one or more straps or snaps, an adhesive or adhesive tape, etc.) such that the internal components are disposed between the portions and/or respective halves of housing 249. In some aspects, housing 249 can include a fiber outlet associated with nozzle assembly 260 that enables the atomized, charged treatment solution to be expelled from cartridge 250. Port 247 is configured to receive air supply tube 81 to place tubes 81, 76 and pump 83 in fluid communication with each other.

Just as with cartridge 50, cartridge 250 can securely engage with chamber 27. Though not shown, cartridge 250 can contain, within its housing 249, an air supply tube, voltage tube, and syringe 270. Similar to syringe 270, syringe 270 can be an assembly that includes a glass or plastic syringe for storing the liquid solution that is to be applied using the disposable cartridge 250. Syringe 270 can be assembled within the disposable cartridge 250 pre-filled with the desired liquid solution. At a proximal end, syringe 270 can include a plunger and a barrel portion 272 extended distally therefrom. Contents of syringe 270 can be advanced through luer lock 274 positioned at distal end of portion 272. An inner distal delivery tube 261 can be distally extended from luer lock 274 through nozzle assembly 260. At a distal end of luer lock 274, a distal end of a voltage wire (not shown, though similar to wire 92*d* of cartridge 50) can run through the nozzle tube of cartridge 250 and be connected to a proximal portion of inner distal delivery tube 261, which can be constructed from one or more conductive materials. In operation, syringe 270 can be configured to deliver the electrospun fiber from the stored liquid solution at a predetermined rate from barrel portion 272 through delivery tube 261 and ultimately emitted via nozzle assembly 260 onto a treatment site (e.g., a wound site of a patient).

In some examples, the previously mentioned NFC tag of disposable cartridge 250 and/or other internal memory of cartridge 250 can include other information about contents (e.g., liquid treatment solution) stored therein. This information can be used, for example, by applicator 100 to monitor the type of contents, its volume as well as modify the voltage, flow rate, recommended travel distance (i.e., proximity), etc. for the particular solution. In some example, this information can be stored on an integrated memory, which can include but is not limited to RAM, ROM, EPROM, EEPROM, etc. The information on the integrated memory 120 can be relayed to the applicator 100 via on the integrated memory and/or NFC tag, and this information can be used to adjust or otherwise control aspects of cartridge (e.g., components of syringe 270).

Figure 11A:
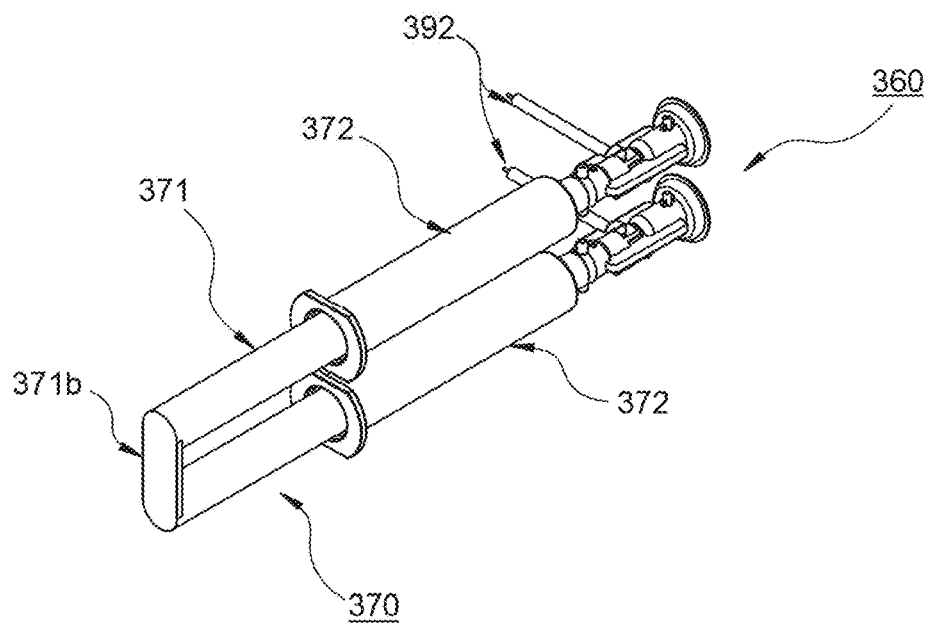
FIG. 11A depicts a perspective view of internal components of an example electrostatic cartridge contemplated for use with the example electrostatic applicator of FIGS. 1A to 3, the components including a pair of syringe and electrostatic nozzles.
Figure 11B:
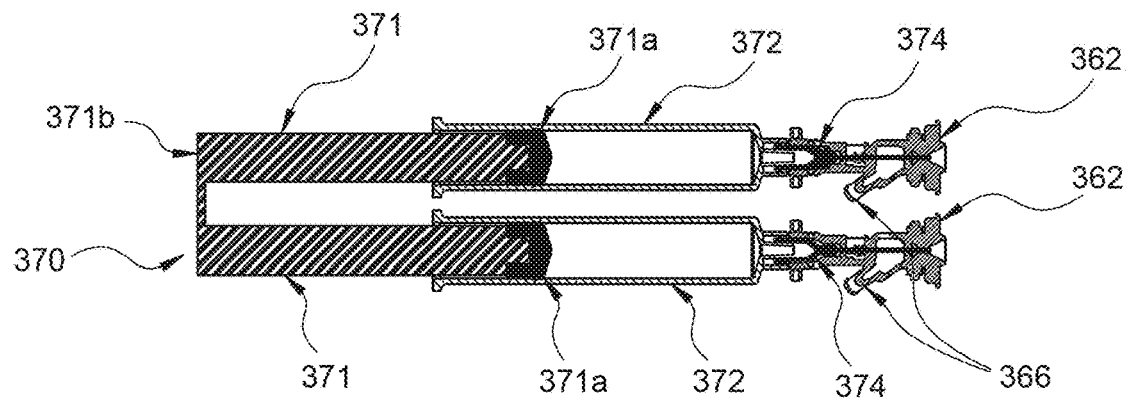
FIG. 11B depicts a side cross-section view of the example internal components shown in FIG. 11A.

FIG. 11A depicts a perspective view of internal components of another example electrostatic cartridge 350 contemplated for use with the example electrostatic applicator of FIGS. 1A to 3, the components including a pair of syringe and electrostatic nozzles. FIG. 11B depicts a side cross-section view of the example internal components shown in FIG. 11A. The outer housing of cartridge 350 is not shown in FIGS. 11A and 11B strictly for illustrative purposes to observe these internal components. As opposed to previously described cartridges 50 and 250, cartridge 350 can contain, within its housing, a multi-plunger syringe 370 whereby each sub-syringe of multi-plunger syringe 370 can include its own air supply tube, voltage tube 392, barrel portion 372, stopper 371a, and syringe actuating shaft 371. Actuating shafts 371 of multi-plunger syringe 370 can be connected proximally via a central drive surface 371b so that advancing surface 371b causes each connected actuating shaft 371 to simultaneously advance respective stopper 371a to distally urge contents stored in respective portion 372 through respective luer locks 374 and ultimately into respective nozzle assemblies 360. In some aspects, the voltage tubes 392 and respective voltage wires (not shown) of the depicted examples in FIGS. 11A and 11B can include separate and independent high voltage inputs. In some aspects, the example of FIGS. 11A and 11B is configured to increase the production of deliverable treatment solution therefrom (e.g., electrosprayed contents, electrospun fiber, etc.) as well as cover greater areas faster via multiple nozzle assemblies with the high voltage separated and independent all the way through the fluid path, as shown. In some aspects, syringe 370 can be configured so that sub-assemblies dispense in different ratios other than 1:1. While only two sub-assemblies are shown in FIGS. 11A and 11B, it is contemplated that more than two sub-assemblies can be used as needed or required.

Figure 12A:
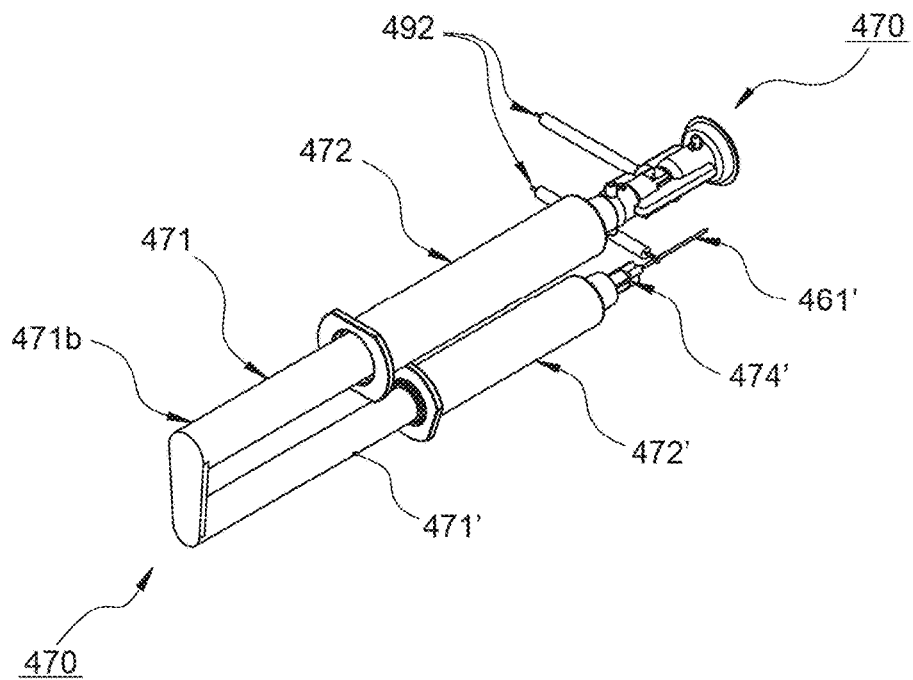
FIG. 12A depicts a perspective view of internal components of an example electrostatic cartridge contemplated for use with the example electrostatic applicator of FIGS. 1A to 3, the components including a pair of syringes, at least one electrostatic nozzle, and at least one electrospinning delivery tube.
Figure 12B:
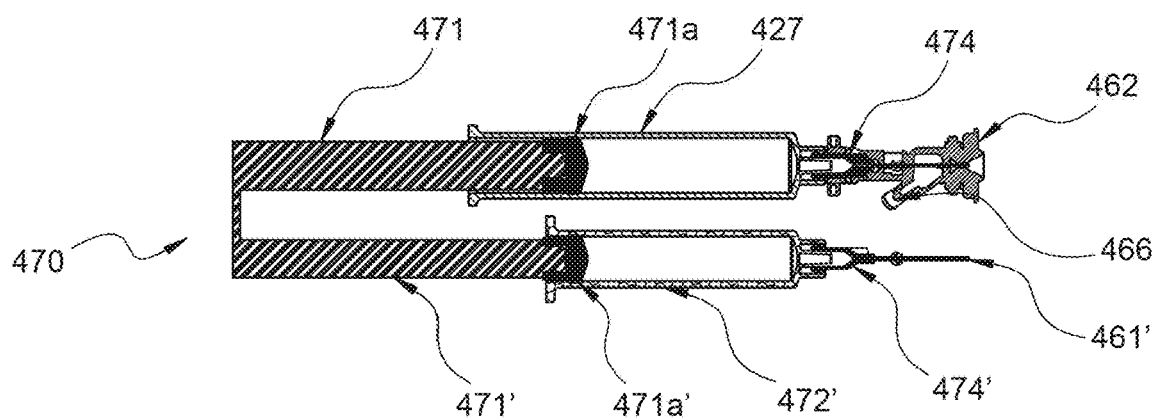
FIG. 12B depicts a side cross-section view of the example internal components shown in FIG. 12A.

FIG. 12A depicts a perspective view of internal components of another example electrostatic cartridge 450 contemplated for use with the example electrostatic applicator of FIGS. 1A to 3, the components including a pair of syringe and electrostatic nozzles. FIG. 12B depicts a side cross-section view of the example internal components shown in FIG. 12A. The outer housing of cartridge 450 is not shown in FIGS. 12A and 12B strictly for illustrative purposes to observe these internal components. In some aspects, the example of FIGS. 12A and 12B is configured to increase the production of deliverable treatment solution therefrom (e.g., electrosprayed contents, electrospun fiber, etc.) as well as cover greater areas faster via multiple nozzle assemblies with the high voltage separated and independent all the way through the fluid path, as shown. In some aspects, a first subassembly of syringe 470 can include rod 471, stopper 471a, barrel portion 472, luer lock 474, and nozzle assembly 460, collectively which are configured for electrospraying. In some aspects, a second subassembly of syringe 470 can include rod 471', stopper 471a', barrel portion 472', luer lock 474', and electrospinning tube 461', collectively which are configured for electrospinning. In some aspects, syringe 470 can be configured so that sub-assemblies dispense in different ratios other than 1:1. In some aspects, use of each of the first and second subassemblies of syringe 470 is advantageous to utilize both electrospraying and electrospinning with a single cartridge. In some aspects, barrel portions 472 and 472' can be configured to contain a different volume and/or type of fluid solution.

As opposed to previously described cartridges 50 and 250, cartridge 450 can contain, within its housing, a multi-plunger syringe 470 whereby each sub-syringe of multi-plunger syringe 470 can include its own air supply tube, voltage tube 492, barrel portion 472, 472', stopper 471a, 471a', and syringe rod 471, 471'. Shafts 471, 471' of multi-plunger syringe 470 can be connected proximally via a central drive surface 471b so that advancing surface 471b causes each connected rod 471, 471' to simultaneously advance respective stopper 471a, 471a' to distally urge contents stored in respective portion 472, 472' through respective luer locks 474, 474' and ultimately into respective nozzle assemblies. In some aspects, the voltage tubes 492 and respective voltage wires (not shown) of the depicted examples in FIGS. 12A and 12B can include separate and independent high voltage inputs. While only two sub-assemblies are shown in FIGS. 12A and 12B, it is contemplated that more than two sub-assemblies can be used as needed or required.

Figure 13A:
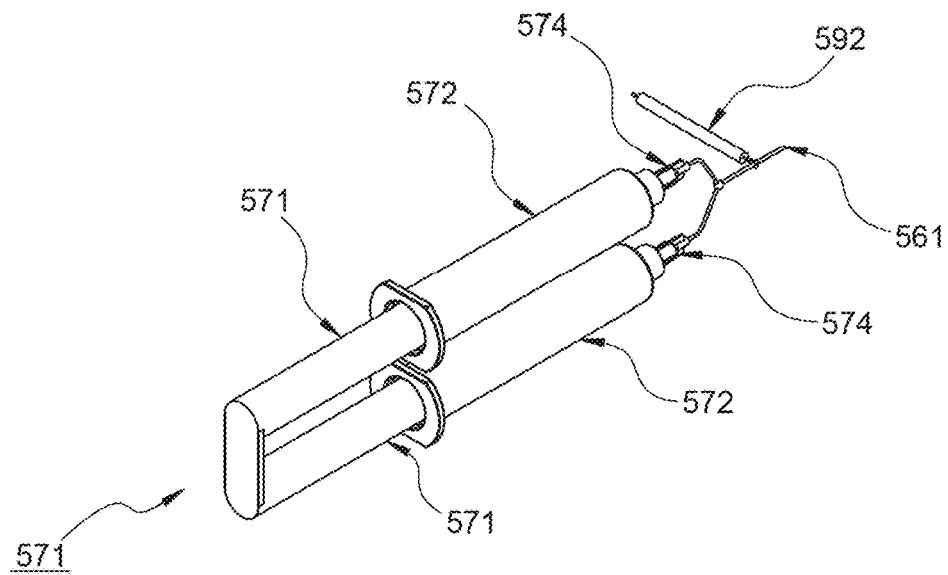
FIG. 13A depicts a perspective view of internal components of an example electrostatic cartridge contemplated for use with the example electrostatic applicator of FIGS. 1A to 3, the components including a pair of syringes and electrospinning delivery tubes interconnected by a Y-shaped member.
Figure 13B:
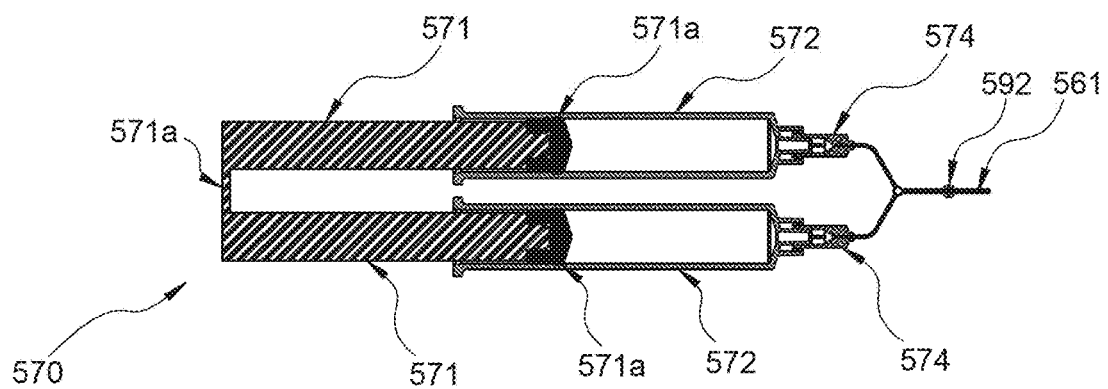
FIG. 13B depicts a side cross-section view of the example internal components shown in FIG. 13A.

FIG. 13A depicts a perspective view of internal components of another example electrostatic cartridge 550 contemplated for use with the example electrostatic applicator of FIGS. 1A to 3, the components including a pair of syringe and electrostatic nozzles. FIG. 13B depicts a side cross-section view of the example internal components shown in FIG. 13A. The outer housing of cartridge 550 is not shown in FIGS. 13A and 13B strictly for illustrative purposes to observe these internal components. As opposed to previously described cartridges 50 and 250, cartridge 550 can contain, within its housing, a multi-plunger syringe 570 whereby each sub-syringe of multi-plunger syringe 570 can include its own air supply tube, voltage tube 592, barrel portion 572, stopper 571a, and syringe rod 571. Actuating shafts 571 of multi-plunger syringe 570 can be connected proximally via a central drive surface 571b so that advancing surface 571b causes each connected rod 571 to simultaneously advance respective stopper 571a to distally urge contents stored in respective portion 572 through respective luer locks 574 and ultimately into respective nozzle assemblies 560.

In the example of FIGS. 13A and 13B, each of barrel portions 572 and corresponding subassembly structure can be interconnected by a Y-shaped delivery neede 561. Tube 561 as shown can include proximal ports in fluid communication with each luer lock 574 and barrel portions 572 and join in a single distal end through solution can be emitted or otherwise exit. Voltage tube 592 and corresponding voltage wire (not shown) can couple to delivery tube 561 proximal of the distalmost end of tube 561 so that all solution emitted therefrom is charged by the voltage wire. While a Y-shaped member is shown, any number of syringe subassemblies can be used as required with cartridge 550. In some aspects, the voltage tubes 592 and respective voltage wires (not shown) of the depicted examples in FIGS. 13A and 13B can include separate and independent high voltage inputs. In some aspects, the example of FIGS. 13A and 13B is configured to increase the production of deliverable treatment solution therefrom (e.g., electrosprayed contents, electrospun fiber, etc.) as well as cover greater areas faster via multiple nozzle assemblies with the high voltage separated and independent all the way through the fluid path, as shown. In some aspects, syringe 570 can be configured so that sub-assemblies dispense in different ratios other than 1:1. While only two sub-assemblies are shown in FIGS. 13A and 13B, it is contemplated that more than two sub-assemblies can be used as needed or required.

Figure 14A:
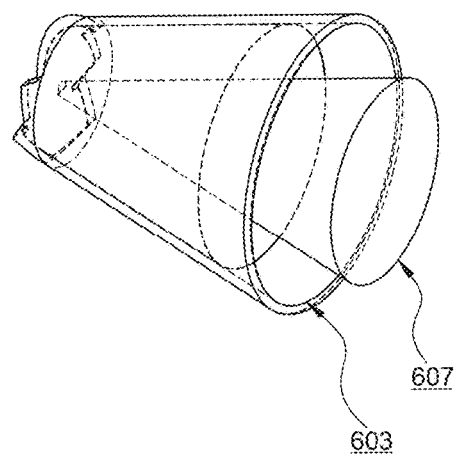
FIG. 14A depicts a side perspective view of an example cone configured for use with any of the herein disclosed nozzles of the described disposable cartridges.

FIG. 14A depicts a side perspective view of an example cone 607, 603 configured for use with any of the herein disclosed nozzle assemblies of the described disposable cartridges. In some aspects, cone 603 can be a physical cone of any material that attaches to either a distal end of the nozzle assembly or directly to the housing 10. In some aspects, cone 607 can be attached directly to a distal end of a delivery tube associate with the respective nozzle assembly. In some aspects, cone 603 can be configured to protect the emission of electrospraying or electrospinning materials from the respective system (e.g., applicator 100 and any disposable cartridge connected thereto) to the treatment site (e.g., a wound site of the patient) by preventing external air flow and/or external forces from interfering. In some aspects, cone 603 can be configured to control airflow in the respective nozzle assembly by reflecting spray off of its cone walls. In some aspects, once attached to housing 10 and/or a respective nozzle assembly, cone 603 can be configured so that one or more lights (e.g., LED lights) can ring the proximal end of the cone from the electrostatic applicator and generate a light pattern (e.g., a light ring) via the light pipe effect on the target site to aide targeting. In some aspects, if a translucent material is used with cone 603, the cone can disperse the light, including different colors, from applicator 100 to notify the user of proper distance by warning if the applicator is too close or too far.

Figure 14B:
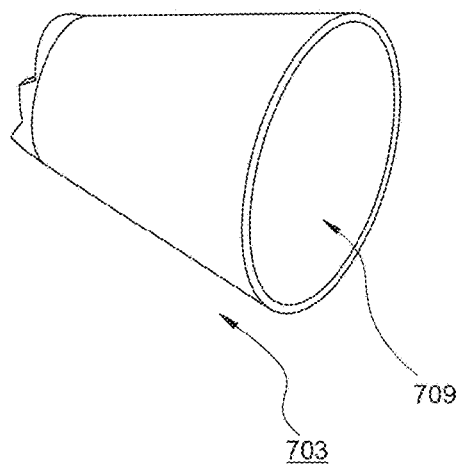
FIG. 14B depicts a side perspective view of another example cone configured for use with any of the herein disclosed nozzles of the described disposable cartridges.

FIG. 14B depicts a side perspective view of another example cone 703 configured for use with any of the herein disclosed nozzle assemblies of the described disposable cartridges. In some aspects, cone 703 can be a physical cone of any material that attaches to either a distal end of the nozzle assembly or directly to the housing 10. Similarly, cone 703 can illuminate when solution is being emitted therefrom. For example, inner surface 709 of cone 703 can be configured to illuminate as well as be plated or finished with a non-stick surface.

Figure 14C:
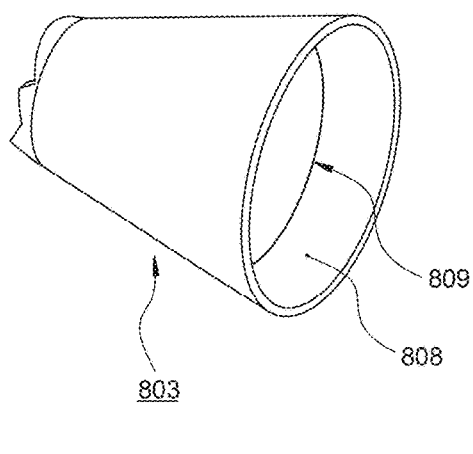
FIG. 14C depicts a side perspective view of another example cone configured for use with any of the herein disclosed nozzles of the described disposable cartridges.

FIG. 14C depicts a side perspective view of another example cone 803 configured for use with any of the herein disclosed nozzle assemblies of the described disposable cartridges. In some aspects, cone 803 can be a physical cone of any material that attaches to either a distal end of the nozzle assembly or directly to the housing 10. In some aspects, inner surface 809 of cone 803 can be plated or finished with a conductive surface that can have the same polarity as the fluid being dispensed that would help with the dispensing direction. A distal edge 808 of cone 803 can be left without that same conductive surface plating and/or finishing.

Figure 14D:
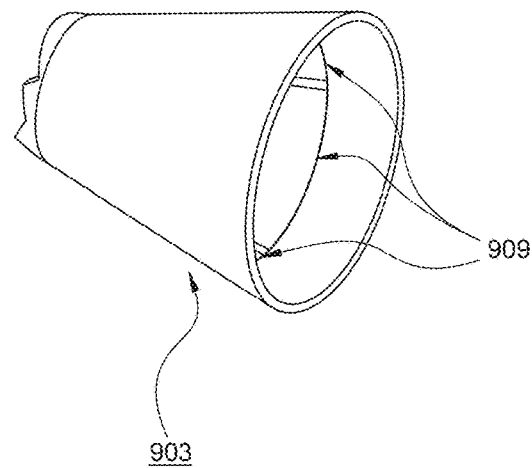
FIG. 14D depicts a side perspective view of another example cone configured for use with any of the herein disclosed nozzles of the described disposable cartridges.

FIG. 14D depicts a side perspective view of another example cone 903 configured for use with any of the herein disclosed nozzle assemblies of the described disposable cartridges. In some aspects, cone 903 can be a physical cone of any material that attaches to either a distal end of the nozzle assembly or directly to the housing 10. In some aspects, inner surface 909 of cone 903 can be plated or finished with multiple conductive surfaces (e.g., radially separated surfaces that can be charged to repel and/or attract the solution and change dispensing directions).

Figure 15:
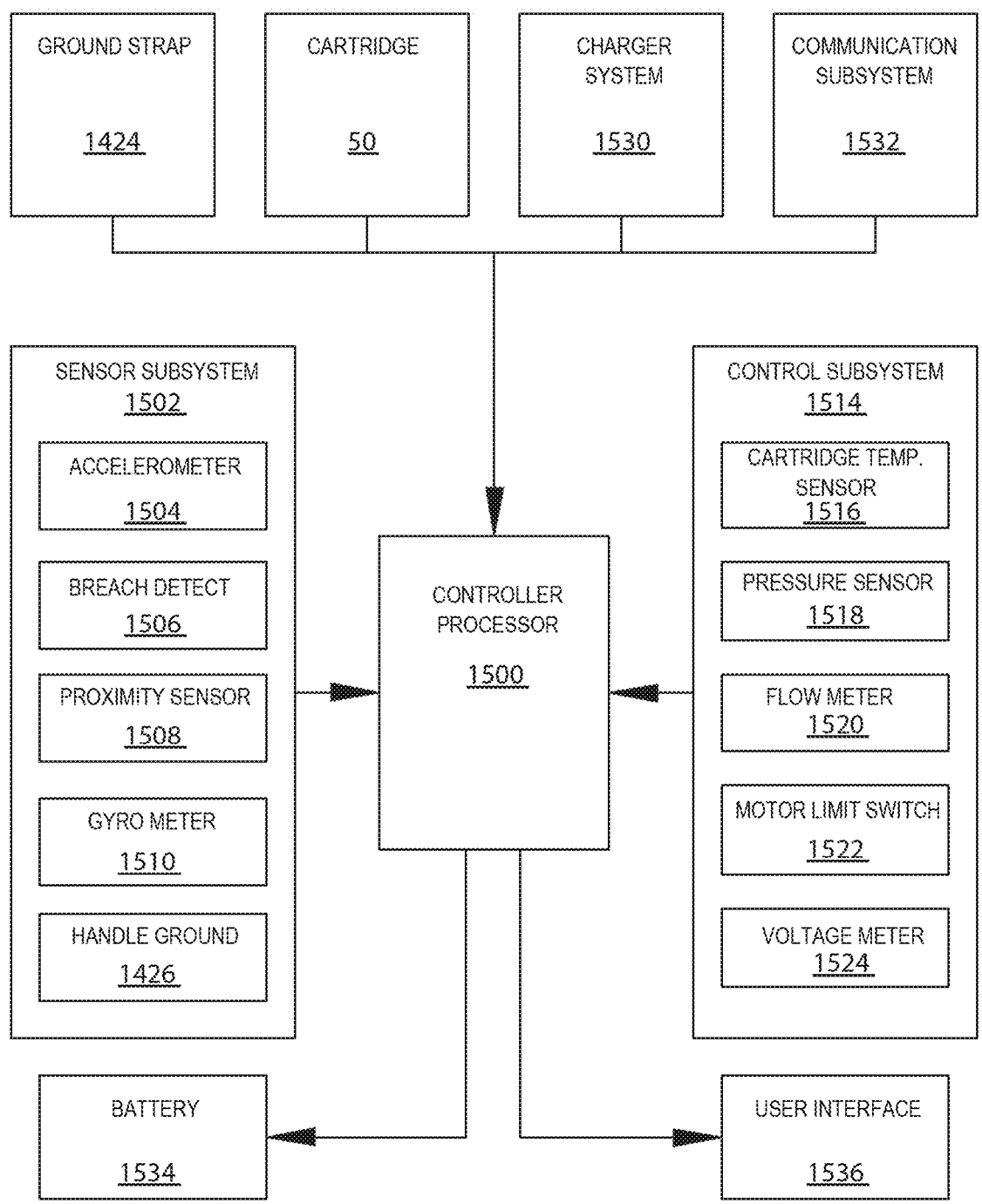
FIG. 15 is a component diagram of various components and systems that can be included with electrostatic and/or electrospinning devices, according to the present disclosure.
Figure 16:
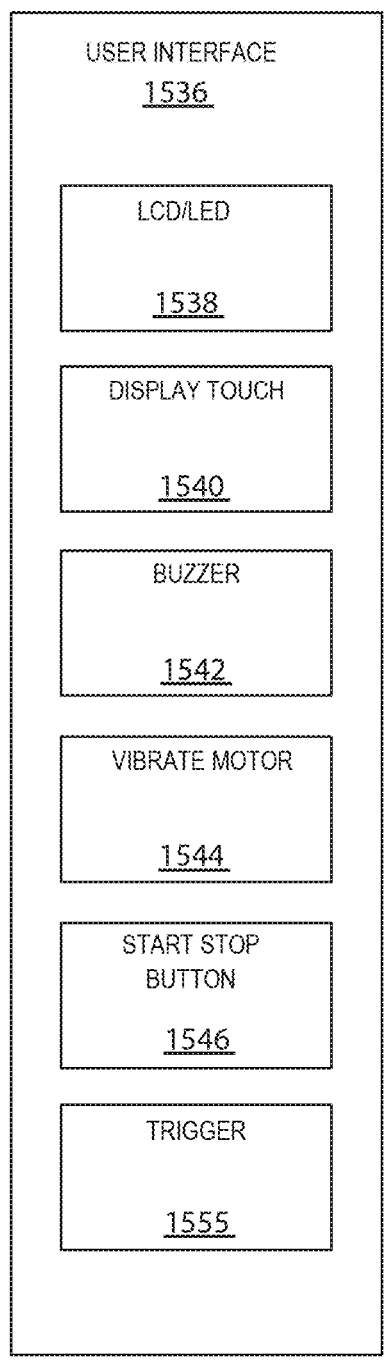
FIG. 16 is component diagram of the user interface of FIG. 15, according to the present disclosure.
Figure 17:
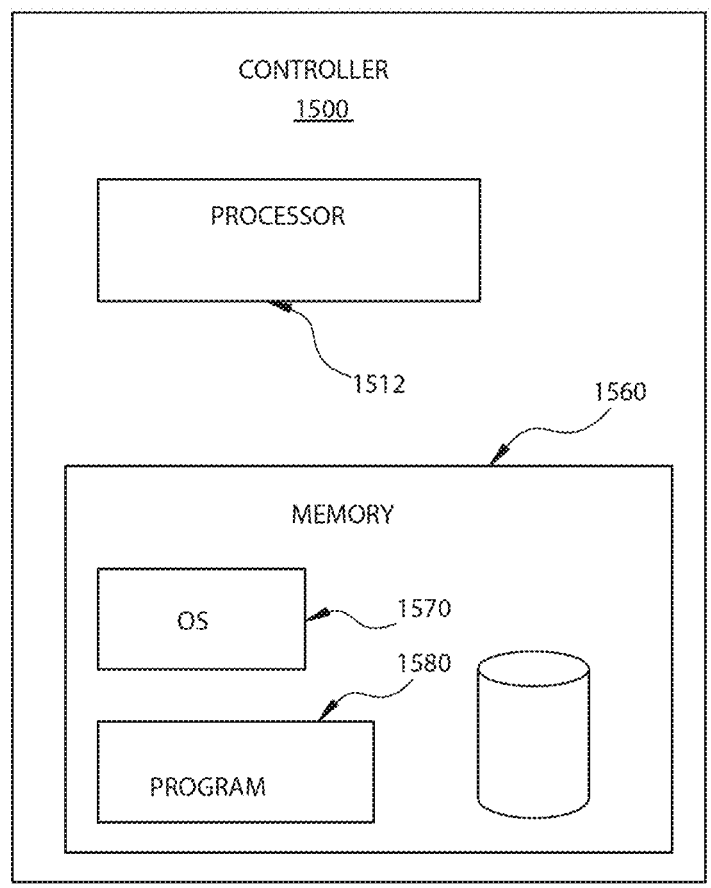
FIG. 17 is a component diagram of the controller of FIG. 15, according to the present disclosure.

FIGS. 15-17 are component diagrams of various components and systems that can be included in an electrostatic applicator system (for example within the applicator 100 and/or any of the disposable cartridges 50, 250, 350, 450, 550), according to the present disclosure. A controller 1500, which can include a the CPU, can communicate with the various components and systems to operate the electrostatic applicator. For example, the controller 1500 can communicate with the disposable cartridge in order to receive information about the particular fluid contained within the cartridge. This information communicated to the controller 1500 (e.g., via integrated memory) can include information about preferred fluid flow rates (e.g., by adjusting the motor speed), air supply rates, voltages (e.g., by adjusting the voltage potential between the voltage supply (e.g., HV module 86) and delivery tube of the respective nozzle assembly of the respective cartridge) and the like such that preferred nanoparticles can be formed from the sprayed therapeutic solution. This information enables a single reusable applicator 100 to be used with numerous different disposable cartridges 50, 250, 350, 450, 550 with different solutions. Further, not only are the fluids potentially different in each disposable cartridge 50, 250, 350, 450, 550. For example, different disposable cartridges 50, 250, 350, 450, 550 can have different air supply tubes, voltage wires, and/or nozzle assemblies depending on the particular application for the disposable cartridge 50, 250, 350, 450, 550. To this end, this component information can also be relayed to controller 1500 so that the reusable applicator 100 can be adjusted accordingly.

The controller 1500 can communicate with a sensor subsystem 1502 that includes various sensors that can be used to operate the reusable applicator 100. The sensor subsystem 1502 can include an accelerometer 1504 that can be used to wake the CPU when the user moves the reusable applicator 100. For example, in addition to or as an alternative to any button or capacitive input from an associated user interface described above, the reusable applicator 100 can automatically turn on (e.g., the CPU can receive power) when the accelerometer detects movement of the reusable electrostatic applicator. The sensor subsystem 1502 can include a breach detect 1506 located proximate cartridge chamber 27 to determine if the cartridge is sufficiently attached to chamber 27. The breach detect 1506 can act as a safety measure to ensure the disposable cartridge 50, 250, 350, 450, 550 is fully seated and within chamber 27 before the applicator 100 can be activated. The breach detect 1506 can be a pressure sensor, switch, and/or the like.

The sensor subsystem 1502 can include a proximity sensor 1508 to detect how close the reusable applicator 100 is to the treatment or target site. The proximity sensor 1508 can be positioned at the distal end of the reusable applicator 100, for example proximate or adjacent the spray outlet of the respective cartridge 50, 250, 350, 450, 550. Alternatively, the proximity sensor 1508 can be positioned on the disposable cartridge 50, 250, 350, 450, 550 proximate or adjacent the housing spray outlet of the respective cartridge 50, 250, 350, 450, 550. The proximity sensor 1508 can include but is not limited to inductive proximity sensors, capacitive proximity sensors, photoelectric proximity sensors, and the like. The proximity sensor 1508 can be a safety feature (e.g., configured to detect proximity between the electrostatic applicator and the target) used to indicate to the operator whether the electrostatic applicator is within a preferred distance to the target object. For example, the travel distance of the charged droplets can affect the morphology of the droplets as they contact the target site. To this end, the proximity sensor 1508 can transmit signals to the controller 1500 to indicate the distance to the target object, and the controller 1500 can output a signal to a user interface 1536 (e.g., a display screen, an external user device, etc.) to alert the user if the device is too far away from or too close to the target site. This information can be based upon the information stored on integrated memory of the disposable cartridge 50, 250, 350, 450, 550, as described above.

The sensor subsystem 1502 can include a gyrometer 1510 (or gyroscope) that can be used to help to measure or maintain a certain positioning of the reusable applicator 100. For example, the gyrometer 1510 can output a signal to the user interface 1536 (e.g., the display screen, an external user device, etc.) to indicate to the user that the device should be moved to an upright configuration or any other configuration. The sensor subsystem 1502 can also include the handle ground 1426 described above. In addition to grounding the operator, the handle ground 1426 can be used to detect if a user is holding the device and whether the device should be activated.

The controller 1500 can communicate with a control subsystem 1514 that includes various sensors, switches, and the like that can be used to ensure the reusable applicator 100 is operating as expected. The control subsystem 1514 can include a cartridge temperature sensor 1516. Although it is contemplated that the disposable cartridge 50, 250, 350, 450, 550 can be stored and used at room temperature, the cartridge can also be stored in other conditions, for example in a frozen state to preserve the therapeutic solution stored therein. The cartridge temperature sensor 1516 can detect the temperature of the therapeutic solution and alert the user if the solution is too cold, or too hot, to be administered to a patient's skin.

The control subsystem 1514 can include a pressure sensor 1518 positioned to read the air pressure of air flow through the air supply into the respective cartridge (e.g., the air supply associated with pump 83). This pressure information can be used by the controller 1500 to determine if the air flow through the device is providing the preferred air velocity for the particular fluid being sprayed. The control subsystem 1514 can include a flow meter 1520 positioned to read the fluid flow rate of the fluid travelling through or out of the nozzle of the respective cartridge 50, 250, 350, 450, 550. This flow rate information can be used by the controller 1500 to determine if the fluid flow through the device is providing the fluid volume for the particular solution being sprayed.

The control subsystem 1514 can include a motor limit switch 1522. The motor limit switch 1522 can be used to define the rate at which the piston of the applicator is actuated to further define and/or modulate the flow rate of the treatment solution. The control subsystem 1514 can include a voltage meter 524. The voltage meter 524 can be used to determine what voltage is being applied at the nozzle tube 106. If the voltage is off for any reason for the particular fluid, an alert can be transmitted to the user interface 1536 (e.g., the display screen of user interface 87, an external user device, etc.).

In some aspects, the control subsystem 1514 can include or be in communication with a cartridge detect switch configured to detect presence of a cartridge when assembled with the electrostatic applicator. If presence is detected, one or more operations related to a respective cartridge can be performed or otherwise initiated. In some aspects, the control subsystem 1514 can include or be in communication with an NFC chip of disposable cartridge, whereby the NFC chip can include an integrated memory with information related to characteristics of contents (e.g., treatment solution) stored within a syringe of and/or within the cartridge, including operating parameters of the contents of the cartridge such as whether the cartridge is sealed or unsealed, flow rate, a voltage potential, and/or nozzle setting associated with nozzle, so as to adjust a motor speed or a applied voltage to the contents for deposition to the treatment site from the cartridge and/or electrostatic applicator.

The controller 1500 can also receive signals indicating whether the ground strap 424 has been applied to an external ground (e.g., the wound site of a patient and/or target). If not, the controller 1500 can transmit an alert to the user interface 1536 and/or prohibit activation of the reusable applicator 100 (e.g., preventing, for example via a switch, an electrical connection between the voltage supply of HV module 86 and the respective nozzle of the respective cartridge 50, 250, 350, 450, 550). The controller 1500 can also communicate with a charger system 1530. As described above, the voltage supply 420 can include one or more batteries that can be rechargeable. The charger system 1530 can include AC/DC converter(s) and an inductive integrated circuit(s) so as to manage charging of the rechargeable voltage supply of HV module 86.

The controller 1500 can also communicate with a communication subsystem 1532. The communication subsystem 1532 can be integrated within the CPU and/or HV module 86 and include one or more transceivers that can communicate with external devices. The one or more transceivers can be compatible with short range wireless communication connections, for example but not limitation radio-frequency identification (RFID), near field communication (NFC), Bluetooth™, low-energy Bluetooth™ (BLE), WiFi™, ZigBee™, and/or similar connections. The communication subsystem 1532 can enable the reusable applicator 100 to communicate with an external device, such as a user device. The user device can include a mobile cellular device, personal digital assistant (PDA), tablet, laptop or desktop computer, smart wearable device, and/or the like. In this example, the user device can operate similar to the display screen to provide information to the device operator. For example, a display screen of a user device can be used in addition to or as an alternative to a display screen. The wireless communication between the reusable applicator 100 and a user device can provide an option to use the user device as an actuator to activate the spraying sequence of the electrostatic applicator. For example, an activation input to the controller 1500 (or the CPU) can include providing an input into a display screen of the external user device.

Additionally, information related to the fluid within the disposable cartridge 50, 250, 350, 450, 550 can be input into the user device to inform the controller 1500 which spray parameters are to be used for the particular cartridge. In some examples, a barcode, Quick Response (QR) code, and the like can be placed on the disposable cartridge 50, 250, 350, 450, 550. A user can scan the code with a camera or other scanner on the user device, and the information can be relayed to the controller 1500. The controller 1500 can then determine the necessary spraying parameters for the particular cartridge. The user can then input an activation input (e.g., press an icon on the screen of the user device) to begin spraying the treatment solution.

Referring again to FIG. 15, the controller 1500 can communicate with a user interface 1536 that can provide information to and receive information from an operator of the reusable applicator 100. FIG. 16 provides a detailed component diagram of an example user interface 1536. The user interface 1536 can include the display screen of user interface 87 described above. For example, the user interface 1536 can include an LCD/LED screen 1538 for providing information about the status of the device to the user. In some examples, the user interface 1536 can include a display touch panel 1540. In the examples where the user interface 1536 (e.g., prior user interface 87) is a display screen on the reusable applicator 100, the display screen can include touchscreen capabilities. This can enable the display screen to receive an activation input to initiate the spray sequence for the reusable applicator 100. For example, the display screen can provide an icon that can act as a virtual "actuator" to activate the spray sequence. Further, information about the fluid contained in a particular disposable cartridge 50, 250, 350, 450, 550 can be inputted into this display touch panel 1540 so as to inform the controller 1500 (or the CPU) what parameters should be used for the particular treatment solution.

The user interface 1536 can include a buzzer 1542. The buzzer 1542 can include one or more speakers that can indicate to the operator whether an issue should be addressed with respect to the device. For example, if the disposable cartridge 50, 250, 350, 450, 550 has not been fully seated, if a ground of the applicator 100 (e.g., a ground strap 1424 or handle ground 1426) does not detect a proper ground, if the voltage supply of HV module 86 is low on power or should be charged, etc., the buzzer 1542 can provide audible feedback on the particular status. Further, the display screen of user interface 87 can also provide visual feedback to additionally alert the user to the particular issue. In addition to or alternatively, the user interface 1536 can include a vibrate motor 1544 that can indicate, via tactile feedback to the user, when an issue occurs. The user interface 1536 can include a start/stop button 1546. Alternatively, the start/stop button 1546 can be integrated into a display screen, for example display screen of user interface 87 or a display screen on an external user device, so that the activation of the device can be performed within a screen that has touchscreen capabilities. The user interface 1536 can include an actuator 1555 (e.g., a trigger). As described above, the actuator 1555 can be an actuator, a virtual actuator within a user interface of an external user device, or a virtual actuator as an icon in the display screen of the user interface 87.

FIG. 17 is a component diagram of an example controller 1500, according to the present disclosure. As described above, the controller 1500 can include one or more processors, e.g., the CPU. The CPU can include one or more of a microprocessor, microcontroller, digital signal processor, co-processor and/or the like or combinations thereof capable of executing stored instructions and operating upon data. The CPU can constitute a single core or multiple core processor that executes parallel processes simultaneously. For example, the CPU can be a single core processor that is configured with virtual processing technologies. The CPU can use logical processors to simultaneously execute and control multiple processes.

The controller 1500 can include a memory 1560. The memory 1560 can be in communication with the one or more processors (e.g., the CPU). The memory 1560 can include instructions, for example a program 1580 or other application, that causes the the CPU and/or controller 1500 to complete any of the processes described herein. For example, the memory 1560 can include instructions that cause the controller 1500 and/or the CPU to receive an activation signal (e.g., from a manual trigger, from an external user device, from a display screen of user interface 87, etc.), output a control signal (e.g., a control signal to the motor and/or piston associated with actuating urging of solution from a respective cartridge through a respective nozzle) to actuate to deliver fluid from the syringe 70, 270, 370, 470, 570, output a control signal to a switch to provide voltage from the voltage supply of HV module 86 to the respective voltage wire (e.g., wire 92*d*).

The memory 1560 can include, in some implementations, one or more suitable types of memory (e.g., volatile or non-volatile memory, random access memory (RAM), read only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like), for storing files including an operating system, application programs, executable instructions and data. The memory 1560 can also include a program, e.g., program 1580, that includes the instructions to complete the processes described herein. For example, the program 1580 can include instructions to receive the activation signal (e.g., from actuator of applicator 100, or a virtual trigger, for example from an external user device and/or from the display screen of user interface 87), output a first control signal to the motor to actuate a piston associated with actuating a respective cartridge, and/or output a second control signal to a switch to provide voltage from the voltage supply of HV module 86 to the voltage wire. Further, the controller 1500 can include data storage 1590 that can store data associated with, for example, the parameters in which to adjust the air flow, fluid flow, and/or voltage for the particular treatment solution.

Figure 18:
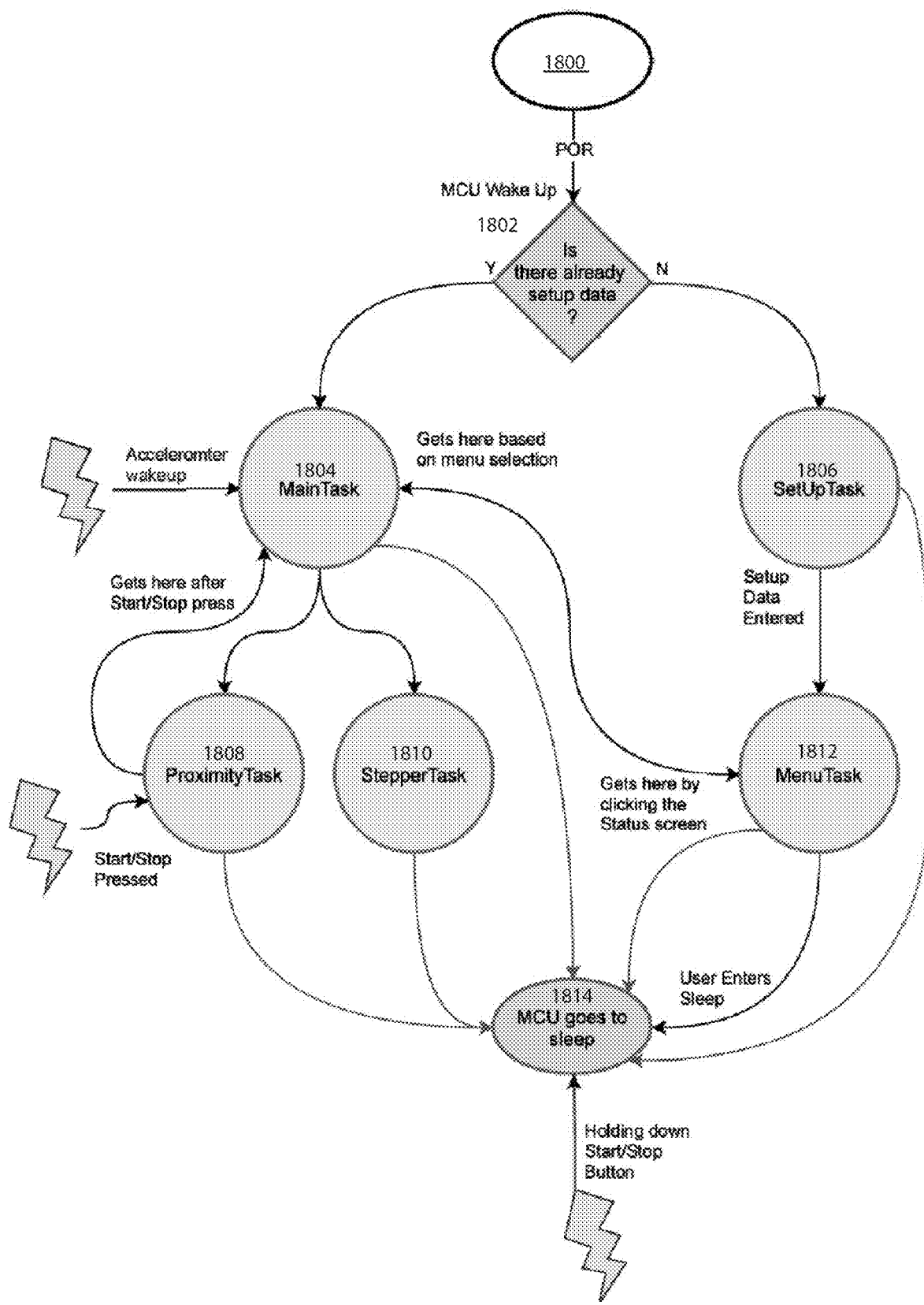
FIG. 18 is a flow diagram of example processes for operating the electrostatic applicator and disposable cartridge system, according to the present disclosure.

FIGS. 18-21 are flow diagrams of example processes for operating a reusable applicator 100/disposable cartridge 50, 250, 350, 450, 550 system, according to the present disclosure. Specifically, FIG. 18 is a flow chart of an exemplary process 1800 to manage operations of the herein described applicator 100. In process 1800, the microcontroller unit can wake up to determine if setup data is present (step 1802). If yes, then applicator 100 system can be woken to execute the main task process (step 1804). The main task process of step 1804 can include proximity task step 1808, stepper motor task 1810, menu task 1812, and MCU sleep mode 1814. In some aspects, main task of step 1804 can be initiated upon detecting of input from an accelerometer in communication therewith (e.g., in response to detecting a predetermined change in acceleration above a threshold indicative of user movement of applicator 100). In some aspects, proximity task 1808 can be initiated when a corresponding proximity sensor (e.g., target sensor 45) detects that a target site is within a threshold sprayer range of applicator 100. In some aspects, proximity task step 1808 can be initiated by starting and/or stopping actuation of an associated actuator (e.g., a button or capacitive input of the display screen of user interface 87).

If in step 1802 the system determines that there is no setup data present, then step 1806 of the setup task of applicator 100 is executed. In some aspects, step 1806 can include setup data being entered (e.g., via a display screen of user interface 87). Upon setup data being entered, menu task 1812 can be executed. If actuation or other input has not been received within a predetermined time period, then in step 1814 the system will enter the MCU sleep mode.

Figure 19:
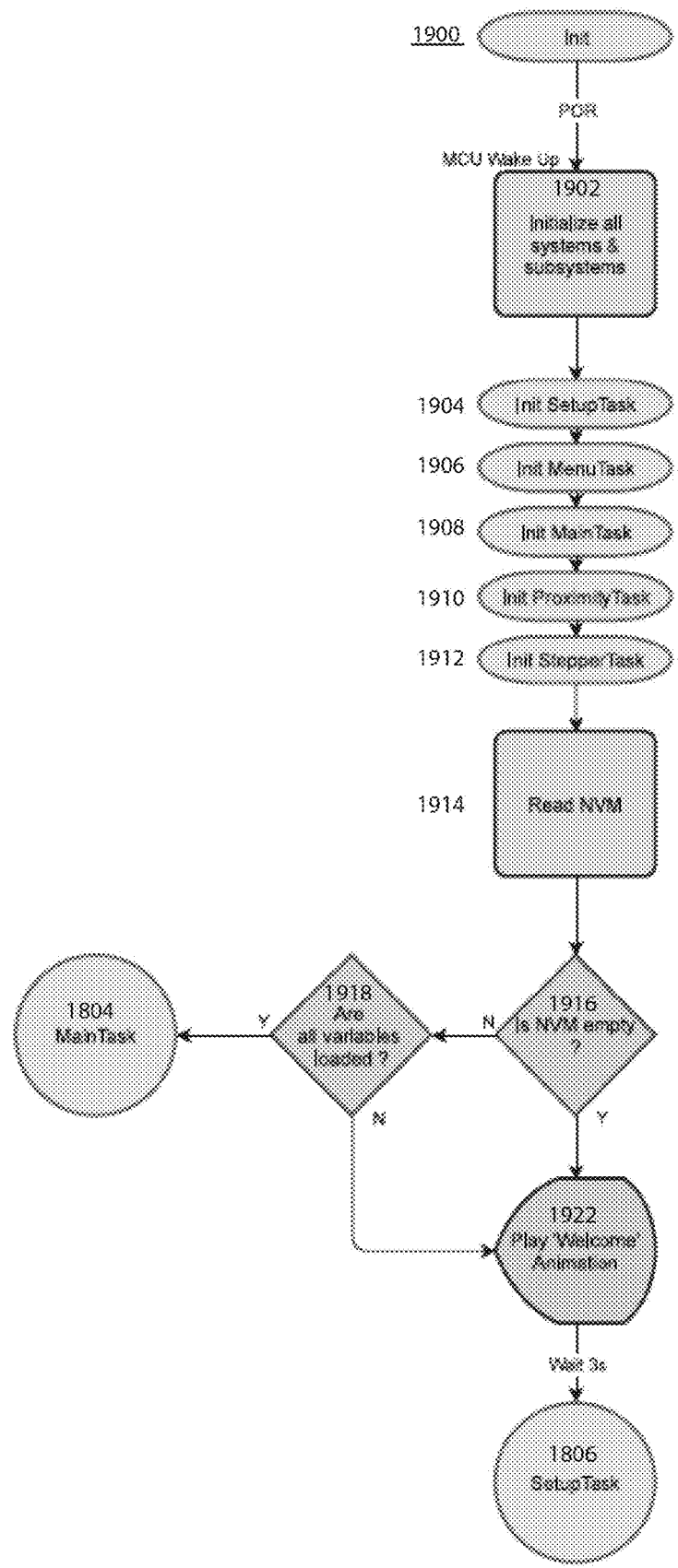
FIG. 19 is a flow diagram of example processes for operating the electrostatic applicator and disposable cartridge system, according to the present disclosure.

FIG. 19 is a flow chart of an exemplary process 1900 utilizing certain aspects from process 1800. In process 1900, the microcontroller unit can wake up to initialize all systems and subsystems of applicator 100 (step 1902). Such initializing can include initiating setup tasks 1904, menu tasks 1906, main tasks 1908, proximity tasks 1910, stepper motor task 1912, as well as other initializing tasks. After completing step 1902, then the step of reading non-volatile memory 1914 is executed and if the non-volatile memory is not empty (step 1916), then the system will determine whether all variables are loaded (step 1918). If all variables are loaded, then the previously discussed main task 1804 of process 1800 can be performed. If the non-volatile memory is empty in step 1916, then the system can play a welcome animation on the display screen of interface 87 (step 1922). Similarly, if it is determined in step 1918 that all variables are not loaded, then step 1922 can similarly be executed by the system. Upon completion of step 1922 in either context and after waiting a predetermined period of time (e.g., approximately 3 seconds), previous setup task step 1806 from process 1800 can be executed.

Figure 20:
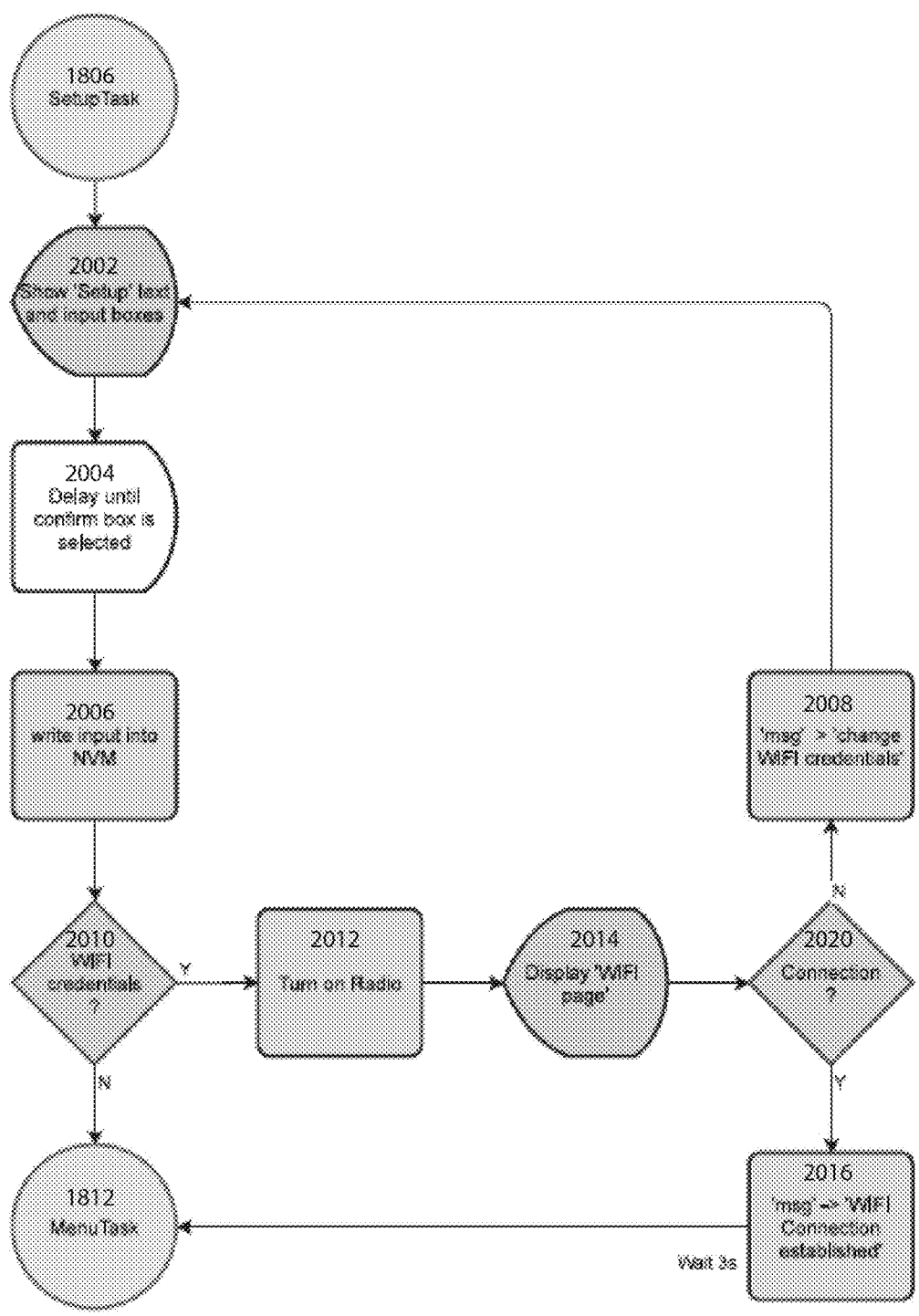
FIG. 20 is a flow diagram of example processes for operating the electrostatic applicator and disposable cartridge system, according to the present disclosure.

FIG. 20 is a flow chart of an exemplary process setup task 1806 of previous process 1800 as to initiating wireless connectivity between an example applicator 100 and a wireless network.

Figure 21:
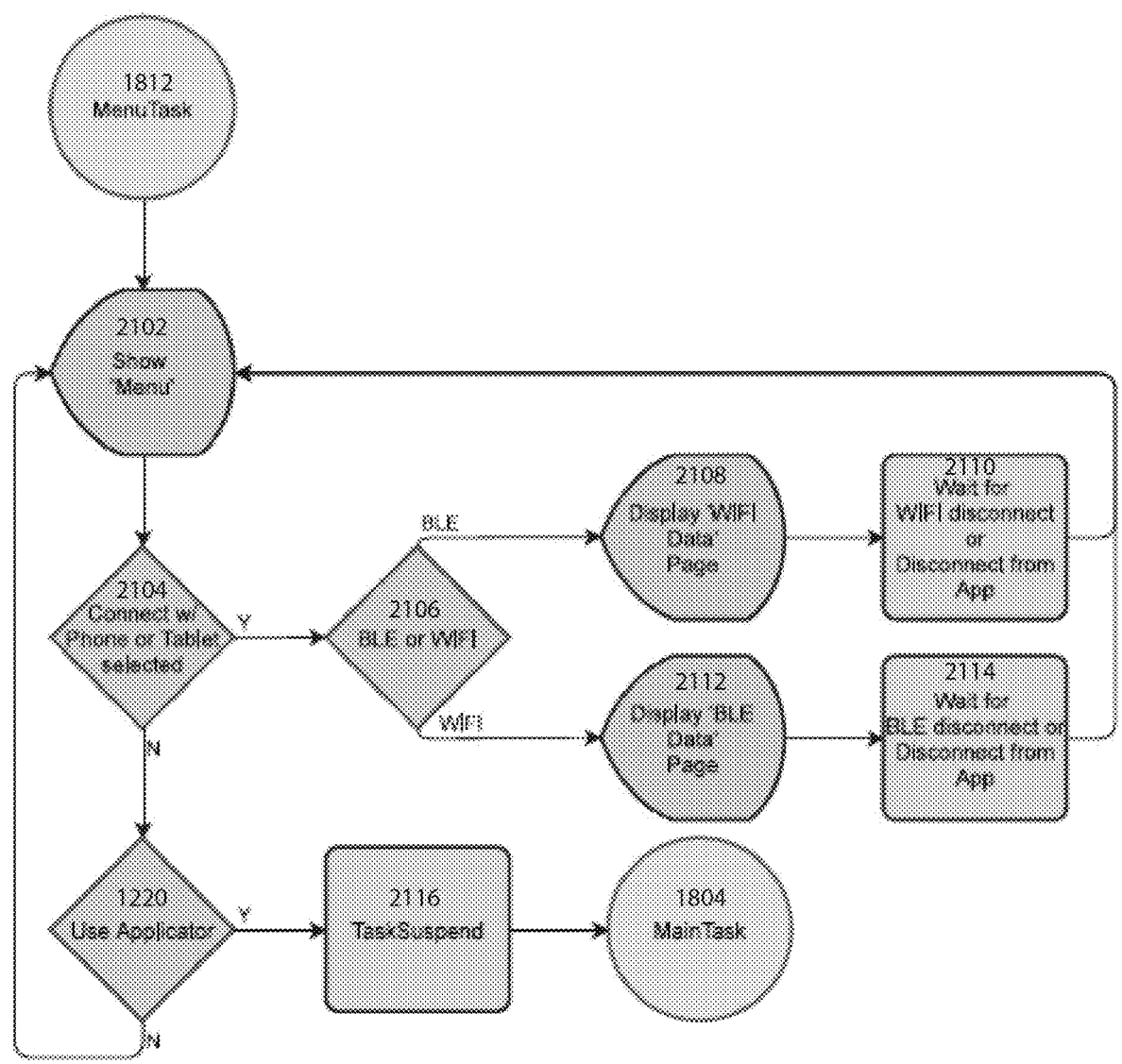
FIG. 21 is a flow diagram of example processes for operating the electrostatic applicator and disposable cartridge system, according to the present disclosure.

FIG. 21 is a flow chart of an exemplary process setup task 1812 of previous process 1800 as to initiating wireless connectivity between an example applicator 100 and an external device so that the external device (e.g., a mobile computing device such as a smart phone, a tablet, etc.), can control and/or monitor one or more operations of aspects of the applicator 100, including but not limited to operations of a cartridge coupled thereto.

Figure 22:
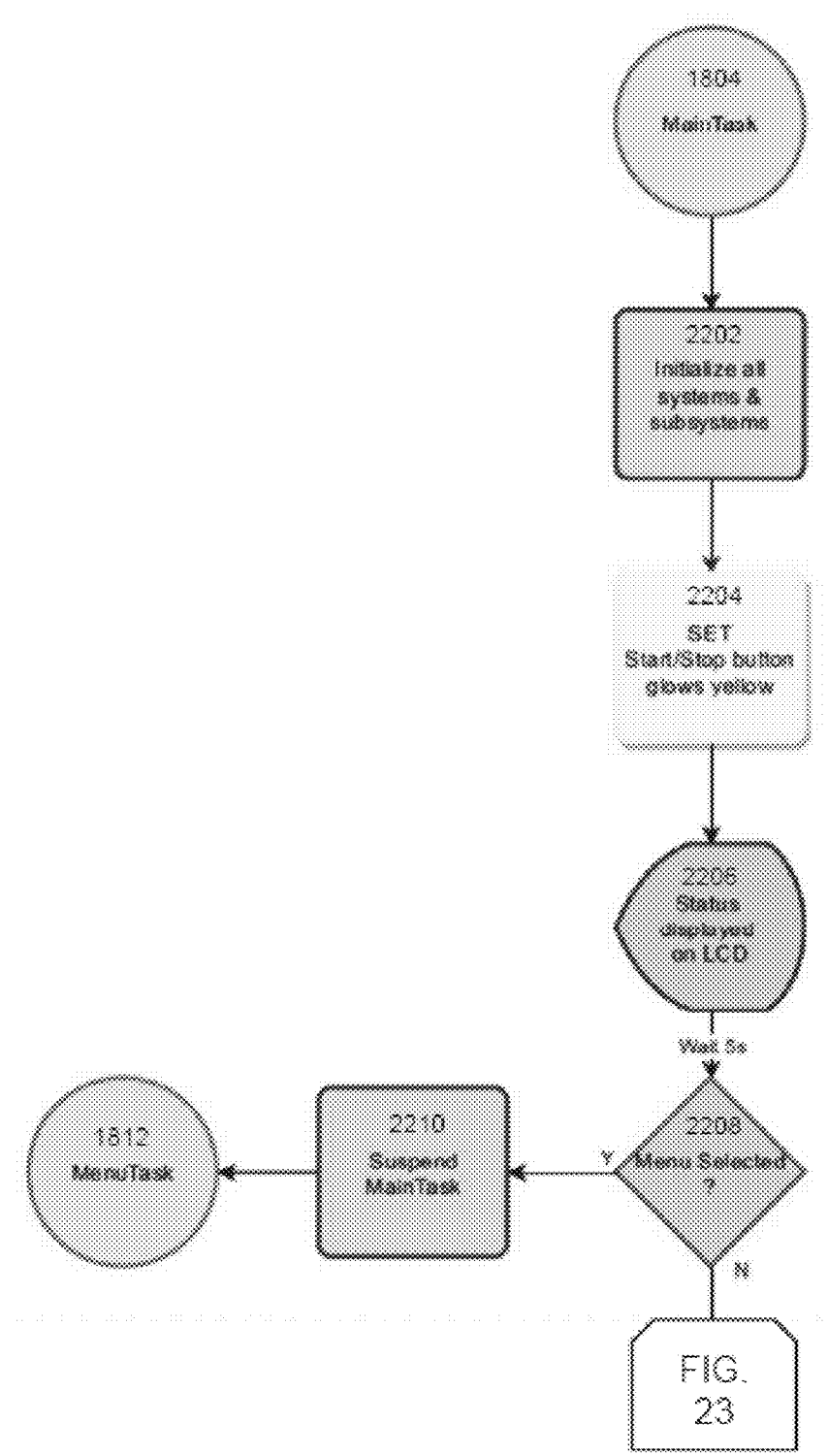
FIG. 22 is a flow diagram of example processes for operating the electrostatic applicator and disposable cartridge system with interactive components that provide feedback to a user regarding the status of the device, according to the present disclosure.
Figure 23:
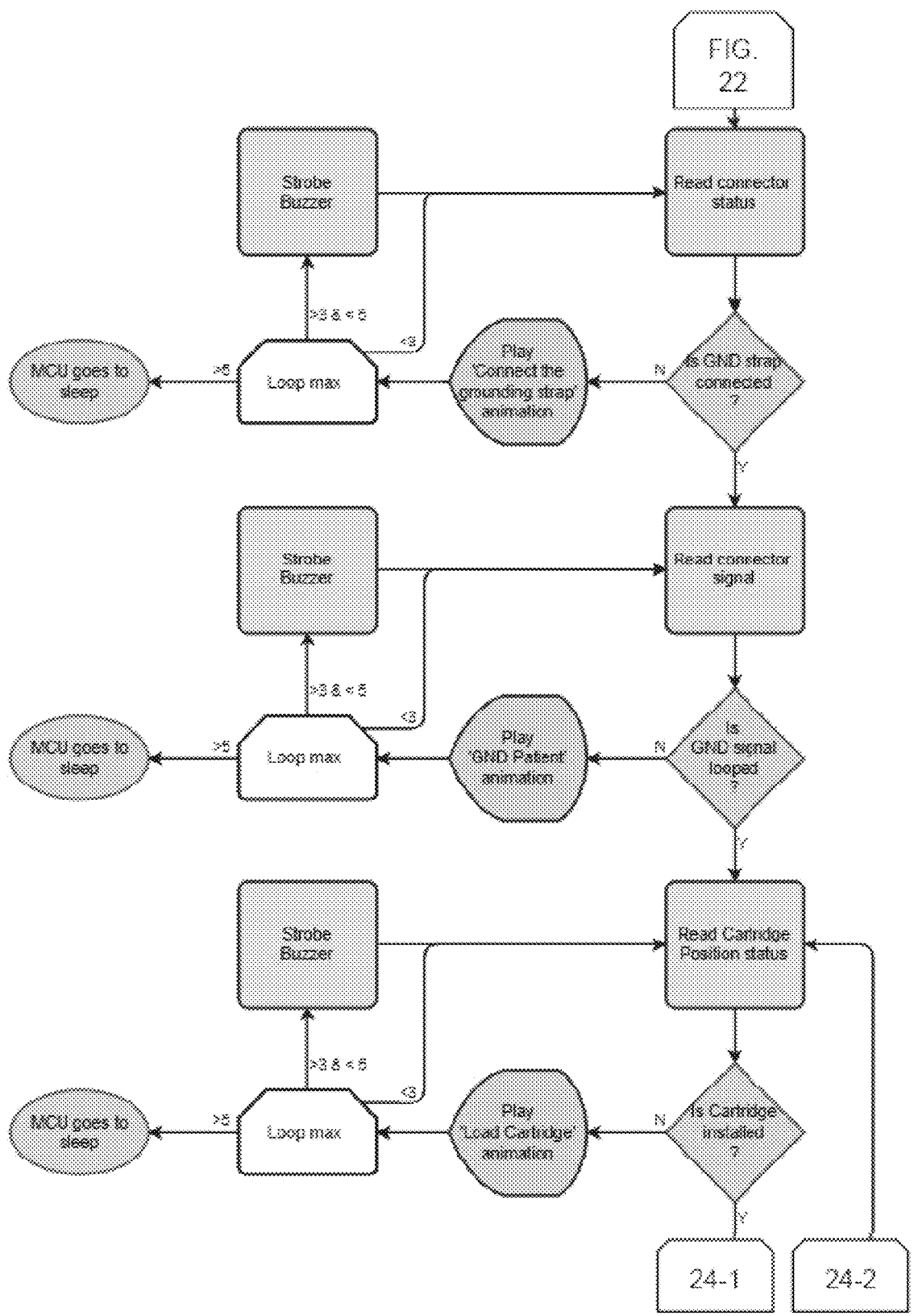
FIG. 23 is a flow diagram of example processes for operating the electrostatic applicator and disposable cartridge system with interactive components that provide feedback to a user regarding the status of the device, according to the present disclosure.
Figure 24:
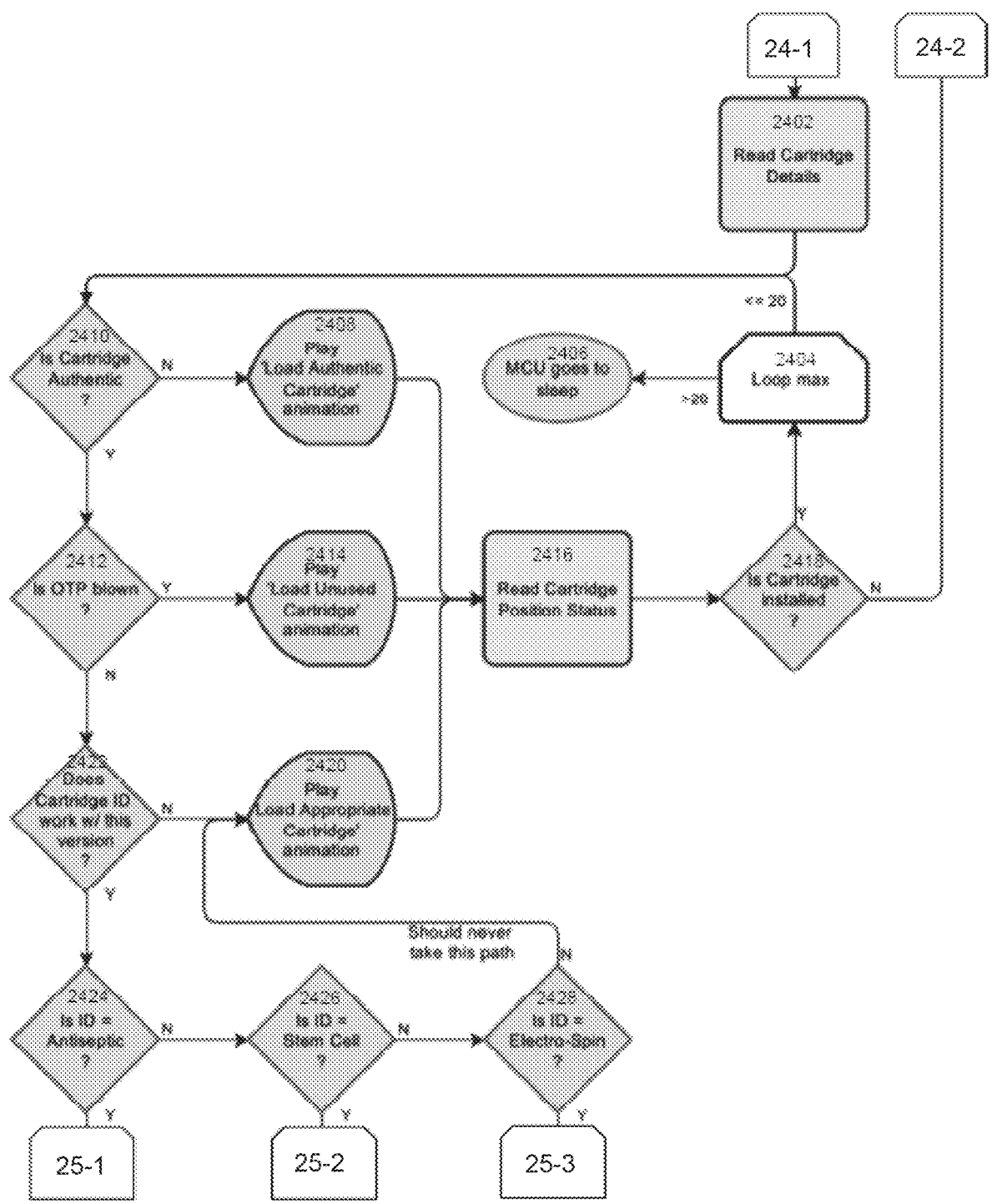
FIG. 24 is a flow diagram of example processes for operating the electrostatic applicator and disposable cartridge system with interactive components that provide feedback to a user regarding the status of the device, according to the present disclosure.

FIG. 22 is a flow chart of an exemplary process main task 1804 of previous process 1800 as to initializing all systems and subsystems of an example applicator 100. FIG. 23 is a flow chart that continues from FIG. 22 and specifically described example substeps related to determining and managing operations related to a ground strap and any related ground signal, in those examples where a ground strep is present. FIGS. 23 and 24 also describes exemplary steps related to operations of loading and managing assembly of any heretofore described cartridge with the example applicator 100 of this disclosure. For example and without limitation, in step 2330 of FIG. 23, the cartridge position can be analyzed to determine whether it has been properly installed. If not, then an animation can be played (step 2332) until ultimately the MCU can cause a sleep mode to execute (step 2336). If the cartridge is determined to be properly installed (step 2330), then in step 2402 cartridge details can be read to determine certain information, including if the cartridge is authentic (step 2410), whether the OTP is blown (step 2412), whether the cartridge identification is compliant or able to work with the current firmware and/or hardware of applicator 100 (step 2422), whether the cartridge ID is indicative of the contents thereof being antiseptic (step 2424), including stem cells (step 2426), and/or being configured for electrospinning (step 2428). Other aspects of a respective cartridge can also be identified and evaluated in these example processes. For example, other solution types can be analyzed as well as cartridge origin and destination, whether its contents remain fully sealed, whether the cartridge has been loaded into the applicator previously, a prescribing entity (e.g., whether a doctor or other operator has requested the cartridge), whether the cartridge is associated with a particular patient or intended application.

Figure 25:
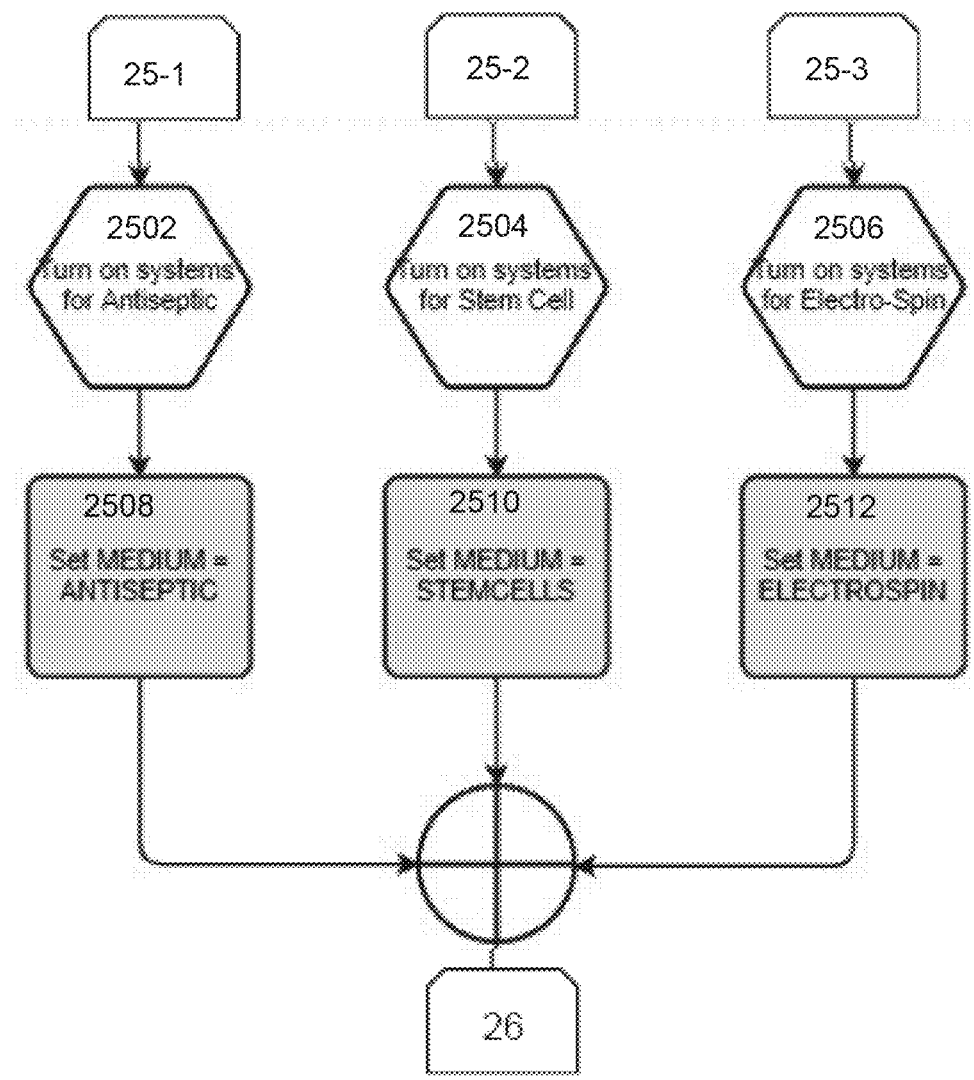
FIG. 25 is a flow diagram of example processes for operating the electrostatic applicator and disposable cartridge system with interactive components that provide feedback to a user regarding the status of the device, according to the present disclosure.
Figure 26:
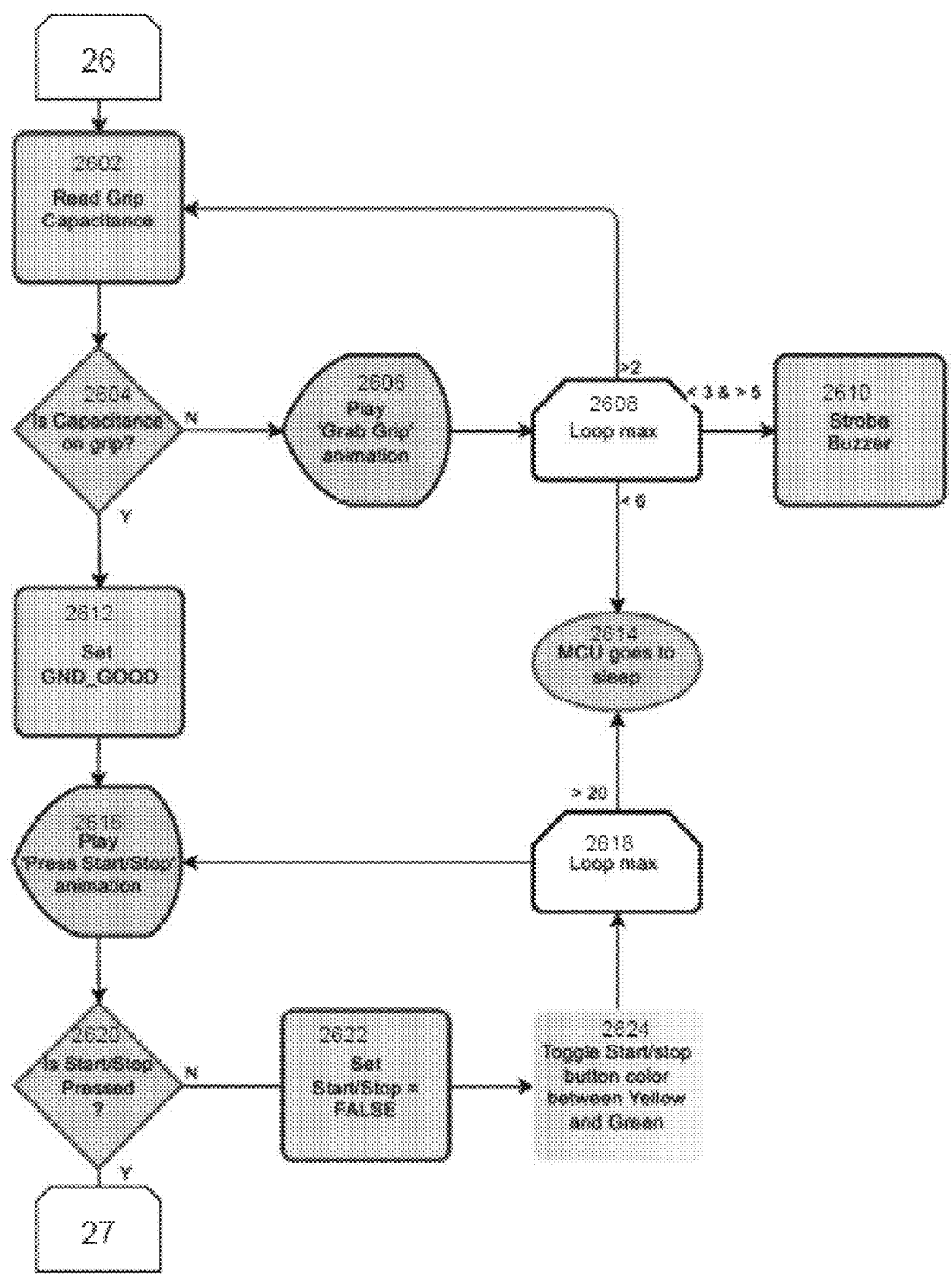
FIG. 26 is a flow diagram of example processes for operating the electrostatic applicator and disposable cartridge system with interactive components that provide feedback to a user regarding the status of the device, according to the present disclosure.
Figure 27:
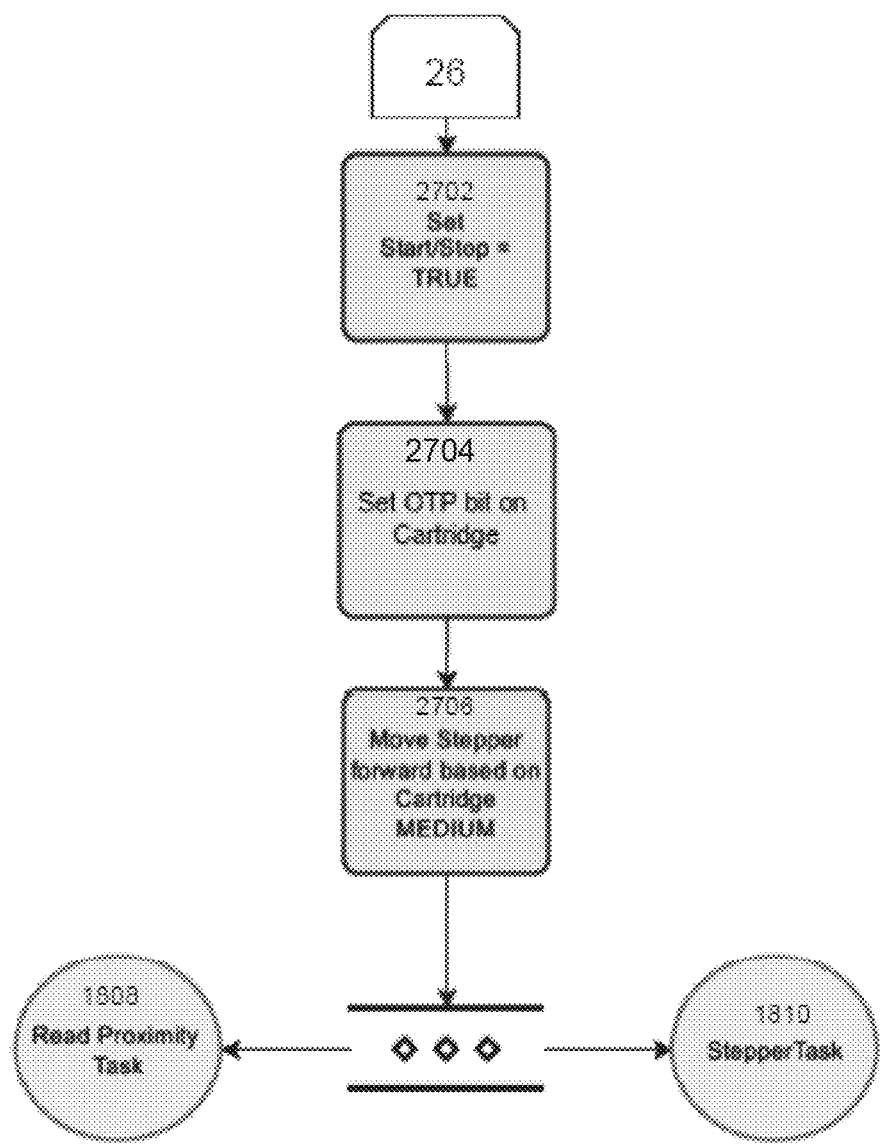
FIG. 27 is a flow diagram of example processes for operating the electrostatic applicator and disposable cartridge system with interactive components that provide feedback to a user regarding the status of the device, according to the present disclosure.

Depending on the result of certain substeps in FIG. 24, then the system can move to the process of FIG. 25 whereby steps 2502 (system settings for antiseptic mediums), 2504 (system settings for stem cell mediums), 2506 (system settings for electrospinning mediums) can initiate system settings in steps 2508, 2510, 2512, respectively, and then proceed with remaining operational tasks previously described in process 1800 of FIG. 18, as further illustrated in FIGS. 26 and 27. For example, in FIG. 27, start/stop can be set (step 2702), the OTP bit on the cartridge loaded with the applicator 100 can be set (step 2704), and then the stepper of the applicator can be moved forward depending on the contents (i.e. the medium of the contents of the respective cartridge) (step 2706). Then, the proximity task 1808 can be read and if satisfactory, then the stepper task 1810 can be executed. In some aspects, the result of proximity task 1808 can be presented on a display screen of interface 87 and/or presented in one or more LEDs associated therewith.

Figure 28:
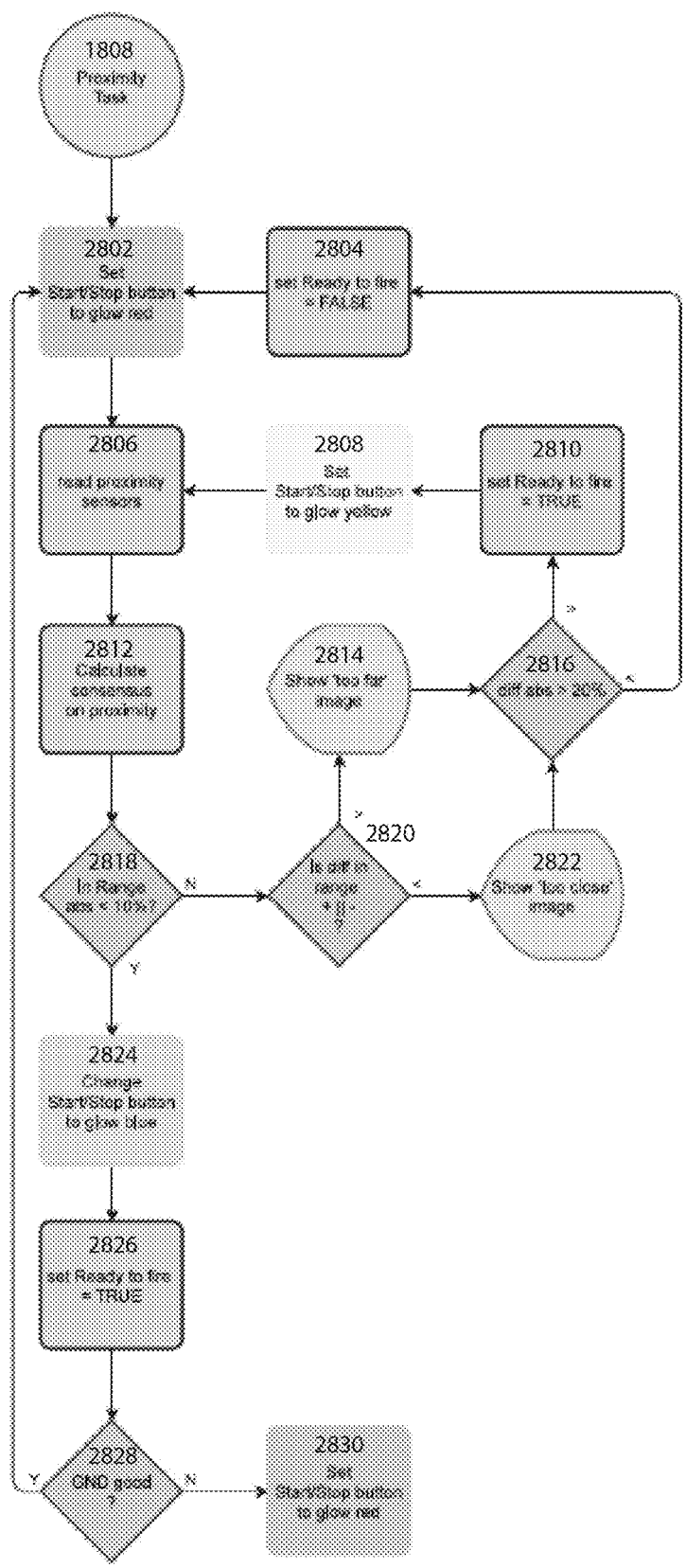
FIG. 28 is a flow diagram for using a proximity sensor to provide feedback to a user regarding optimal applicator and disposable cartridge system positioning, according to the present disclosure.

FIG. 28 is a flow chart of an exemplary process proximity task 1808 of previous process 1800 as to sensing and managing operations based on readings and related calculations from one or more proximity sensor of the applicator 100.

Figure 29:
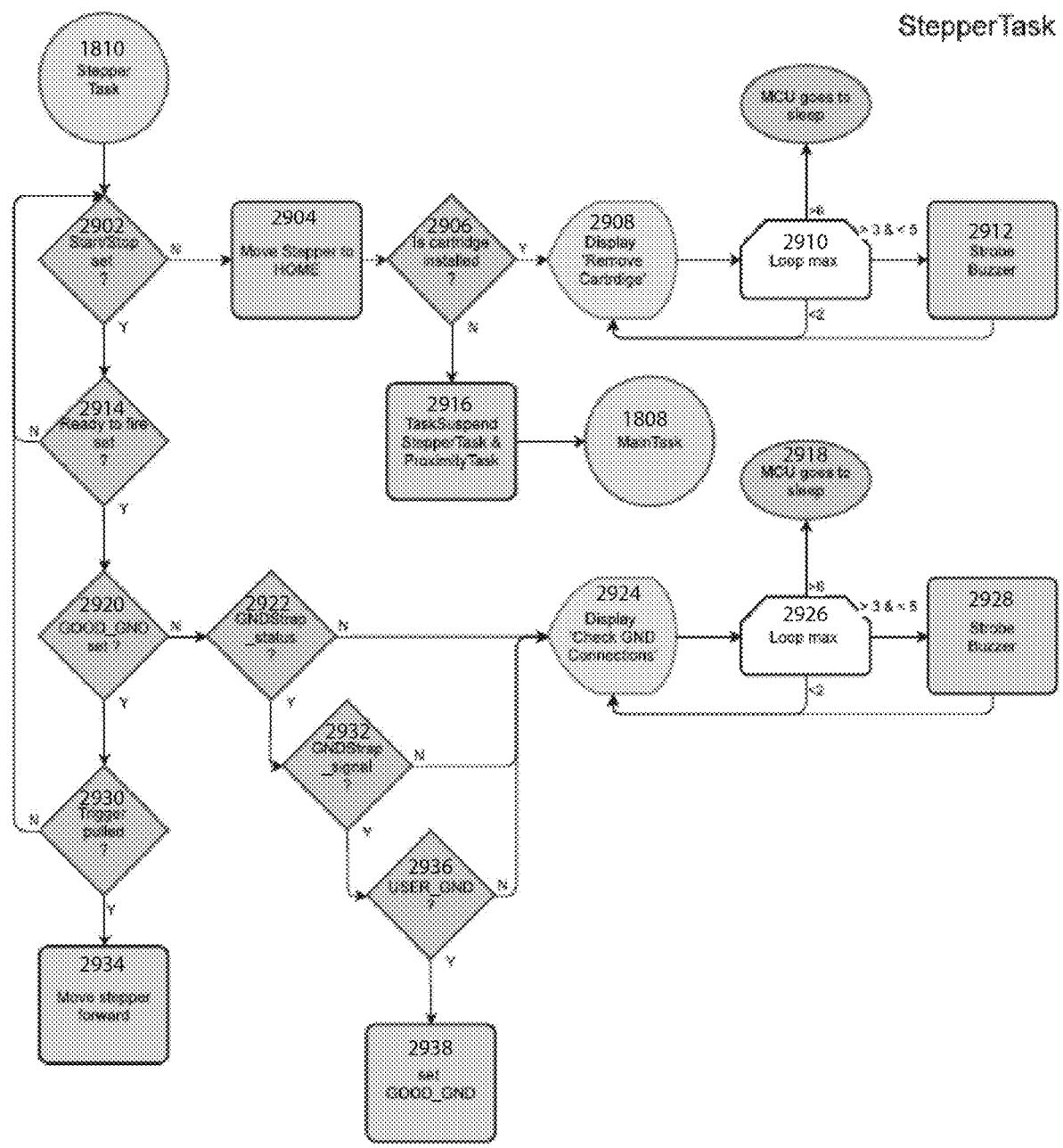
FIG. 29 is a flow diagram for operating an example applicator and disposable cartridge system, according to the present disclosure.

FIG. 29 is a flow chart of an exemplary process stepper task 1810 of previous process 1800 as to operations of the stepper motor of the applicator 100 in connection with emitting contents from a cartridge loaded therewith towards a target site.

Figure 30:
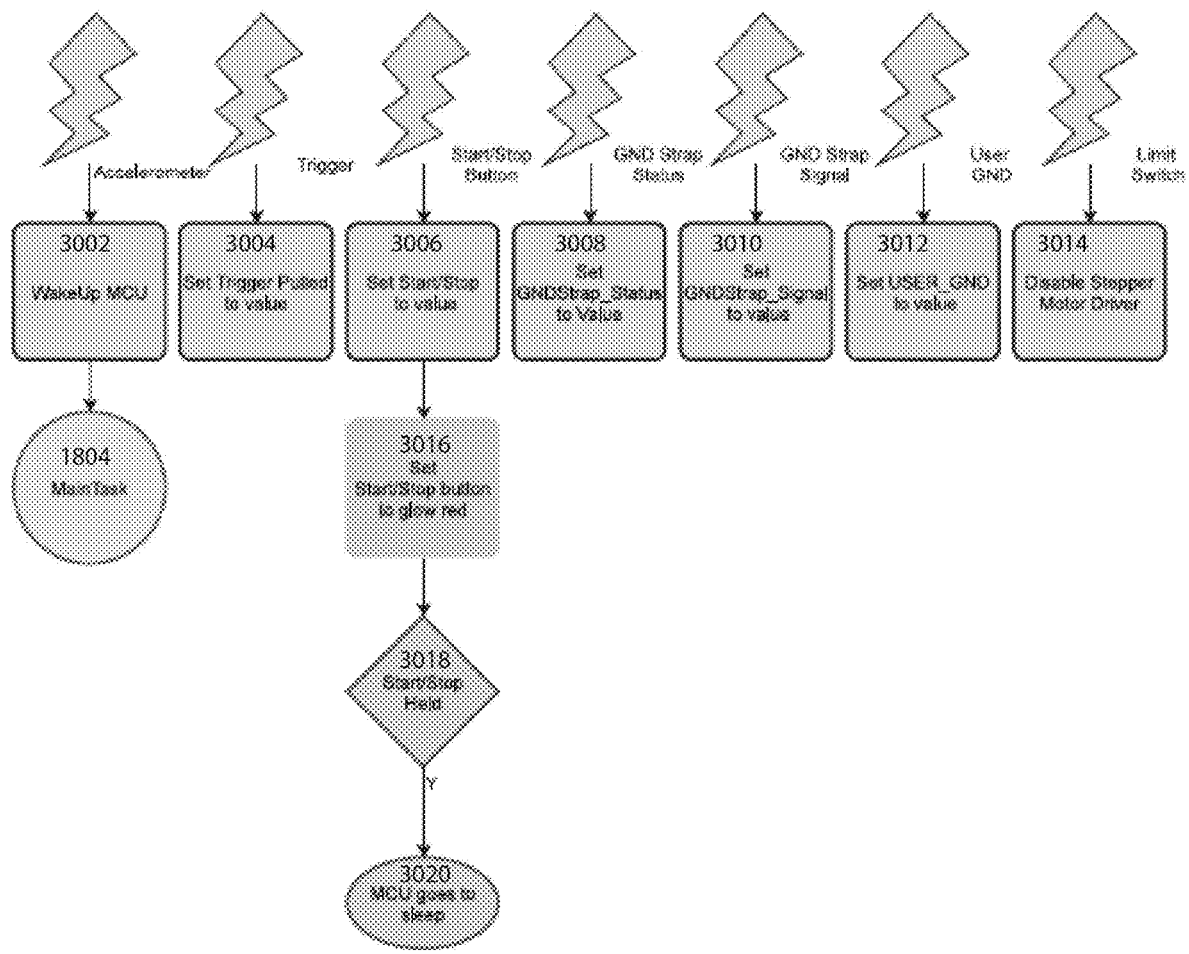
FIG. 30 is a flow diagram for operating an example applicator and disposable cartridge system, according to the present disclosure.

FIG. 30 is a flow chart of an exemplary processes which can be used to prior to executing main task 1804 and/or having the MCU enter a sleep mode (step 3020). For example, processes can include managing feedback from an accelerometer, manual trigger, actuation of a start/stop button, status of a ground strap, signal from a ground strap, presence of a user ground, as well as feedback from a limit switch.

FIG. 31 is a flow diagram for a method 3100 of operating an example electrostatic applicator system. Step 3110 of method 3100 can include inserting a first disposable cartridge into a chamber housing of the electrostatic applicator system such that a voltage contact at a first end of a voltage wire within the first disposable cartridge contacts a voltage contact of the electrostatic applicator system; a first end of an air supply port within the first disposable cartridge fluidly connects with an air supply port of the electrostatic applicator system; and a plunger of a syringe within the first disposable cartridge aligns with a piston of the electrostatic applicator system, the syringe containing a first fluid. Step 3120 of method 3100 can include causing, by an activation input to the electrostatic applicator system, a motor to actuate and a voltage potential to be delivered to a delivery tube of the first disposable cartridge.

FIG. 32 is a computer-implemented method 3200 for operating an electrostatic applicator system. Step 3210 of method 3200 can include causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a chamber housing of the electrostatic applicator system. Step 3220 of method 3200 can include advancing, by the motor urging a stopper of the syringe, fluid contents of the disposable cartridge from the syringe through the delivery tube. Step 3230 of method 3200 can include electrostatically charging, by the voltage wire, the fluid contents while in the delivery tube. Step 3240 of method 3200 can include emitting the electrostatically charged fluid contents from a nozzle assembly of the disposable cartridge onto a treatment site.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

The following clauses list non-limiting embodiments of the disclosure:

1. A disposable fluid delivery system for an electrostatic applicator, including:
   a nozzle housing including an air supply port, a voltage port, and a delivery outlet;
   a voltage wire including a contact in communication with a delivery tube in fluid communication with the delivery outlet, the voltage wire configured to be in electrical communication with a high voltage module and electrostatically charge fluid contents within the delivery tube;
   a syringe including a barrel portion and a plunger configured to advance fluids from within the barrel portion and through the delivery tube; and
   a cartridge housing at least partially enclosing the nozzle housing, the voltage wire, and the syringe.

2. The disposable fluid delivery system of Clause 1, further including a voltage tube in electrical communication with the voltage port, wherein the voltage wire runs between the contact in communication with the delivery tube and a contact port of a wall of the cartridge housing.

3. The disposable fluid delivery system of Clause 2, wherein the voltage tube and the voltage wire include a substantially S-shape.

4. The disposable fluid delivery system of Clause 2, wherein the voltage tube and the voltage wire include a linear shape.

5. The disposable fluid delivery system of Clause 2, wherein the voltage tube and the voltage wire include a substantially curved shape.

6. The disposable fluid delivery system of Clause 2, further including an air supply tube connected to the air supply port.

7. The disposable fluid delivery system of Clause 2, wherein the syringe contains contents including one or more of an antiseptic, a disinfectant solution, an analgesic, an exosome, a biologic, and/or a liquid bandage solution.

8. The disposable fluid delivery system of Clause 2, wherein the analgesic includes one or more of lidocaine, levobupivacaine, acemetacin, ketorolac, and ceftazidime.

9. The disposable fluid delivery system of Clause 2, wherein the biologic includes one or more of stem cells and/or mammalian cells.

10. The disposable fluid delivery system of Clause 2, wherein the antiseptic and/or disinfectant solution includes chlorohexidine gluconate and/or povidone-iodine.

11. The disposable fluid delivery system of Clause 1, wherein the cartridge housing is a moldable plastic material.

12. The disposable fluid delivery system of Clause 11, wherein the cartridge housing includes a plurality of sections of moldable plastic connectable to create a single integrated component.

13. The disposable fluid delivery system of Clause 1, wherein the contact of the voltage wire includes a wire loop at least partially surrounding an outer surface of the delivery tube to provide a voltage potential of approximately 1 V to approximately 40 kV.

14. The disposable fluid delivery system of Clause 1, wherein the contact of the voltage wire is in physical contact with an outer surface of the delivery tube to provide a voltage potential of approximately 1 V to approximately 40 kV.

15. The disposable fluid delivery system of Clause 1, wherein the delivery tube, when assembled with the syringe and the nozzle housing, is configured to receive air from the air supply port and fluid from the barrel portion of the syringe and expel fluid equally charged by the voltage wire.

16. The disposable fluid delivery system of Clause 1, further including:
   a reusable electrostatic applicator including a cartridge chamber sized and shaped to accept the cartridge housing, the reusable electrostatic applicator including:
   a high voltage module configured to be in in electrical communication with the voltage wire; and
   a piston positioned proximate the cartridge chamber and configured to advance the plunger enclosed in the cartridge housing when the cartridge housing is assembled with the cartridge chamber.

17. The disposable fluid delivery system of Clause 16, wherein the reusable electrostatic applicator includes:
   a motor configured to move the piston;
   one or more processors; and
   memory storing instructions that, when executed by the one or more processors, causes the reusable electrostatic applicator to:
   receive an activation signal;
   output a control signal to the motor to actuate the piston; and
   output a control signal to a switch to provide voltage from the high voltage module to the voltage wire.

18. The disposable fluid delivery system of Clause 17, the motor being a stepper motor, a linear actuator, a worm gear motor, and/or a planetary gear motor.

19. The disposable fluid delivery system of Clause 17, the motor being a drivable actuator system using a kinetic transfer with applied force.

20. The disposable fluid delivery system of Clause 17, wherein the reusable electrostatic applicator further includes a display screen, and wherein the activation signal is a user input into the display screen.

21. The disposable fluid delivery system of Clause 17, wherein the reusable electrostatic applicator further includes an actuator, and wherein the activation signal is user input received by the actuator.

22. The disposable fluid delivery system of Clause 21, wherein the reusable electrostatic applicator includes:
   a housing base including a voltage source;
   a device housing including the cartridge chamber; and
   a handle extending between the base and the device housing.

23. The disposable fluid delivery system of Clause 22, wherein the cartridge chamber is positioned within the device housing such that the actuator is positioned below the cartridge chamber with respect to horizontal.

24. The disposable fluid delivery system of Clause 17, wherein the reusable electrostatic applicator further includes a wireless antenna, and wherein the activation signal is a wireless signal received from a remote external user device.

25. An electrostatic applicator system for delivering a treatment solution to a target site, including:
a portable reusable electrostatic applicator including:
a device housing configured to be handheld;
a motor in the device housing configured to drive a piston;
a voltage source in the device housing;
a high voltage module electrically connected to the voltage source; and
a cartridge chamber; and
a disposable cartridge removably insertable in the cartridge chamber, the disposable cartridge including:
a nozzle housing including an air supply port, a voltage port, and a delivery outlet;
a voltage wire including a contact in communication with a delivery tube in fluid communication with the delivery outlet;
a syringe including a barrel portion and a plunger configured to advance fluids from within the barrel portion and through the delivery tube; and
a cartridge housing at least partially enclosing the nozzle housing, the voltage wire, and the syringe.

26. The electrostatic applicator system of Clause 25, wherein the syringe contains the fluid including one or more of an antiseptic, a disinfectant solution, an analgesic, an exosome, a biologic, and/or a liquid bandage solution.

27. The electrostatic applicator system of Clause 26, wherein the analgesic includes one or more of lidocaine, levobupivacaine, acemetacin, ketorolac, and ceftazidime.

28. The electrostatic applicator system of Clause 26, wherein the biologic includes one or more of stem cells and/or mammalian cells.

29. The electrostatic applicator system of Clause 25, wherein the voltage wire and a voltage tube including the voltage wire in the cartridge housing includes a linear shape and/or a curved shape or a substantially S-shape.

30. The electrostatic applicator system of Clause 25, wherein the cartridge housing is a moldable plastic material.

31. The electrostatic applicator system of Clause 30, wherein the cartridge housing includes a plurality of connected sections of moldable plastic.

32. The electrostatic applicator system of Clause 25, wherein the cartridge chamber includes a wall including a high voltage contact in electrical communication with the high voltage module and an air supply port in fluid communication with a pump positioned in the device housing;
wherein the voltage wire is in electrical communication with the high voltage contact of the wall; and
wherein the contact of the voltage wire is in physical contact with an outer surface of the delivery tube to provide a voltage potential of approximately 1 V to approximately 40 kV.

33. The electrostatic applicator system of Clause 25, wherein the delivery tube, when assembled with the syringe and the nozzle housing, is configured to receive air from the air supply port and fluid from the barrel portion of the syringe and expel fluid equally charged by the voltage wire.

34. The electrostatic applicator system of Clause 25, wherein the disposable cartridge comprises an air supply tube connected to the air supply port.

35. The electrostatic applicator system of Clause 25, wherein the device housing includes a handle and the voltage source is disposed within a housing base of the device housing, and wherein the handle is disposed between the device housing and the base.

36. The electrostatic applicator system of Clause 25, wherein the reusable electrostatic applicator includes:
one or more processors; and
memory storing instructions that, when executed by the one or more processors, causes the reusable electrostatic applicator to:
receive an activation signal; and
output a control signal to a motor controlling (a) a voltage potential from the high voltage module to the delivery tube via the voltage wire, (b) a position of the piston and the plunger of the disposable cartridge, and/or (c) a pump regulating air flow from the device housing into the air supply port.

37. The electrostatic applicator system of Clause 36, wherein the disposable cartridge includes an integrated memory including information related to one or more operational parameters of contents stored within the syringe and/or another fluid reservoir of the disposable cartridge, wherein the one or more processors of the reusable electrostatic applicator are configured to communicate with the integrated memory to retrieve information related to the contents of the disposable cartridge and control at least one of a flow rate, a voltage potential, and a nozzle setting.

38. The electrostatic applicator system of Clause 36, wherein the disposable cartridge includes an integrated memory including information related to characteristics of contents stored within the syringe and/or another fluid reservoir of the disposable cartridge, wherein the one or more processors of the reusable electrostatic applicator are configured to communicate with the integrated memory to retrieve information related to the contents of the disposable cartridge and control a motor speed, an intake of air, and/or an applied voltage.

39. The electrostatic applicator system of Clause 37, wherein the memory is embedded in a processor of the electrostatic applicator system and includes operation instructions for operating the electrostatic applicator system.

40. The electrostatic applicator system of Clause 37, wherein a near field communication (NFC) tag includes the memory.

41. The electrostatic applicator system of Clause 40, further including a display screen, and wherein the activation signal is a user input into the display screen.

42. The electrostatic applicator system of Clause 40, further including a display screen, wherein the instructions further comprise:
reading information of the NFC related to operational parameters of the disposable cartridge; and
presenting the read information of the NFC in the display screen.

43. The electrostatic applicator system of Clause 36, further including an actuator, and wherein the activation signal is user input received by the actuator.

44. The electrostatic applicator system of Clause 36, further including a wireless antenna, and wherein the activation signal is a wireless signal received from an external user device.

45. The electrostatic applicator system of Clause 36, further including an accelerometer configured to output a movement signal to the one or more processors in response to detecting movement of the electrostatic applicator system.

46. The electrostatic applicator system of Clause 45, further including a display screen on the electrostatic applicator system activated by a wake signal from the one or more processors in response to the one or more processors receiving the movement signal; and wherein the activation signal is a user input into the display screen.

47. The electrostatic applicator system of Clause 36, wherein the electrostatic applicator system further includes a proximity sensor configured to detect a distance between the system and an intended target;
  wherein one of the control signals is output to the motor in response to the distance being within a predetermined distance threshold; and
  wherein one of the control signals is output to a switch to control voltage of the electrostatic applicator system in response to the distance being within the predetermined distance threshold.

48. The electrostatic applicator system of Clause 36, wherein the electrostatic applicator system further includes a proximity sensor configured to detect a distance between the system and an intended target, wherein one of the control signals is output to prevent operations of the motor in response to the distance being greater than or less than a predetermined distance threshold.

49. The electrostatic applicator system of Clause 36, wherein the electrostatic applicator system further includes a proximity sensor configured to detect a distance between the system and an intended target, wherein one of the control signals is output to a switch to prevent delivery of voltage of the electrostatic applicator system in response to the distance being greater than or less than a predetermined distance threshold.

50. A method for operating an electrostatic applicator system, including:
  inserting a first disposable cartridge into a chamber housing of the electrostatic applicator system such that:
  a voltage contact at a first end of a voltage wire within the first disposable cartridge contacts a voltage contact of the electrostatic applicator system;
  a first end of an air supply port within the first disposable cartridge fluidly connects with an air supply of the electrostatic applicator system; and
  a plunger of a syringe within the first disposable cartridge aligns with a piston of the electrostatic applicator system, the syringe containing a first fluid; and
  causing, by an activation input to the electrostatic applicator system, a motor to actuate and a voltage potential to be delivered to a delivery tube of the first disposable cartridge.

51. The method of Clause 50, wherein actuating the motor causes the first fluid to advance from the syringe through the delivery tube and be sprayed as atomized electrostatically charged fluid droplets in a predetermined spray pattern onto a target site.

52. The method of Clause 50, further including:
  removing the first disposable cartridge from the chamber housing; and
  inserting a second disposable cartridge into the chamber housing, wherein the second disposable cartridge contains a second fluid.

53. The method of Clause 52, wherein the second disposable cartridge is configured for electrospinning, the method further including:

causing, by a second activation input to the electrostatic applicator system, a motor to actuate and a voltage potential delivered to a delivery tube of the second disposable cartridge so that the second fluid of a syringe of the second disposable cartridge is delivered by a delivery tube of the second disposable cartridge as an electrospun fiber from the second fluid to a target site.

54. The method of Clause 52, wherein the first disposable cartridge and the second disposable cartridge each include an integrated memory including information related to operational parameters of the first fluid and the second fluid, respectively, and wherein inserting either the first disposable cartridge or the second disposable cartridge into the chamber housing causes the operational parameters to be transmitted to a memory of electrostatic applicator system, the operational parameters including at least one of a speed of the motor, an air intake, and a voltage applied to the delivery tube of the respective disposable cartridge.

55. The method of Clause 54, the method further including:

upon inserting one of the first disposable cartridge or the second disposable cartridge of the chamber housing, tagging a registry associated with information of the operational parameters of the first disposable cartridge or the second disposable cartridge as being a used cartridge; and upon determining the first disposable cartridge or the second disposable cartridge is a used cartridge, preventing the motor from actuating and/or a voltage potential to be delivered to the delivery tube of the first disposable cartridge or the second disposable cartridge.

56. The method of Clause 52, wherein the first disposable cartridge and the second disposable cartridge contain different fluids.

57. The method of Clause 47, wherein the first disposable cartridge and the second disposable cartridge include at least one of a different voltage wire and a different delivery tube depending on a respective nozzle housing, the first fluid, and/or the second fluid stored within the respective disposable cartridge.

58. The method of Clause 50, wherein providing an activation input includes inputting information related to the first fluid into a display screen on electrostatic applicator system and providing an input into the display screen.

59. The method of Clause 50, further including pairing, via a short-range wireless connection, the electrostatic applicator system to an external user device, wherein providing an activation input includes inputting information related to the first fluid into the external user device and providing an input into a display screen of the external user device.

60. A computer-implemented method for operating an electrostatic applicator system, the method including:

causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a chamber housing of the electrostatic applicator system;

advancing, by the motor urging a plunger of the syringe, fluid contents of the disposable cartridge from the syringe through the delivery tube;

electrostatically charging, by the voltage wire, the fluid contents in the delivery tube; and emitting the electrostatically charged fluid contents from a nozzle assembly of the disposable cartridge onto a treatment site.

61. The computer-implemented method of Clause 60, further comprising:

electrostatically charging, by the voltage wire, the fluid contents in a barrel portion of the syringe proximal of the delivery tube.

62. The computer-implemented method of Clause 60, wherein the step of emitting the electrostatically charged fluid contents from the nozzle assembly includes controlling air intake from an air supply of electrostatic applicator system into the disposable cartridge so as to atomize the electrostatically charged fluid contents into droplets in a predetermined spray pattern onto a target site.

63. The computer-implemented method of Clause 60, wherein the step of emitting the electrostatically charged fluid contents from the nozzle assembly includes being delivered as an electrospun fiber from the electrostatically charged fluid contents.

64. The computer-implemented method of Clause 60, further including detecting, by a proximity sensor, a distance between the electrostatic applicator system and an intended target; and in response to the distance being within a predetermined distance threshold, causing the activation input to be transmitted to actuate the motor and/or the high voltage module to deliver the voltage potential.

65. The computer-implemented method of Clause 60, further including detecting, by a proximity sensor, a distance between the electrostatic applicator system and an intended target; and in response to the distance being greater than or less than a predetermined distance threshold, preventing actuation of the motor and/or preventing the high voltage module from delivering the voltage potential.

66. The computer-implemented method of Clause 60, further including: activating, by a display screen on the electrostatic applicator system, a wake signal from one or more processors of the electrostatic applicator system in response to the one or more processors receiving a movement signal; and in response to the wake signal, causing the activation input to be transmitted to actuate the motor and/or the high voltage module to deliver the voltage potential.

67. The computer-implemented method of Clause 60, wherein the disposable cartridge includes an integrated memory including information related to operational parameters of fluid contents stored within the syringe, the method further including:
communicating, by one or more processors of the reusable electrostatic applicator, with the integrated memory to retrieve information related to the fluid contents of the disposable cartridge;
and controlling at least one of a flow rate, a voltage potential, and a nozzle setting, so as to control one or more operational parameters of the disposable cartridge, the one or more operational parameters including a motor speed, an intake of air, and/or an applied voltage of the disposable cartridge.

68. The computer-implemented method of Clause 60, wherein memory is embedded in a processor of the electrostatic applicator system and includes operation instructions for the computer-implemented method for operating the electrostatic applicator system.

69. A system for operating an electrostatic applicator system, including:
at least one memory storing instructions; and
at least one processor configured to execute the instructions to perform operations including:
causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a cartridge housing of the electrostatic applicator system;
advancing, by the motor urging a plunger of the syringe, fluid contents of the disposable cartridge from the syringe through the delivery tube;
electrostatically charging, by the voltage wire, the fluid contents while in the delivery tube; and
emitting the electrostatically charged fluid contents from a nozzle assembly of the disposable cartridge onto a treatment site.

70. The system of Clause 69, wherein the step of emitting the electrostatically charged fluid contents from the nozzle assembly includes controlling air intake from an air supply of the electrostatic applicator system into the disposable cartridge so as to atomize the electrostatically charged fluid contents into droplets in a predetermined spray pattern onto a target site.

71. The system of Clause 69, wherein the step of emitting the electrostatically charged fluid contents from the nozzle assembly includes being delivered as an electrospun fiber from the electrostatically charged fluid contents at a predetermined rate onto an a target site.

72. The system of Clause 69, the operations further including detecting, by a proximity sensor, a distance between the electrostatic applicator system and an intended target; and in response to the distance being within a predetermined distance threshold, causing the activation input to be transmitted to actuate the motor and/or the high voltage module to deliver the voltage potential.

73. The system of Clause 69, the operations further including activating, by a display screen on the electrostatic applicator system, a wake signal from one or more processors of the electrostatic applicator system in response to the one or more processors receiving a movement signal; and in response to the wake signal, causing the activation input to be transmitted to actuate the motor and/or the high voltage module to deliver the voltage potential.

74. The system of Clause 69, wherein the disposable cartridge includes an integrated memory including information related to one or more operational parameters of fluid contents stored within the syringe, the operations further including:
communicating, by one or more processors of the reusable electrostatic applicator, with the integrated memory to retrieve information related to the fluid contents of the disposable cartridge; and
controlling at least one of a flow rate, a voltage potential, and a nozzle setting, so as to control the one or more operational parameters of the disposable cartridge, the one or more operational parameters including a motor speed, an intake of air, and/or an applied voltage of the disposable cartridge.

75. The system of Clause 69, wherein memory is embedded in a processor of the electrostatic applicator system and includes operation instructions for the computer-implemented method for operating the electrostatic applicator system.

76. A non-transitory computer-readable medium storing instructions that, when executed by processor, cause the processor to perform a method for operating an electrostatic applicator system, the method including:
causing, by an activation input to the electrostatic applicator system, a motor to actuate and/or a voltage potential to be delivered from a high voltage module of the electrostatic applicator system via a voltage wire of the disposable cartridge to a delivery tube of a disposable cartridge removably attached to a system housing of the electrostatic applicator system;
advancing, by the motor urging a plunger of the syringe, fluid contents of the disposable cartridge from the syringe through the delivery tube;
electrostatically charging, by the voltage wire, the fluid contents while in the delivery tube; and emitting the electrostatically charged fluid contents from a nozzle assembly of the disposable cartridge onto a treatment site.

77. The non-transitory computer-readable medium of Clause 76, wherein the step of emitting the electrostatically charged fluid contents from the nozzle assembly includes controlling air intake from an air supply of electrostatic applicator system into the disposable cartridge so as to atomize the electrostatically charged fluid contents into droplets in a predetermined spray pattern onto an oppositely charged target site.

78. The non-transitory computer-readable medium of Clause 76, wherein the step of emitting the electrostatically charged fluid contents from the nozzle assembly includes being delivered as an electrospun fiber from the electrostatically charged fluid contents at a predetermined rate and/or a pattern onto an oppositely charged target site.

79. The non-transitory computer-readable medium of Clause 76, the method further including:
  detecting, by a proximity sensor, a distance between the electrostatic applicator system and an intended target; and
  in response to the distance being within a predetermined distance threshold, causing the activation input to be transmitted to actuate the motor and/or the high voltage module to deliver the voltage potential.

80. The non-transitory computer-readable medium of Clause 76, the method further including:
  activating, by a display screen on the electrostatic applicator system, a wake signal from one or more processors of the electrostatic applicator system in response to the one or more processors receiving a movement signal; and
  in response to the wake signal, causing the activation input to be transmitted to actuate the motor and/or the high voltage module to deliver the voltage potential.

81. The non-transitory computer-readable medium of Clause 76, wherein the disposable cartridge includes an integrated memory including information related to one or more operational parameters of fluid contents stored within the syringe, the method further including:
  communicating, by one or more processors of the reusable electrostatic applicator, with the integrated memory to retrieve information related to the fluid contents of the disposable cartridge; and
  controlling at least one of a flow rate, a voltage potential, and a nozzle setting, so as to control the one or more operational parameters of the disposable cartridge, the one or more operational parameters including a motor speed, an intake of air, and/or an applied voltage of the disposable cartridge.

What is claimed is:

1. A disposable fluid delivery system for an electrostatic applicator, comprising:
  a nozzle housing including an air supply port, a voltage port, and a delivery outlet;
  a voltage wire including a contact in communication with a delivery tube in fluid communication with the delivery outlet, the voltage wire configured to be in electrical communication with a high voltage module and electrostatically charge fluid contents within the delivery tube;
  a syringe including a barrel portion and a plunger configured to advance fluids from within the barrel portion and through the delivery tube; and
  a cartridge housing at least partially enclosing the nozzle housing, the voltage wire, and the syringe.

2. The disposable fluid delivery system of claim 1, further comprising a voltage tube in electrical communication with the voltage port, wherein the voltage wire runs between the contact in communication with the delivery tube and a contact port of a wall of the cartridge housing.

3. The disposable fluid delivery system of claim 2, wherein the voltage tube and the voltage wire comprise a substantially curved shape.

4. The disposable fluid delivery system of claim 2, wherein the syringe contains contents including one or more of an antiseptic, a disinfectant solution, an analgesic, an exosome, a biologic, and/or a liquid bandage solution.

5. The disposable fluid delivery system of claim 1, wherein the cartridge housing is a moldable plastic material, wherein the cartridge housing comprises a plurality of moldable plastic connectable sections.

6. The disposable fluid delivery system of claim 1, wherein the contact of the voltage wire comprises a wire loop at least partially surrounding an outer surface of the delivery tube to provide a voltage potential of approximately 1 V to approximately 40 kV.

7. The disposable fluid delivery system of claim 1, wherein the contact of the voltage wire is in physical contact with the delivery tube to provide a voltage potential of approximately 1 V to approximately 40 kV.

8. The disposable fluid delivery system of claim 1, wherein the delivery tube, when assembled with the syringe and the nozzle housing, is configured to receive air from the air supply port and fluid from the barrel portion of the syringe and expel fluid equally charged by the voltage wire.

9. The disposable fluid delivery system of claim 1, further comprising:

a reusable electrostatic applicator including a cartridge chamber sized and shaped to accept the cartridge housing, the reusable electrostatic applicator including:

a high voltage module configured to be in in electrical communication with the voltage wire; and a piston positioned proximate the cartridge chamber and configured to advance the plunger enclosed in the cartridge housing when the cartridge housing is assembled with the cartridge chamber.

10. The disposable fluid delivery system of claim 9, wherein the reusable electrostatic applicator comprises:

a motor configured to move the piston;

one or more processors; and memory storing instructions that, when executed by the one or more processors, causes the reusable electrostatic applicator to:

receive an activation signal;

output a control signal to the motor to actuate the piston; and output a control signal to a switch to provide voltage from the high voltage module to the voltage wire.

11. The disposable fluid delivery system of claim 10, wherein the reusable electrostatic applicator comprises:

a housing base comprising a voltage source;

a device housing comprising the cartridge chamber; and a handle extending between the housing base and the device housing.

12. The disposable fluid delivery system of claim 11, wherein the cartridge chamber is positioned within the device housing such that an actuator is positioned below the cartridge chamber with respect to horizontal.

13. An electrostatic applicator system for delivering a treatment solution to a target site, comprising:

a portable reusable electrostatic applicator comprising:

a device housing configured to be handheld;

a motor in the device housing configured to drive a piston;
a voltage source in the device housing;
a high voltage module electrically connected to the voltage source; and
a cartridge chamber; and
a disposable cartridge removably insertable in the cartridge chamber, the disposable cartridge comprising:
a nozzle housing comprising an air supply port, a voltage port, and a delivery outlet;
a voltage wire comprising a contact in communication with a delivery tube in fluid communication with the delivery outlet;
a syringe comprising a barrel portion and a plunger configured to advance fluids from within the barrel portion and through the delivery tube; and
a cartridge housing at least partially enclosing the nozzle hous